US006997931B2

(12) United States Patent
Sauer et al.

(10) Patent No.: US 6,997,931 B2
(45) Date of Patent: Feb. 14, 2006

(54) SYSTEM FOR ENDOSCOPIC SUTURING

(75) Inventors: Jude S. Sauer, Pittsford, NY (US); Michael W. Fitzsimmons, Rochester, NY (US); Mark A. Bovard, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 315 days.

(21) Appl. No.: 09/776,431

(22) Filed: Feb. 2, 2001

(65) Prior Publication Data

US 2002/0107530 A1 Aug. 8, 2002

(51) Int. Cl.
*A61B 17/10* (2006.01)

(52) U.S. Cl. .................. 606/139; 606/144; 606/148; 606/149; 606/150; 600/104; 600/105; 600/106; 600/107; 604/22

(58) Field of Classification Search ............... 606/139, 606/144, 148, 149, 150; 600/104–107; 604/22
See application file for complete search history.

(56) References Cited

U.S. PATENT DOCUMENTS

| 4,841,888 | A | | 6/1989 | Mills et al. |
|---|---|---|---|---|
| 4,960,410 | A | | 10/1990 | Pinchuk |
| 5,037,021 | A | | 8/1991 | Mills et al. |
| 5,080,663 | A | | 1/1992 | Mills et al. |
| 5,165,590 | A | * | 11/1992 | Cini et al. .................. 228/175 |
| 5,368,601 | A | | 11/1994 | Sauer et al. |

(Continued)

FOREIGN PATENT DOCUMENTS

| EP | 0 669 103 A1 | 8/1995 |
|---|---|---|
| EP | 0 568 098 B1 | 10/1997 |
| EP | 0 669 102 B1 | 10/1998 |

OTHER PUBLICATIONS

Gong, F. et al., "Cutting Thread at Flexible Endoscopy", Gastrointestinal Endoscopy, vol. 44, No. 4, 667–679 (1996).

Kadirkamanathan, S. et al., "Antireflux Operations at Flexible Endoscopy Using Endoluminal Stitching Techniques: An Experimental Study", Gastrointestinal Endoscopy, vol. 44, No. 2, 144–162 (1996).

Swain, C. et al., "An Endoscopically Deliverable Tissue–Transfixing Device for Securing Biosensors in the Gastrointestinal Tract", Gastrointestinal Endoscopy, vol. 40, No. 6, 730–737 (1994).

Rich, P., "Simple GERD Treatment Offers New Alternative", The Medical Post, vol. 35, No. 11, 1–3 (1999).

Filipi, C., "Totally Endoscopic Antireflux Surgery: A Clinical Trial of the BARD Endoscopic Sewing Device", Creighton Univ., Cardiothoracic Update, vol. 1, No. 6, 1–3 (1998).

Brochure entitled "SEW–RIGHT SR•5, The Single Squeeze Suturing Device", LSI Solutions, Copyright 2000.

Brochure entitled "Ti–KNOT TK•5, The Device to Instantly Secure and Trim Suture", LSI Solutions, Copyright 2000.

Brochure entitled "The EndoCinch Procedure, BARD's Unique New Endoscopic Suturing System for treating Symptomatic GERD".

*Primary Examiner*—John J. Calvert
*Assistant Examiner*—Robert H. Muromoto, Jr.
(74) *Attorney, Agent, or Firm*—Kenneth J. Lukacher

(57) ABSTRACT

A system for endoscopic suturing is provided having an endoscope, such as a gastroscope, with a distal end locatable in the body of a patient and a flexible shaft extending to the distal end, a flexible accessory tube coupled to the endoscope to be movable relative to the endoscope's shaft, and a tip coupled to the shaft of the endoscope having an opening through which one end of the accessory tube is received. The system further includes a tissue suturing instrument and a suture securing instrument. Each of these instruments has a distal end coupled to a partially flexible shaft locatable through the accessory tube.

53 Claims, 74 Drawing Sheets

U.S. PATENT DOCUMENTS

| | | | |
|---|---|---|---|
| 5,391,173 A | 2/1995 | Wilk | |
| 5,431,666 A | 7/1995 | Sauer et al. | |
| 5,507,757 A | 4/1996 | Sauer et al. | |
| 5,520,702 A | 5/1996 | Sauer et al. | |
| 5,562,686 A | 10/1996 | Sauer et al. | |
| 5,584,861 A | 12/1996 | Swain et al. | |
| 5,626,588 A | 5/1997 | Sauer et al. | |
| 5,626,590 A | 5/1997 | Wilk | |
| 5,643,289 A | 7/1997 | Sauer et al. | |
| 5,669,917 A | 9/1997 | Sauer et al. | |
| 5,722,990 A | * 3/1998 | Sugarbaker et al. | 606/207 |
| 5,755,730 A | 5/1998 | Swain et al. | |
| 5,766,183 A | 6/1998 | Sauer | |
| 5,792,153 A | 8/1998 | Swain et al. | |
| 5,810,805 A | * 9/1998 | Sutcu et al. | 606/45 |
| 5,817,013 A | * 10/1998 | Ginn et al. | 600/114 |
| 5,908,429 A | 6/1999 | Yoon | |
| 5,910,105 A | 6/1999 | Swain et al. | |
| 5,954,731 A | * 9/1999 | Yoon | 606/144 |
| 6,071,233 A | * 6/2000 | Ishikawa et al. | 600/104 |

* cited by examiner

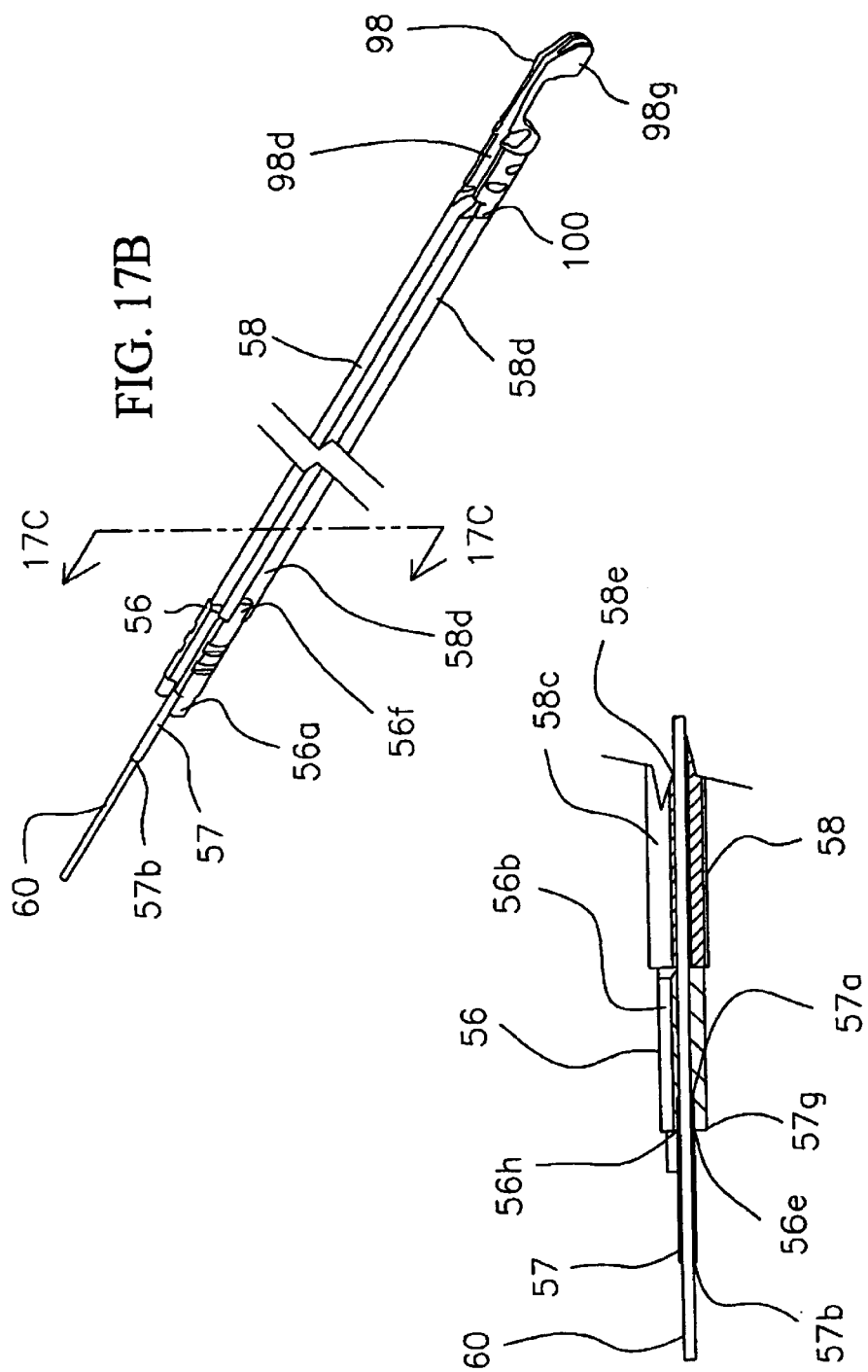

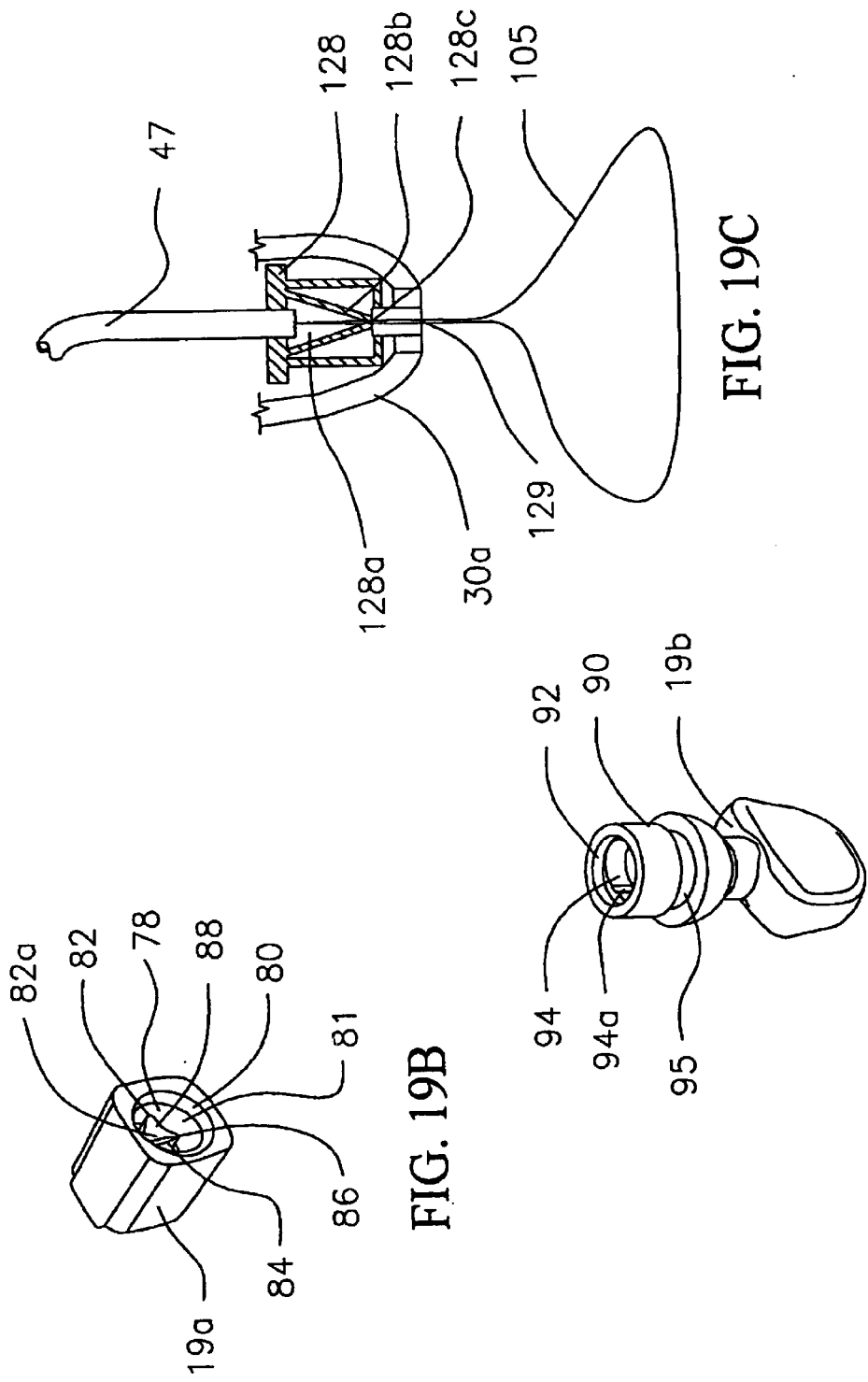

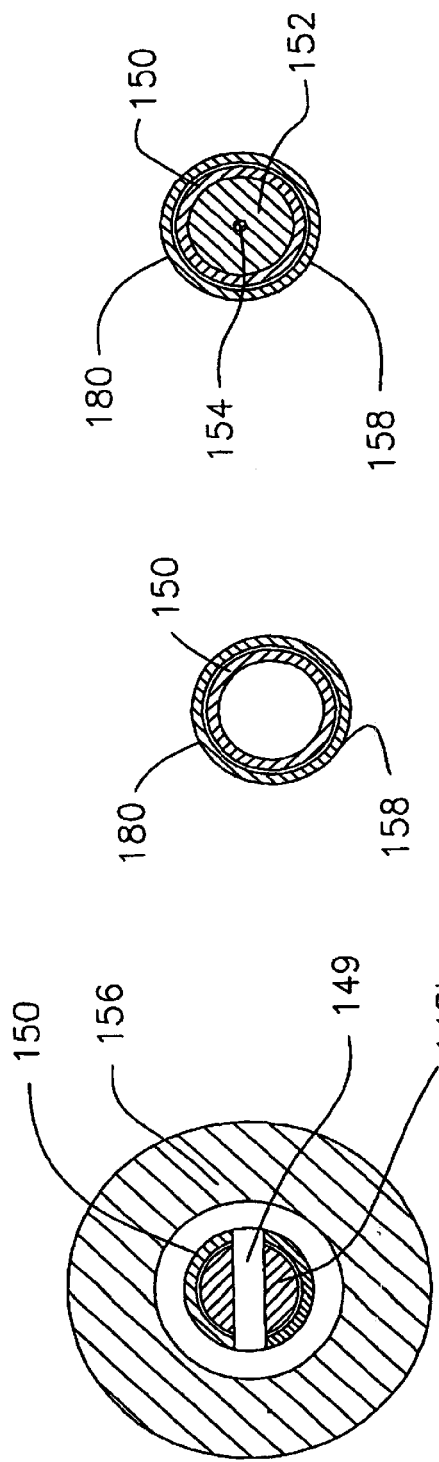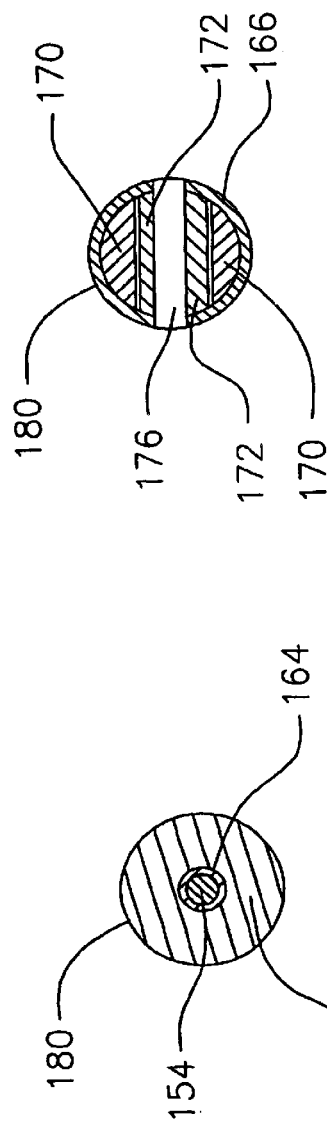

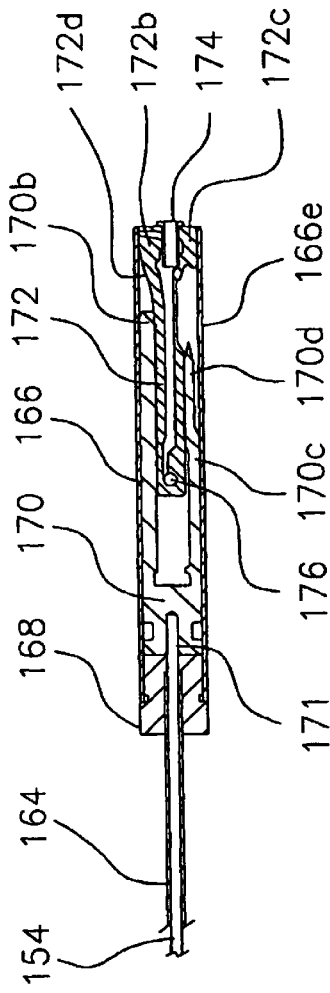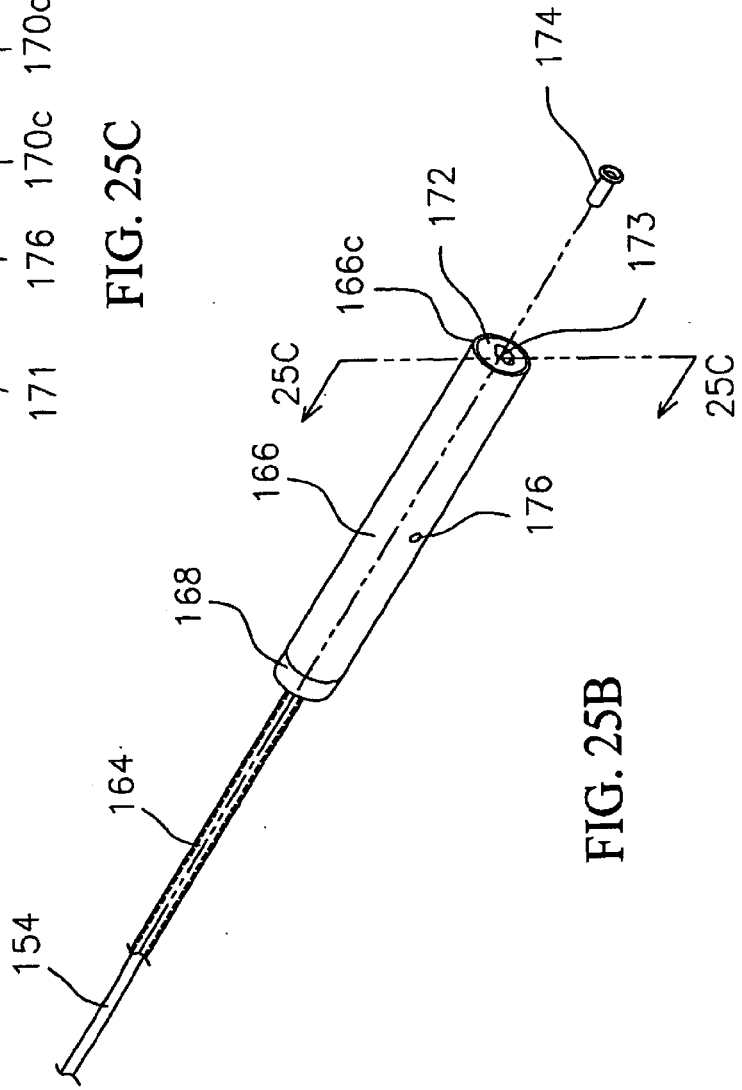
FIG. 25C
FIG. 25B

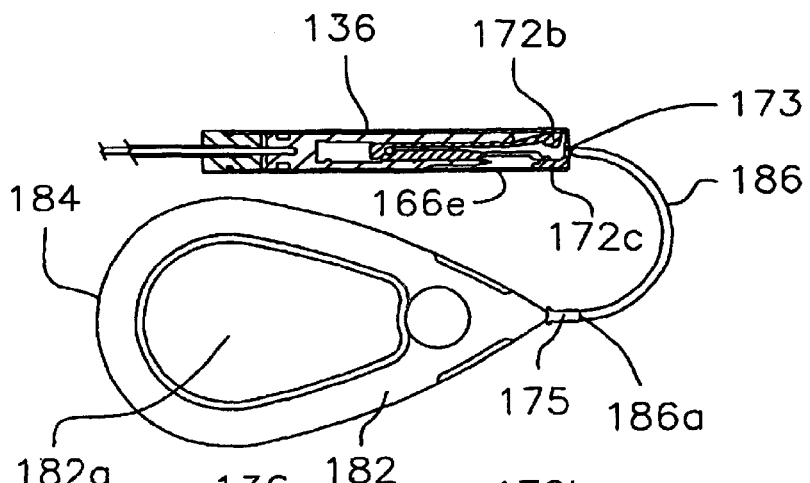
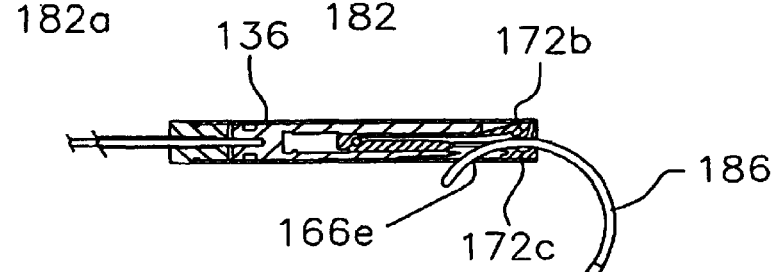
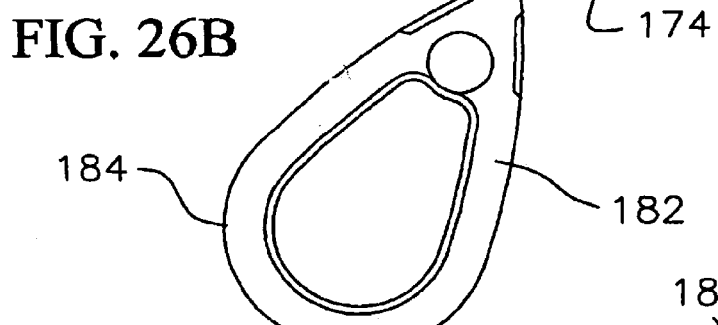
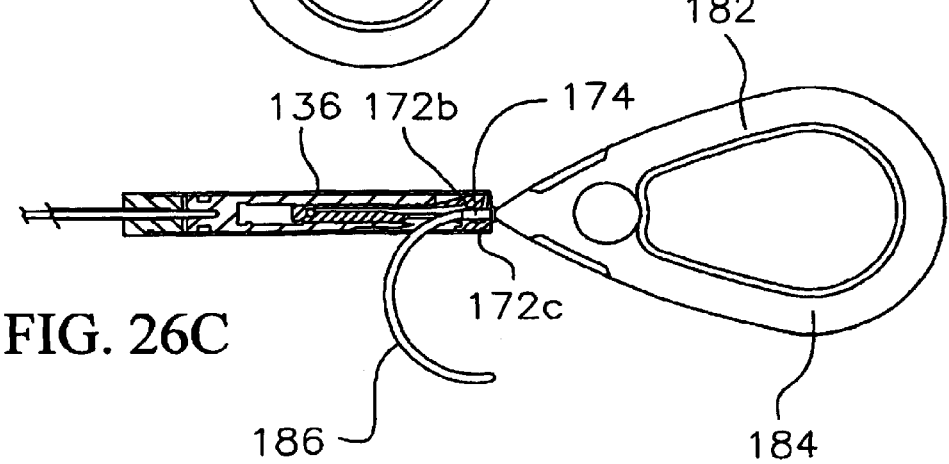
FIG. 26A
FIG. 26B
FIG. 26C

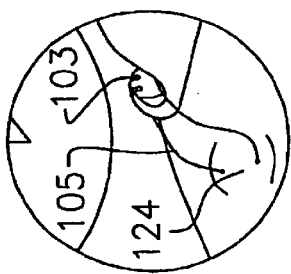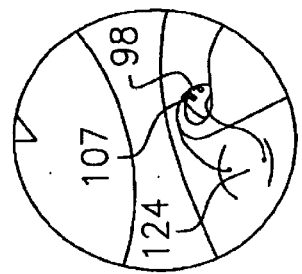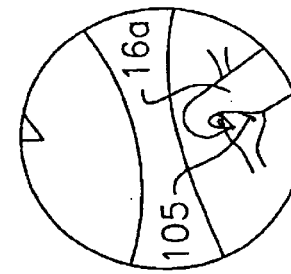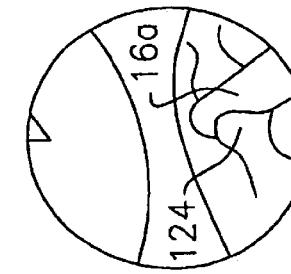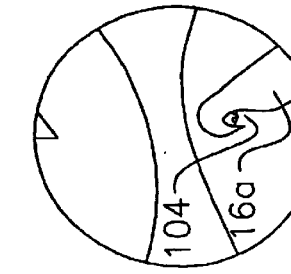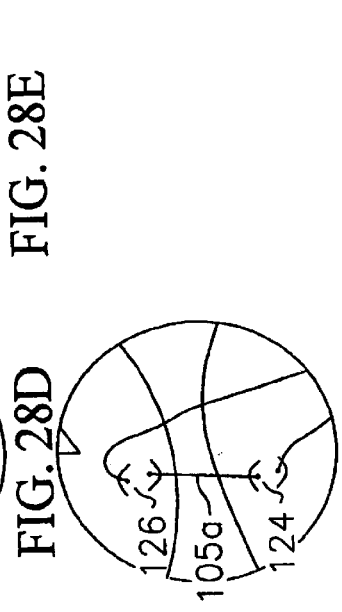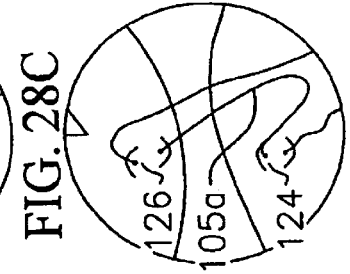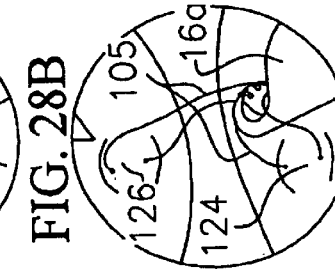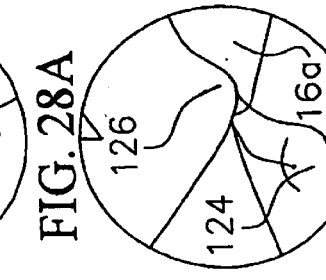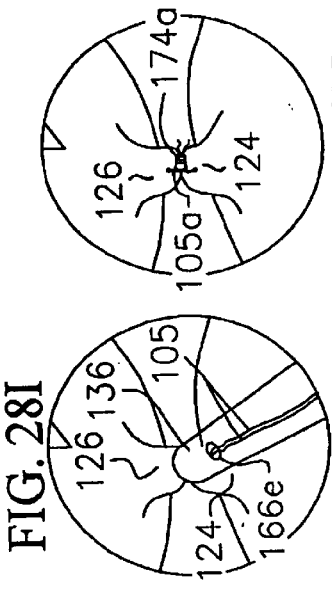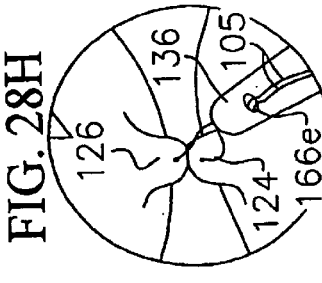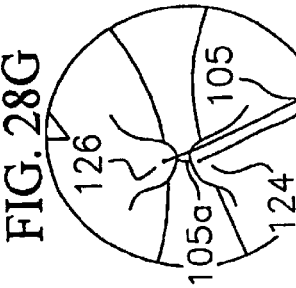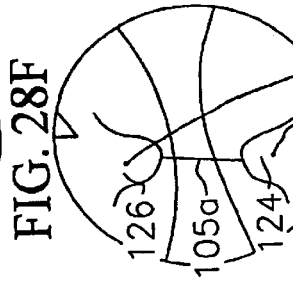

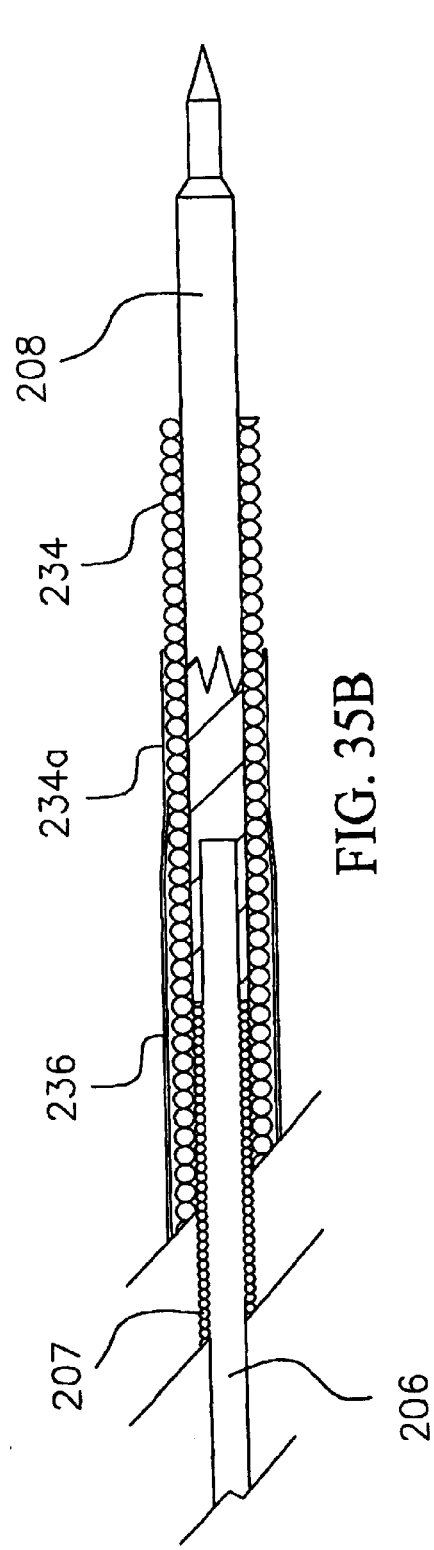
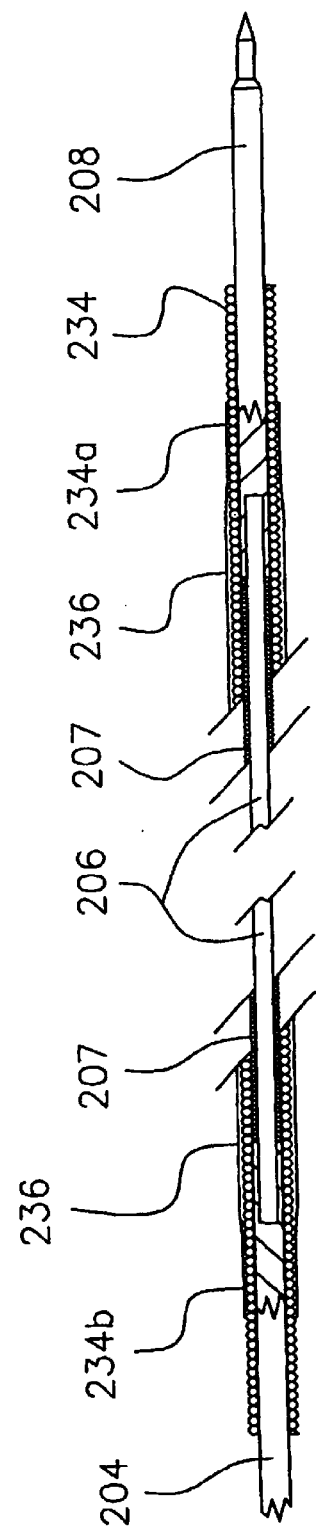

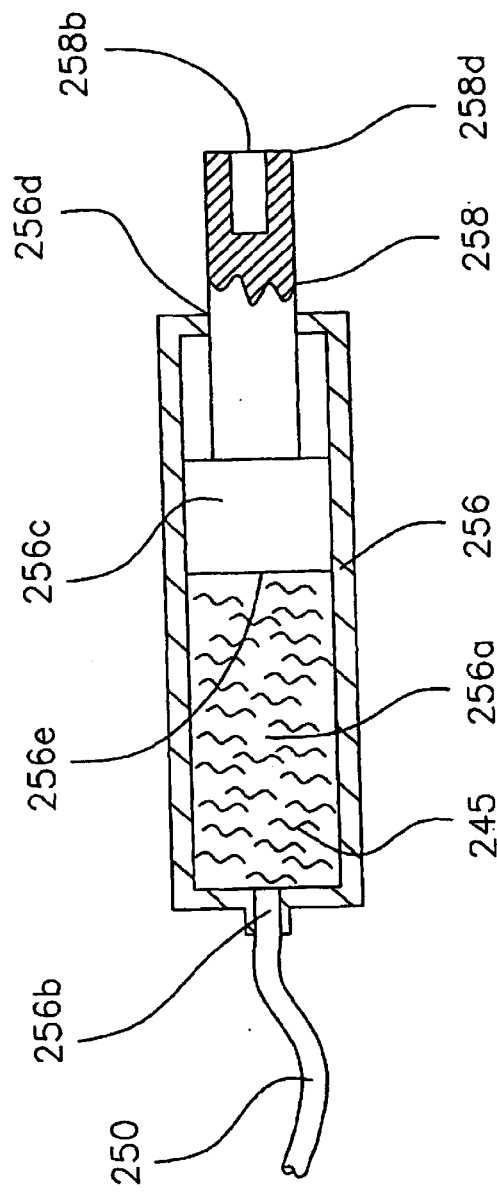
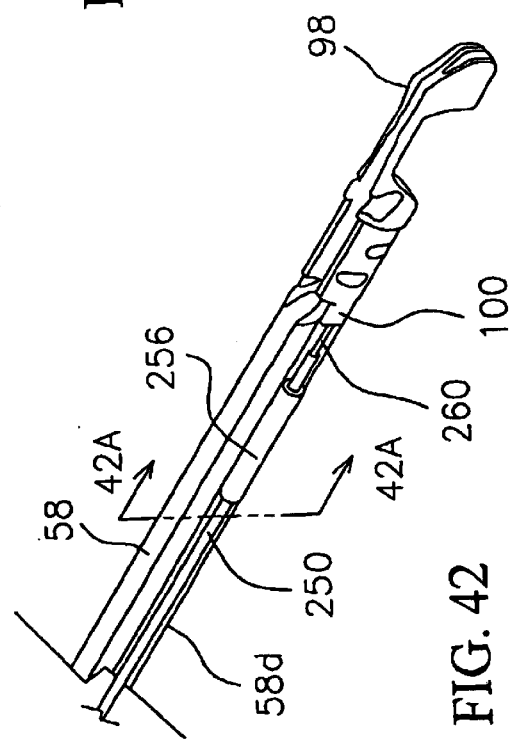
FIG. 42A
FIG. 42

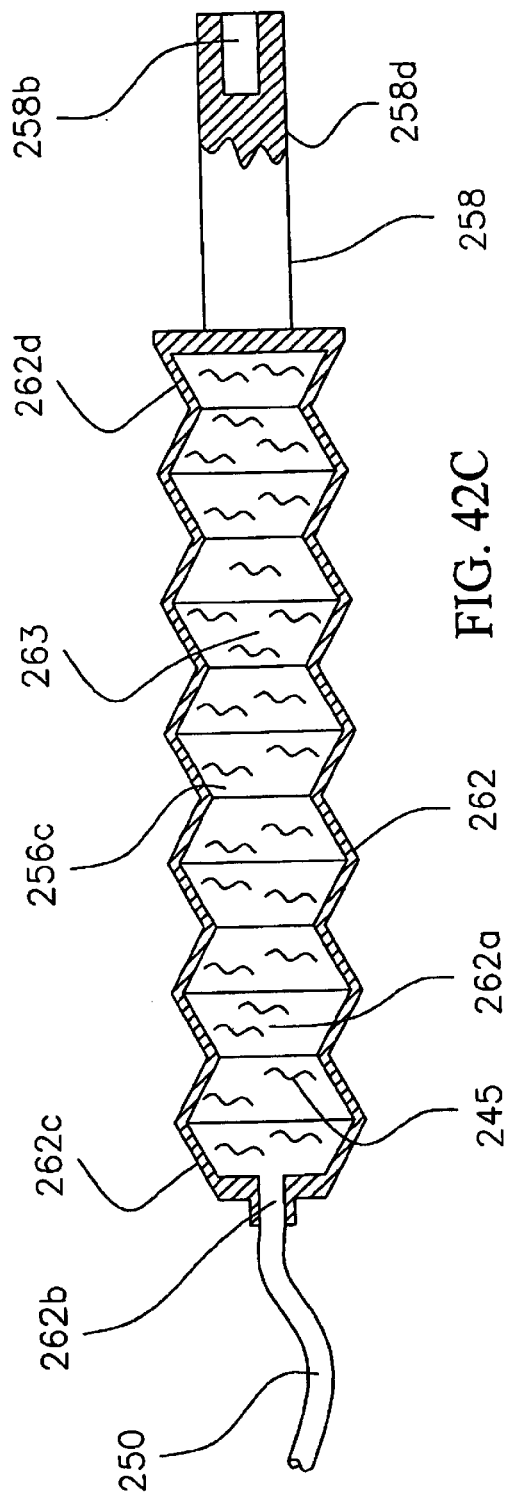
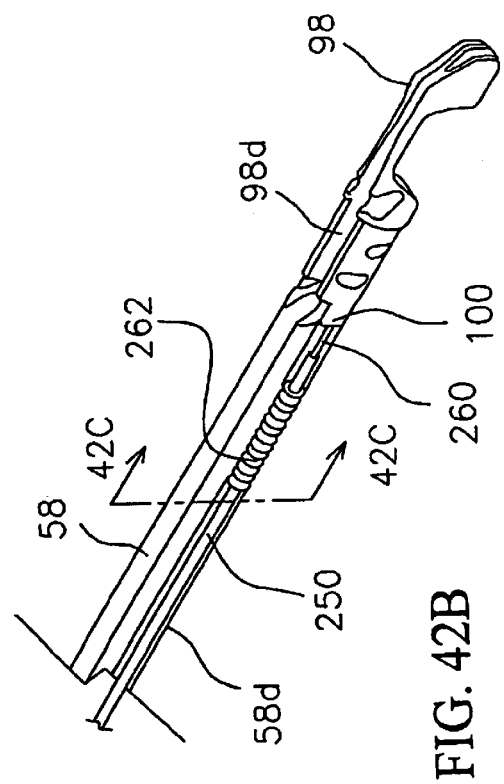
FIG. 42C
FIG. 42B

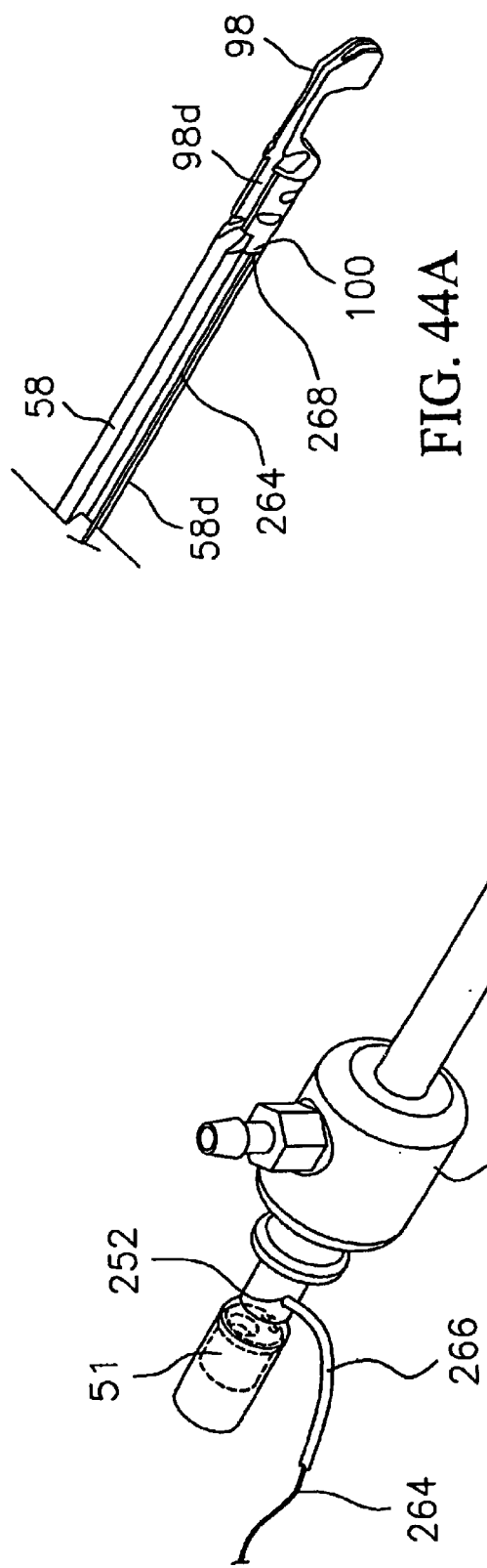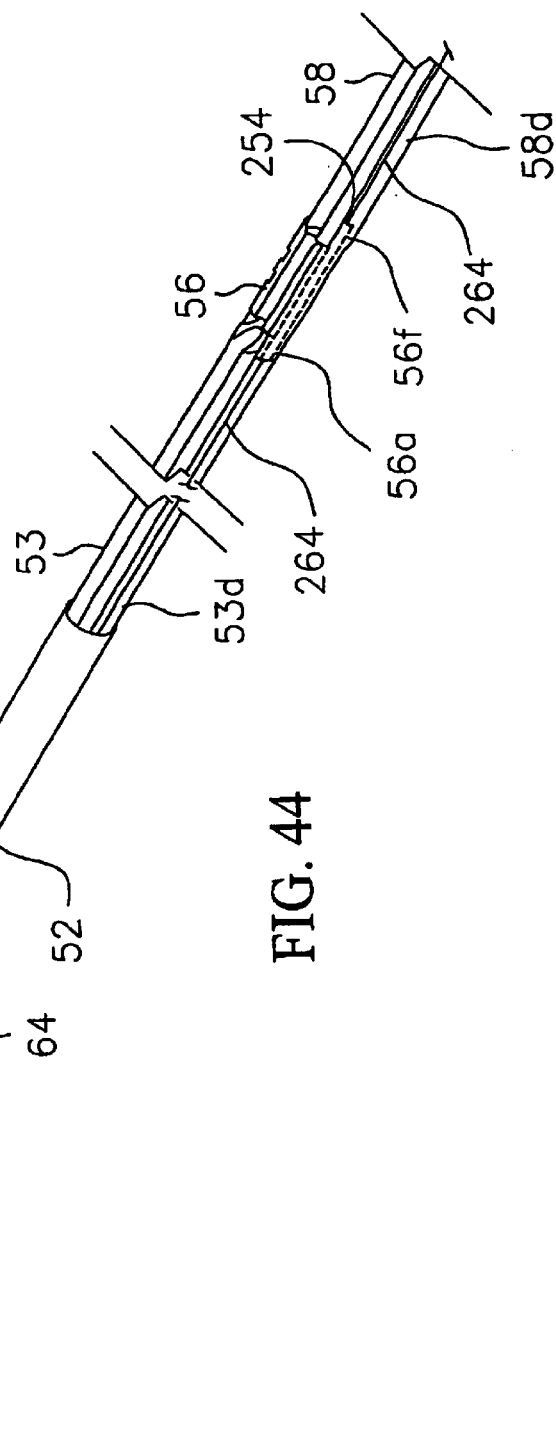

SYSTEM FOR ENDOSCOPIC SUTURING

FIELD OF THE INVENTION

The present invention relates to a system (and method) for endoscopic suturing, and in particular to a system for suturing through an accessory tube coupled to a flexible endoscope, which may be placed in the stomach through mouth and the esophagus of a patient utilizing a tissue suturing instrument and a suture securing instrument. The invention is suitable, for example, for applying at least one suture in the soft tissue lining of the stomach for different procedures such as gastroplasty, fundoplication, anterior gastropexy, or other procedures requiring suturing in the stomach, without the need for laparotomy or laparoscopy.

BACKGROUND OF THE INVENTION

Application of sutures in the gastrointestinal tract is required for several different types of medical procedures, for example, transoral endoscopic valvuloplasty for gastroesophageal reflux disease, gastroplasty, fundoplication, anterior gastropexy, suturing esophageal perforations, or closure of esophageal side of tracheo-esophageal fistula. Traditionally, these procedures were performed by physicians, such as gastroenterologist or surgeons, either by laparoscopy or open surgical techniques. Such procedures are invasive, as laparoscopy requires small access incision (s) made in the body of the patient through which a laparoscope and other surgical enabling tools are provided, while open surgical techniques are traditionally invasive and can have complications and long patient recovery periods.

The solution to these problems is to perform these medical procedures through the gastroesophageal tract via the mouth or other naturally occurring orifices. Already available flexible endoscopes, commonly called gastroscopes, can be provided through the gastroesophageal tract and enable illumination and visualization of tissue along the gastroesophageal tract on a video display for diagnostic purposes. Although gastroscopes often have a working channel to a port at the distal end of the gastroscope through which a biopsy tool may be provided to obtain tissue samples, they are not currently designed or typically large enough to be capable of applying sutures in tissue.

U.S. Pat. No. 5,792,153 describes a sewing device coupled to the distal end of an endoscope, which enables suturing in the gastroesophageal tract of a patient. The sewing device has a single hollow needle mounted in the biopsy channel of the endoscope, and a wire extending through the needle to a T-shaped tag having one end of a suture thread which extends outside of the patient. To apply a suture, suction is applied to a U-shaped opening of the sewing device via another channel of the endoscope to suck a layer (or fold) of tissue into the U-shaped opening, the needle in the biopsy channel is then pushed through the tissue, and then the wire is pushed and rotated to position the tag in a chamber along one side of the U-shaped opening. This rotates the tag into a position which captures the tag and the suture end in this chamber, and the needle and wire are retracted to the other side of the U-shaped opening. The endoscope and its coupled sewing device are removed from the patient, leaving a loop of suture through the tissue which must then be secured and closed. The patent also provides another sewing device at the end of an endoscope which enables multiple stitches in tissue with the same needle and suture thread. The sewing device of U.S. Pat. No. 5,792,153 to apply a single stitch is manufactured by Laboratories BARD S.A. of Voisinsle Bretonneux, France, and described in Kadirkamanathan et al., Gastrointestinal Endoscopy, August 1996, Vol. 44, No. 2, pp.144–162.

Once the suture thread is placed through the tissue with the sewing device of U.S. Pat. No. 5,792,153, the suture thread must be secured and then cut close to the tissue. One device also manufactured by Laboratories BARD S.A., and described in U.S. Pat. No. 5,755,730, provides for securing and cutting suture using an endoscope. The device passes through the biopsy channel of the endoscope is order to push a knot made by a physician or surgeon, which ties the ends of a loop of suture thread together, down to the tissue, and then a cutting member cut the ends of the suture. Since the sewing device of U.S. Pat. No. 5,792,153 does not allow normal use of its biopsy channel of the endoscope upon which the sewing device is mounted, a second endoscope must be used to secure and cut the suture through its biopsy channel using the device described in U.S. Pat. No. 5,755,730. This results in multiple passes of endoscopes back and forth through the gastroesophageal tract, especially if single sutures are each applied and secured at multiple locations in tissue. To reduce possible damage to the esophageal tract and to facilitate multiple instrument insertions, an overtube is first placed in the esophageal tract and each endoscope is inserted and removed through the overtube. However, the overtube may be uncomfortable to patients, and can cause complications, such as mucosal tears in the esophagus. Accordingly, it would be desirable to provide a system for suturing which does not require different endoscopes for suture placement and suture securing, and moreover can apply and secure multiple single sutures in tissue with the single insertion of a flexible endoscope, i.e., gastroscope without requiring an overtube.

Other sewing devices or machines mounted on the end of an endoscope are described in U.S. Pat. Nos. 5,037,021 and 4,841,888. These sewing devices similarly utilize two channels of the endoscope, one to suction tissue into a slot of the device and the other to advance and retract a wire coupled to needle through the tissue. The needle has a suture loop at its tip such that when the needle is advanced through the slot it extends into a chamber where a hook or U-shaped member pivots to retain the suture loop when the needle retracts. A wire is coupled to the hook and extends through the same channel where suction is provided, such that movement of this wire pivot the hook to capture the suture thread. Removal of the sewing device then leaves a loop of suture through the tissue.

A further sewing device is described in U.S. Pat. No. 5,080,663 and also utilizes an operating device having tubes in a tubular sheath, such as endoscopic means, to provide suction to a slot in the device to capture a double fold of tissue and two wires extending through such tubes. One wire advances and retracts a needle having a tag with suture at its tip through tissue and the other wire controls capture of a tag at the other side of the opening. The patent provides for applying a sensor or transmitter in the body of a patient, such as the stomach. This sewing device is also described in Swaine et al., An endoscopically deliverable tissue-transfixing device for securing biosensors in the gastrointestinal tract, Gastrointestinal Endoscopy, November/December 1994, Vol. 40, No. 6, pp. 730–737.

Like the sewing devices of U.S. Pat. No. 5,792,153, those described in U.S. Pat. Nos. 5,037,021 4,841,888, and 5,080,663 have the same drawbacks as these devices are also mounted on an endoscope. Moreover, mounting on an endoscope limits the use of the endoscope for full visualization of tissue, as the sewing device partially obstructs the viewing area at the distal end of the endoscope. Further the use of the biopsy or working channel of an endoscope for needle placement does not allow use of the channel for other purposes, such as obtaining a biopsy. Accordingly, it would further be desirable to provide for suturing with a flexible endoscope which allows for more complete traditional use of the endoscope.

SUMMARY OF THE INVENTION

Accordingly, it is the principal object of the present invention to provide an improved system for endoscopic suturing that overcomes the drawbacks of the prior art.

It is another object of the present invention to provide an improved system for endoscopic suturing which allows single insertion of an endoscope and accessory tube assembly in the gastrointestinal tract of a patient through which multiple instruments for suturing and securing sutures can be used without removal of the endoscope between suturing and suture securing operations.

It is a further object of the present invention to provide an improved system for endoscopic suturing which provides a channel to sew through independent of an endoscope.

Yet a further object of the present invention is to provide an improved system for endoscopic suturing in which a suturing instrument separate from an endoscope can utilize suction to capture tissue to be sutured.

A still further object of the present invention is to provide an improved system for remote suturing in which can readily adapted to different types of flexible endoscopes to provide an external accessory tube through which medical or surgical instruments can pass.

A still further object of the present invention is to provide an improved system for endoscopic suturing which utilizes one or more instruments which each have a sufficient flexible shaft to pass through an external flexible accessory tube attached to a flexible endoscope.

A further object of the present invention is to provide an improved system for endoscopic suturing using instruments having shafts with enhanced flexibility.

And a still further object of the present invention is to provide an improved system for endoscopic suturing using flexible instruments with mechanical or hydraulic steerability.

Yet a further object of the present invention is to provide an improved system for endoscopic suturing in which remote viewing with an endoscope of suture and suture securing operations is provided in the stomach without hindering endoscope functionality.

Briefly described, a preferred embodiment of this system embodying the invention includes an endoscope, such as a gastroscope, having a distal end locatable in the body of a patient, such as in the gastrointestinal or gastroesophageal tract, and a flexible shaft extending to the distal end, a flexible accessory tube coupled to the endoscope to be movable relative to the endoscope's shaft, and an attachment tip coupled to the shaft of the endoscope having an opening through which one end of the accessory tube is received. The accessory tube is coupled to the shaft of the endoscope with multiple tube guides enabling the accessory tube to slide through the tube guides in response to bending of the endoscope's shaft. The accessory tube has a cannula through which an instrument may pass in the accessory tube. The system includes a tissue suturing instrument having a partially flexible shaft locatable through the accessory tube, and a tissue engaging end coupled to the shaft which is viewable by the endoscope at its distal end when the instrument is fully inserted through the accessory tube. The tissue engaging end has a vacuum sleeve enabling suction to be selectably applied at the tissue engaging end to capture tissue in a gap of a sew tip through an opening in the vacuum sleeve. Suction is applied via a vacuum connection assembly to a channel which extends down the shaft to the sew tip. A valve is provided to close one end of the suture carrying channel to enable such suction at the sew tip. Two needles are provided which extends through the shaft of the suturing instrument. Each needle is separately actuated into the gap of the sew tip through suctioned tissue to capture a ferrule having one end of a loop of suture. The system further includes a suture securing instrument having a partially flexible shaft locatable through the accessory tube, and a distal end coupled to the shaft which is viewable by the endoscope at its distal end when the instrument is fully inserted through the accessory tube. After removal of the suturing instrument from the accessory tube, a loop of suture extends through the tissue through the accessory tube, the suture securing instrument receives the free ends of the loop of suture at its distal end through a sleeve member, and the suture securing instrument is then inserted through the accessory tube to the location of the suture in the tissue. The suture securing instrument crimps the sleeve member and cuts the free ends of the suture to retain the suture closed. The endoscope enable an operator, such as a surgeon, gastroenterologist, or other skilled physician, to view the engaging end of the suturing instrument for selecting placement of the suture through tissue, and of the distal end of the suture securing instrument to secure the suture closed.

The suturing instrument in the system may further include a mechanism for steering the tissue engaging end of the instrument independent of steerability of the flexible endoscope.

A method embodying the present invention is also provided having the steps of: locating an endoscope, such as a gastroscope, coupled to an accessory tube through the gastrointestinal or gastroesophageal tract of a patient; inserting a suturing instrument through the accessory tube to place two ends of a loop of suture through tissue of the gastrointestinal or gastroesophageal tract; removing the suturing instrument to leave a loop of suture in the tissue having two free ends extending from the accessory tube; inserting a suture securing instrument having a distal end with a sleeve member through which the free ends of the suture loop are drawn to the suture in the tissue to crimp the sleeve member and cut the free ends of the suture; and removing the suture securing instrument from the accessory tube.

Optionally, the suturing instrument and suture securing instrument may be used without the accessory tube when an internal working of biopsy channel is provided in the endoscope that permits the passage of the shaft of the suturing instrument and suture securing instrument, respectively.

The following description referring to the endoscope as a gastroscope for purposes of illustration. Other types of endoscopes may be used in the system and method.

BRIEF DESCRIPTION OF THE DRAWINGS

The foregoing objects, features and advantages of the invention will become more apparent from a reading of the following description in connection with the accompanying drawings, in which:

FIG. 1A is a partial view of endoscope shaft of FIGS. 1 and 2 showing the attachment of a tube guide to the endoscope while enabling the accessory tube to be slidable through the tube guide in response to flexing of the endoscope's shaft;

FIG. 1B is an expanded view of the distal end of the system of FIG. 1;

FIG. 2A is an expanded view of the distal end of the system of FIG. 2;

FIG. 10A is a perspective view of the retainer member of the suturing instrument of FIGS. 9 and 10;

FIG. 10B is a side view of the cam member of the suturing instrument of FIGS. 9 and 10;

FIG. 17B is a perspective view showing the connection of the coupler member, sew tip, and the guide member of FIG. 17A;

FIG. 17C is a cross-sectional view along lines 17C—17C of the FIG. 17B;

FIGS. 19A and 19B are perspective view of the valve seat and valve knob of the valve of the suturing instrument of FIGS. 9 and 10;

FIG. 19C is schematic diagram of an alternative valve for the suturing instrument of FIGS. 9 and 10;

FIG. 24C is a cross-sectional view through lines 24C—24C of the suture securing instrument of FIG. 24A.

FIG. 24D is a cross-sectional view through lines 24D—24D of the suture securing instrument of FIG. 24A.

FIG. 24E is a cross-sectional view through lines 24E—24E of the suture securing instrument of FIG. 24A.

FIG. 24F is a cross-sectional view through lines 24F—24F of the suture securing instrument of FIG. 24A.

FIG. 24G is a cross-sectional view through lines 24G—24G of the suture securing instrument of FIG. 24A.

FIGS. 25A and 25B illustrate the assembly of the distal end of the suture securing instrument of FIG. 24;

FIG. 25C is a cross-section of the distal end of the suture securing instrument along lines 25C—25C of FIG. 25B;

FIGS. 26A–26D illustrates the use of a loading device for placement of a sleeve member into the distal end of the suture securing instrument of FIG. 24, in which FIG. 26D further illustrates a guide wire loop for loading of suture in the instrument;

FIGS. 28A–28N represent an example of the view through the endoscope for applying of a suture by the suturing instrument of the system of FIG. 1 and then secured in place by a suture securing instrument of the system;

FIG. 32A is a partial perspective view of an example of the needles of FIG. 31 extending through one end of the multi-lumen tube of FIG. 32;

FIG. 35A is a schematic diagram of alternative needle carrying tubes of FIGS. 33–35;

FIG. 35B shown in more detail one end of the needle carrying tube of FIG. 35A;

FIGS. 40, 40A, 41, 42, 42A–42C, and 45A–45D are diagrams illustrating an optional hydraulic steering mechanism for the tissue engaging end of the suturing instrument of FIG. 1 using a cylinder of FIGS. 42 and 42A or folding piston of FIGS. 42B–C and 45A–45D; and FIGS. 43, 43A, 44, and 44A are diagrams illustrating an optional mechanical steering mechanism for the tissue engaging end of the suturing instrument of FIG. 1.

DETAILED DESCRIPTION OF THE INVENTION

Figure 1:
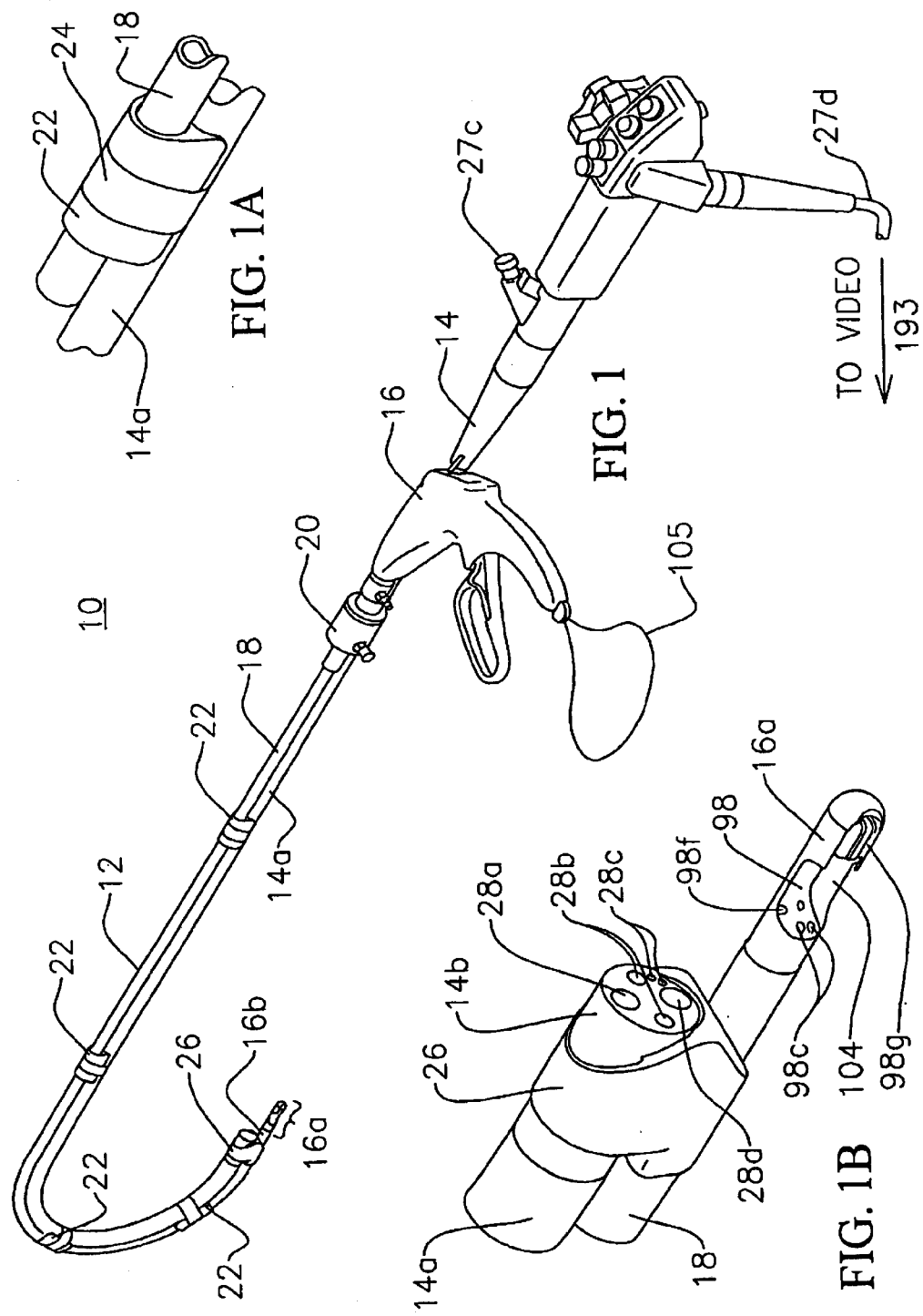
FIG. 1 is a perspective view of the system in accordance with the present invention for application of a suture in tissue.
Figure 2:
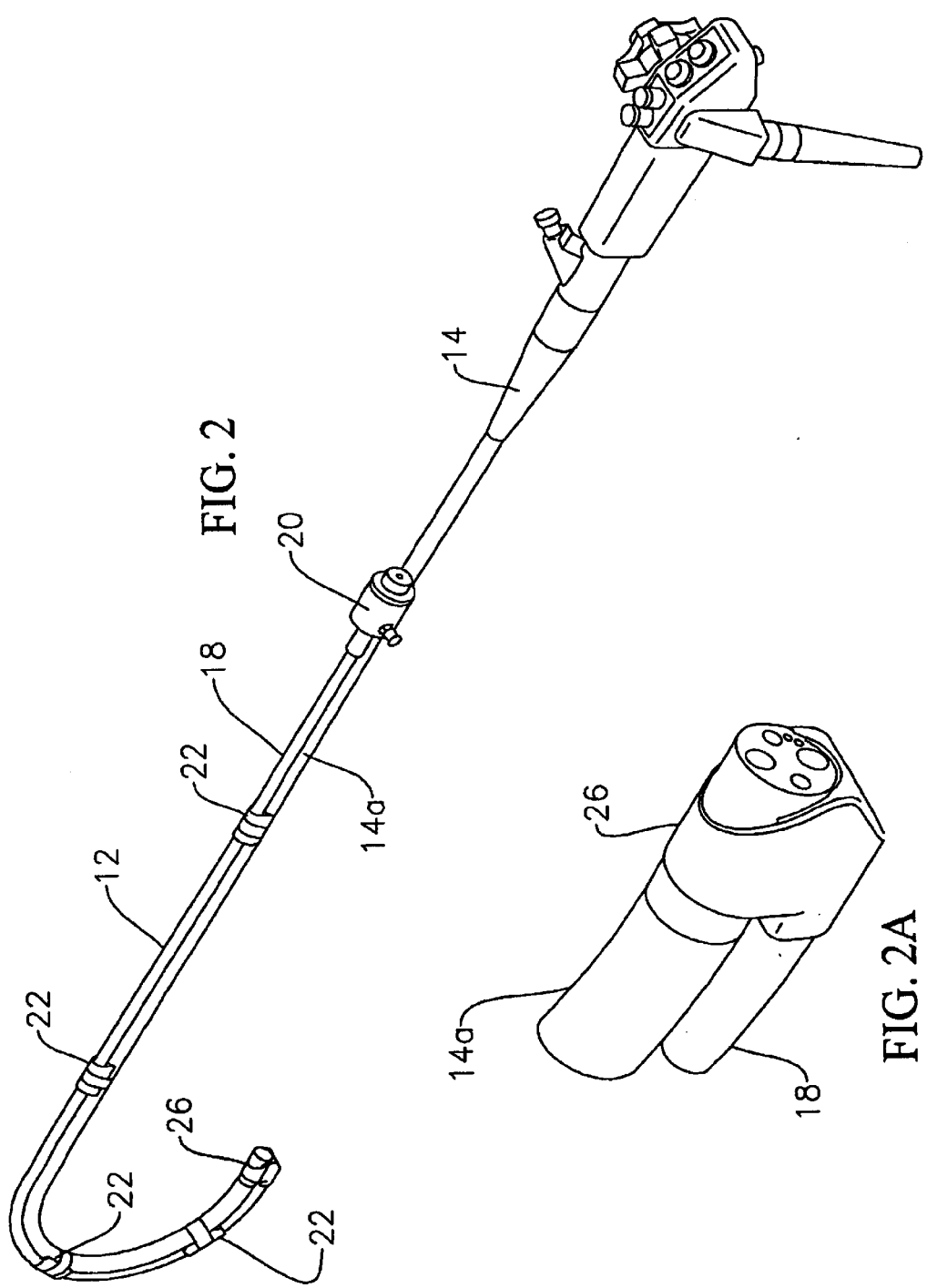
FIG. 2 is a perspective view of the system of FIG. 1 with the suture instrument of the system removed.
Figure 6:
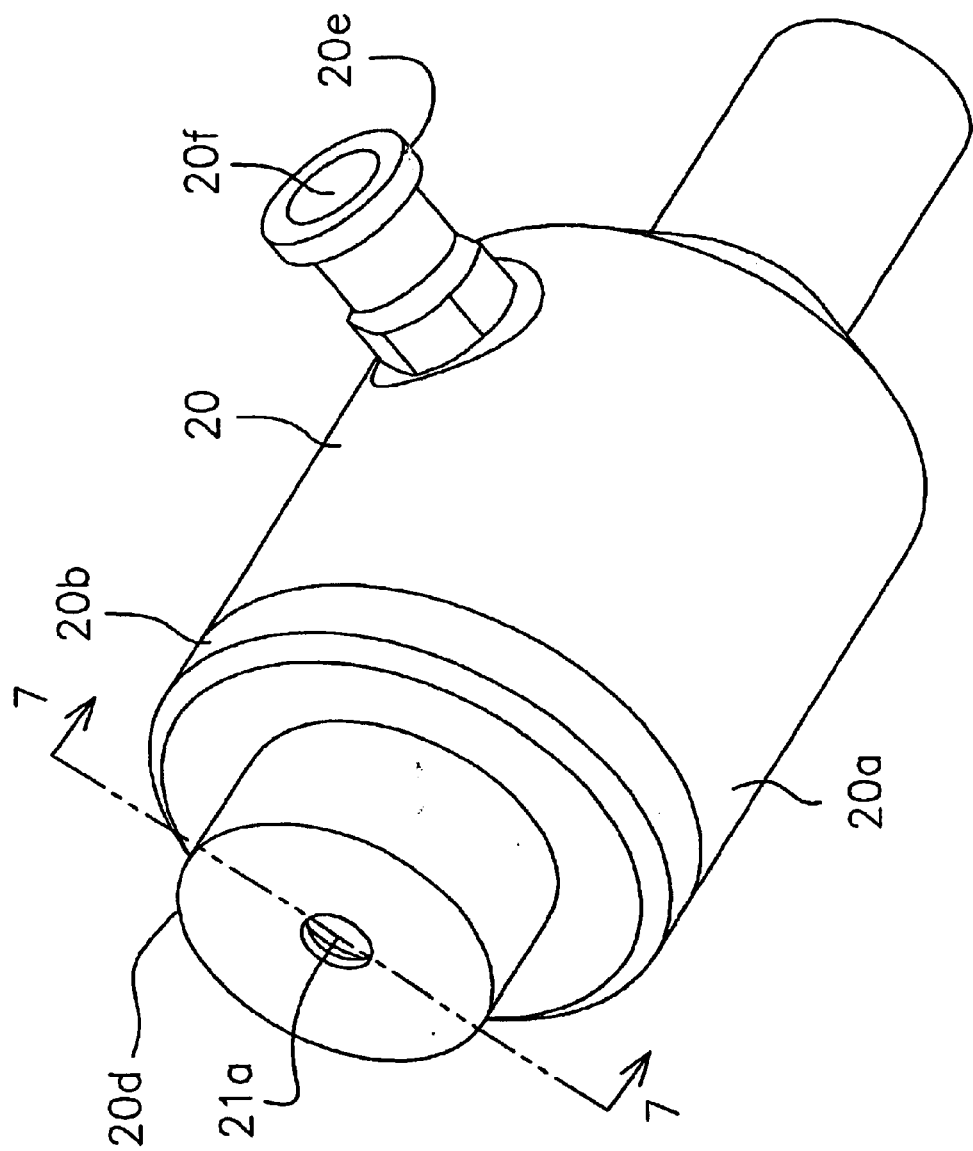
FIG. 6 is a perspective view of the cannula of FIG. 3.

Referring to FIG. 1, a system 10 for suturing is shown including an accessory tube 12 and an endoscope 14, referred to herein after as a gastroscope, or other type of flexible endoscope having a shaft 14a coupled to the accessory tube, and a suturing instrument 16. The suturing instrument 16 may be inserted in the accessory tube 12 as shown in FIG. 1, and is removable from the accessory tube 12 as shown in FIG. 2. The accessory tube 12 has access tubing 18 which is sufficiently flexible to be movable with the flexible shaft 14a of the gastroscope. Tubing 18 is braid reinforced with a braid of stainless steel, nylon, or Kevlar, to maintain the integrity of the tubing's circular cross-sectional shape and avoid kinking as the shaft 14a of the gastroscope bends when placed through the mouth into the gastrointestinal tract of a patient. The braiding may be located between two layers of tubing 18, which are integrated with the braiding during their extrusion forming tubing 18. For example, the outer diameter of tubing 18 may be 0.263 inches, while the internal diameter of tubing 18 may be 0.231 inches, and is such that a tissue engaging end 16a coupled to shaft 16b of suturing instrument 16 can pass through the tubing. Tubing 18 may be composed of pebax, polyurethane, or other flexible plastics of medical grade. The accessory tube 12 further has a cannula 20 attached to tubing 18 through which instruments, such as suturing instrument 16, may pass. Cannula 20 is describe is more detail later in connection with FIGS. 6 and 7. Accessory tube 12 is shown as a separate component in FIG. 2.

Figure 3:
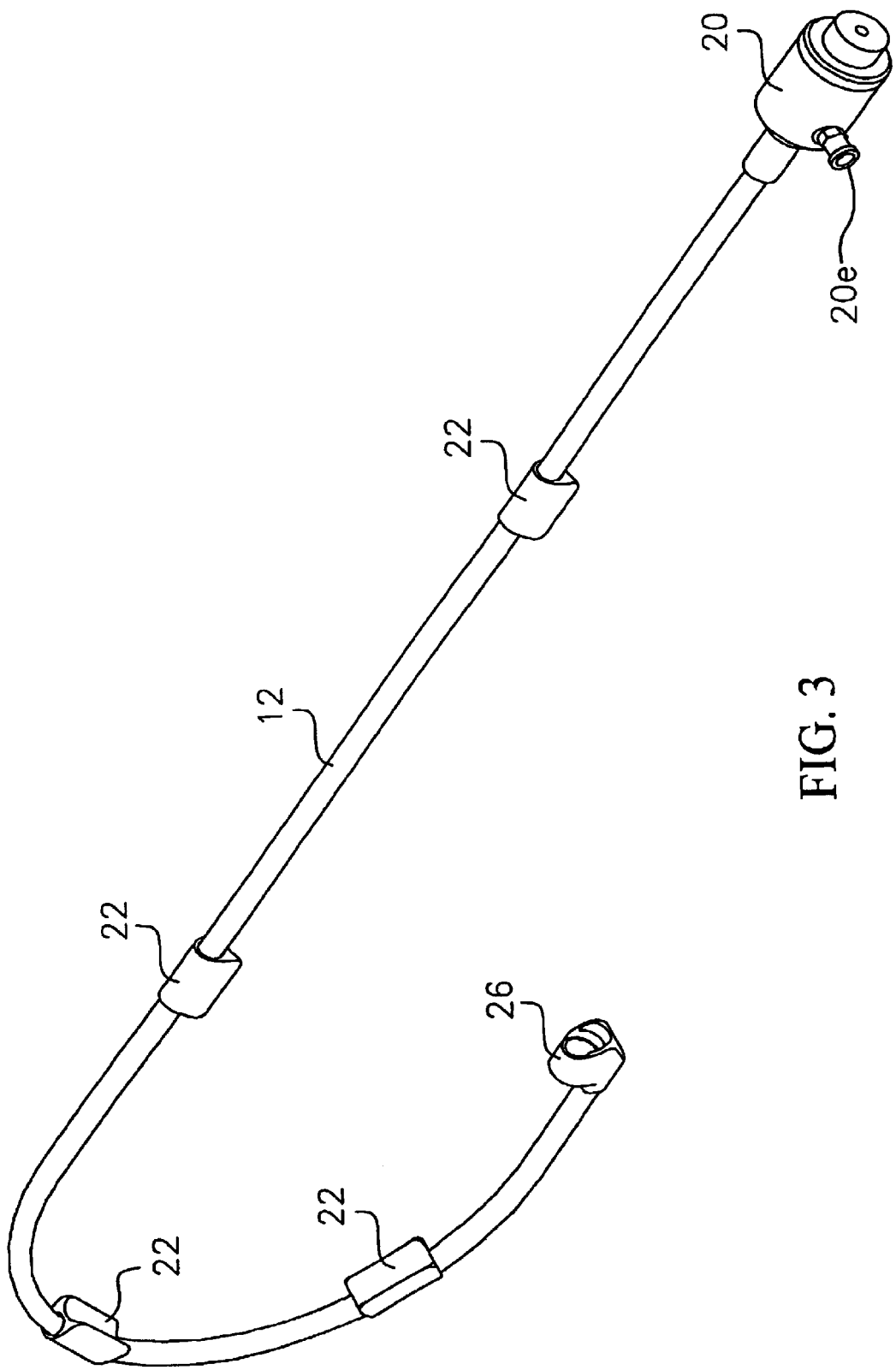
FIG. 3 is a perspective view of the accessory tube, cannula, attachment tip and tube guides of FIGS. 1 and 2.
Figure 4:
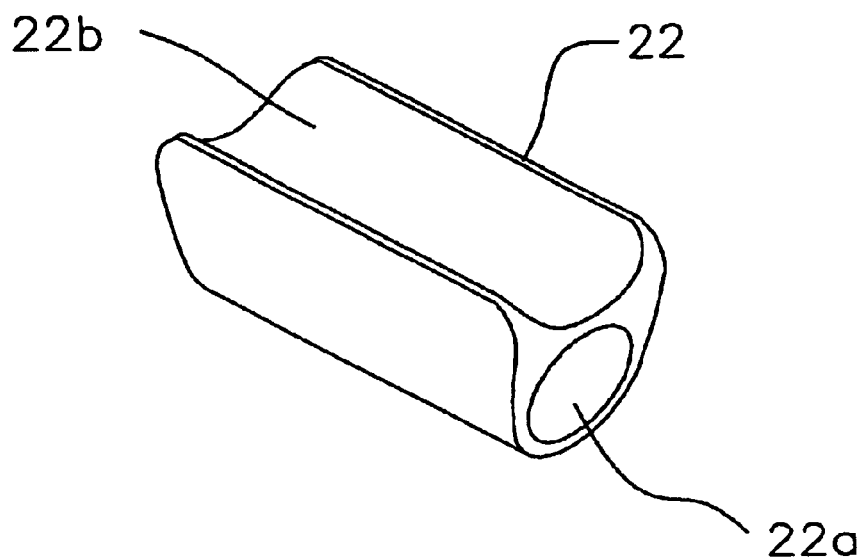
FIG. 4 is a perspective view of the tube guide of FIG. 3.
Figure 4A:
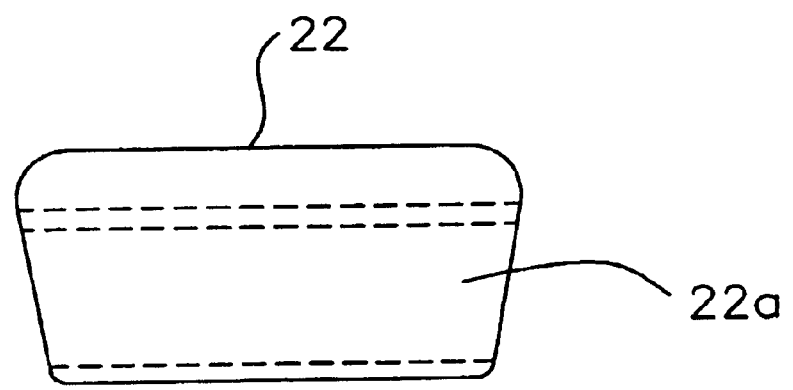
FIG. 4A is a side view of the tube guide of FIG. 4.

Multiple tube guides 22 couple tubing 18 to shaft 14a of gastroscope 14. Each tube guide 22 has an opening 22a extending through the tube guide and a curved surface 22b along its length which abuts the outer curved surface of shaft 14a, as shown in FIG. 1A. FIGS. 4 and 4A show the tube guide 22 in more detail. Tube guides 22 may be attached to shaft 14a by a band of tape 24 having an adhesive layer to fix the tube guide to shaft 14a. Other attaching means are also be used, such as glue. The diameter of opening 22a is slightly larger than the outer diameter of tubing 18 such that the tubing 18 is slidable through opening 22a to enable the accessory tube 12 to move in concert with flexing, bending, rotation, or other movements of the gastroscope 14. Tube guides 22 maintain tubing 18 substantial coaxial with shaft 14a of gastroscope 14. Preferably, four tube guides are provided as shown in FIGS. 1, 2, and 3, but other number of tube guides may be used.

Figure 5:
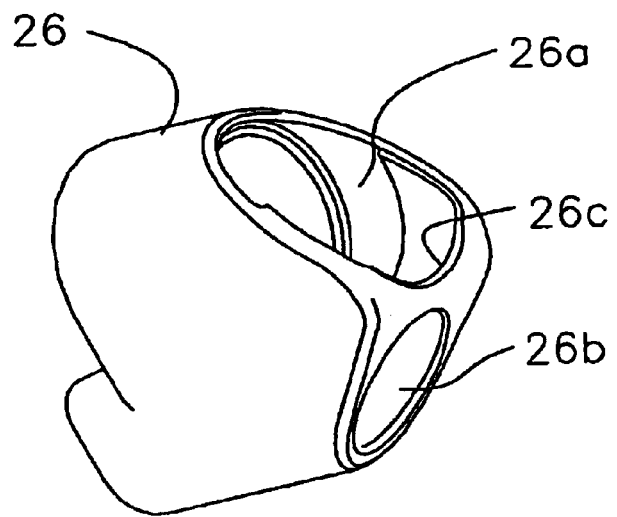
FIGS. 5 and 5A are front and back perspective views, respectively, of the attachment tip of FIG. 3.
Figure 5A:
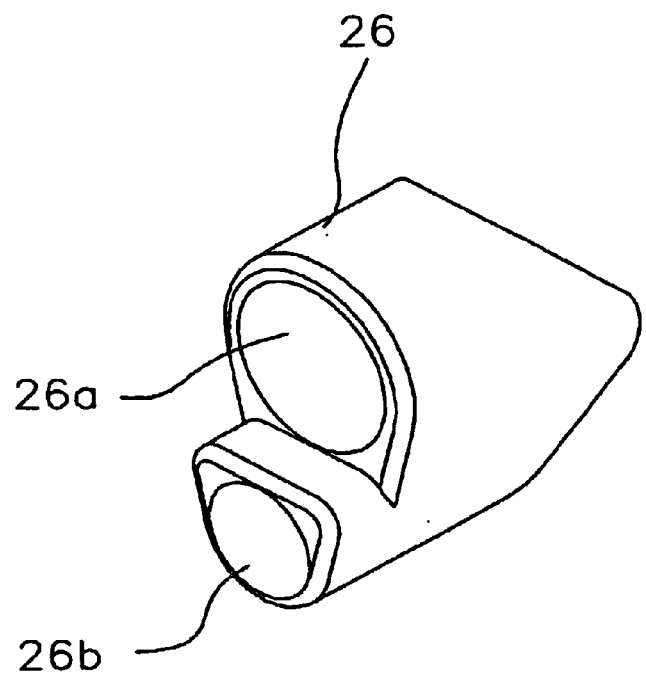

At the distal end of accessory tube 12 is an attachment tip 26 having two openings 26a and 26b to receive one end of tubing 18, and the distal end 14b of gastroscope 14, respectively. Attachment tip 26 is shown in more detail in FIG. 1B, and as a separate component in FIGS. 5 and 5A. Tubing 18 is attached to attachment tip 26, such as by glue or insert molding, while the gastroscope's distal end 14a is held by friction and seats in a shelf or lip 26c (FIG. 5) which forms a stop limiting forward movement of distal end 14a. The attachment tip 26 may be made of urethane or other molded plastic material. The length of the accessory tube 12 from its cannula 20 to attachment tip 26 may be, for example, 30 inches, but also may be of other lengths. Gastroscope 14 may be any typical gastroscope, such as that manufactured by Olympus, Inc., Pendax, Inc., Vision-Sciences, or Welch Allyn. For purposes of illustration, gastroscope 14 has at its upper end 14c a handle 27a, two dials 27b to steer the gastroscope, and various buttons/knobs to control typical gastroscope operation. The distal end 14b of the gastroscope has elements for imaging optics 28a, illumination 28b, water for cleaning imaging optics 28c, and a biopsy or working channel 28d representing tubing in communication with a port 27c at upper end 14c. A video display system 193 (FIG. 29B) is coupled to upper end 14a, via a cable 27d, to allow viewing of tissue from its distal end 14b on a display via optics 28a. Although a gastroscope is referred to herein, any other flexible endoscope may similarly be used. FIGS. 2 and 2A illustrate the accessory tube 12 and gastroscope 14 when no instrument is located in the accessory tube.

Figure 7:
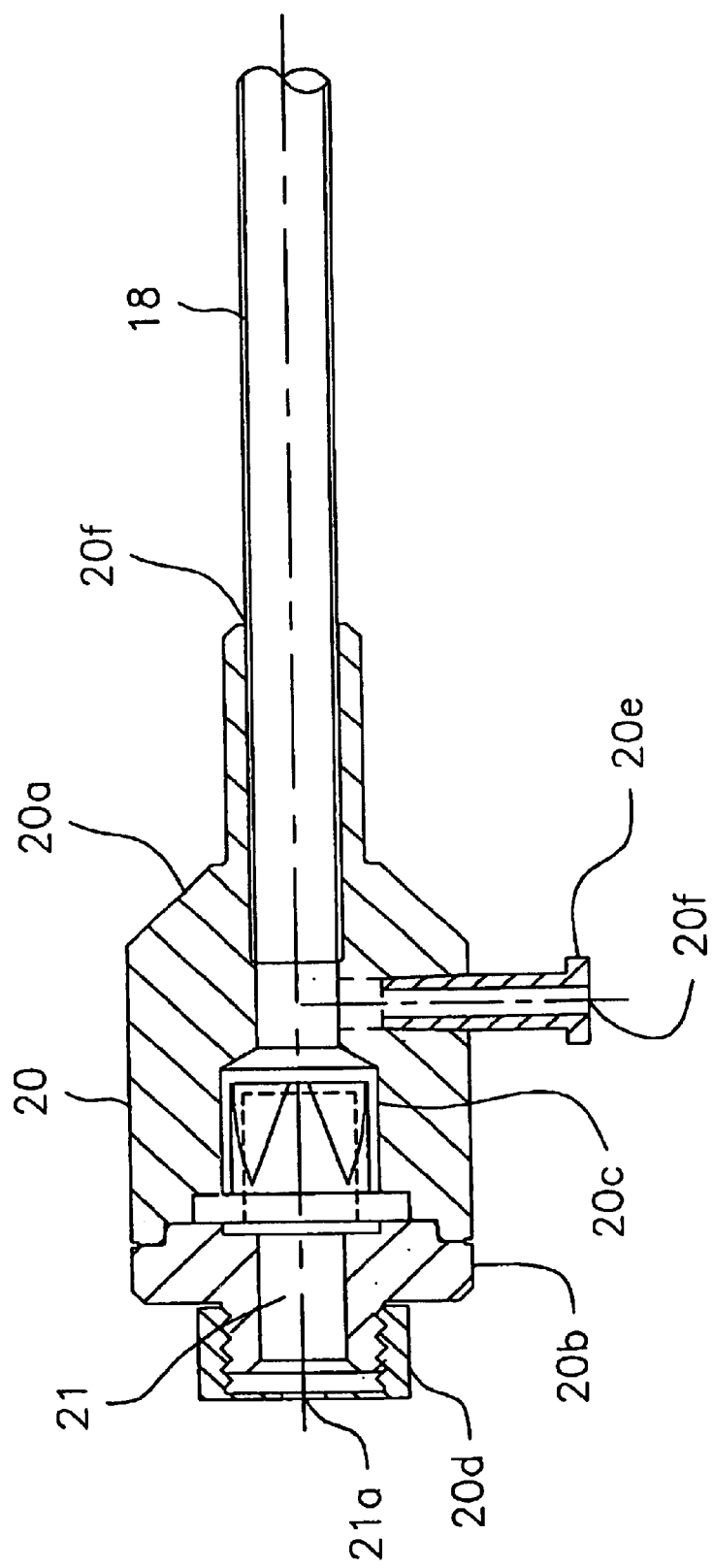
FIG. 7 is cross-sectional view of the cannula along lines 7—7 of FIG. 6.

Cannula 20 may be a typical type of cannula providing a sealable passage to tubing 18. For purposes of illustration, cannula 20 is shown in FIGS. 1–3, and in more detail in FIGS. 6 and 7. Cannula 20 has a housing 20a and a cap 20b which is received in housing 20a. Two seals 20c and 20d are provided in cannula 20 along a passage 21 from an opening 21a through which the shaft of an instrument may pass into tubing 18. Tubing 18 is received in an opening 20f which extends into housing 20a. Seal 20c may be a duck-bill seal as illustrated in FIG. 7. An optional auxiliary port 20e has a bore 20f which opens to passage 21 through which water, air, or vacuum may be provided through tubing 18. Although a cannula with two seals is described, the cannula may alternatively have a single seal. Seal 20d provides sealing about the shaft of an instrument, while seal 20c provides sealing when no instrument is located in the accessory tube 12.

The assembly of the gastroscope 14 and accessory tube 12 when in the gastrointestinal or gastroesophageal tract of a patient provides the feature of enabling instruments, such as the suturing instrument, and the later to be described suture securing instrument, to be insertable and retractable about the distal end of the gastroscope, without requiring removal of the gastroscope. Further, normal functionality of the gastroscope in viewing is provided without any partial obstruction or loss of use of the working channel 28d. An illustration of the system 10 in a patient's body is shown in FIGS. 29A–29F. As shown in FIG. 1B, tubing 18 may be of a larger diameter than working channel 28d.

Figure 8:
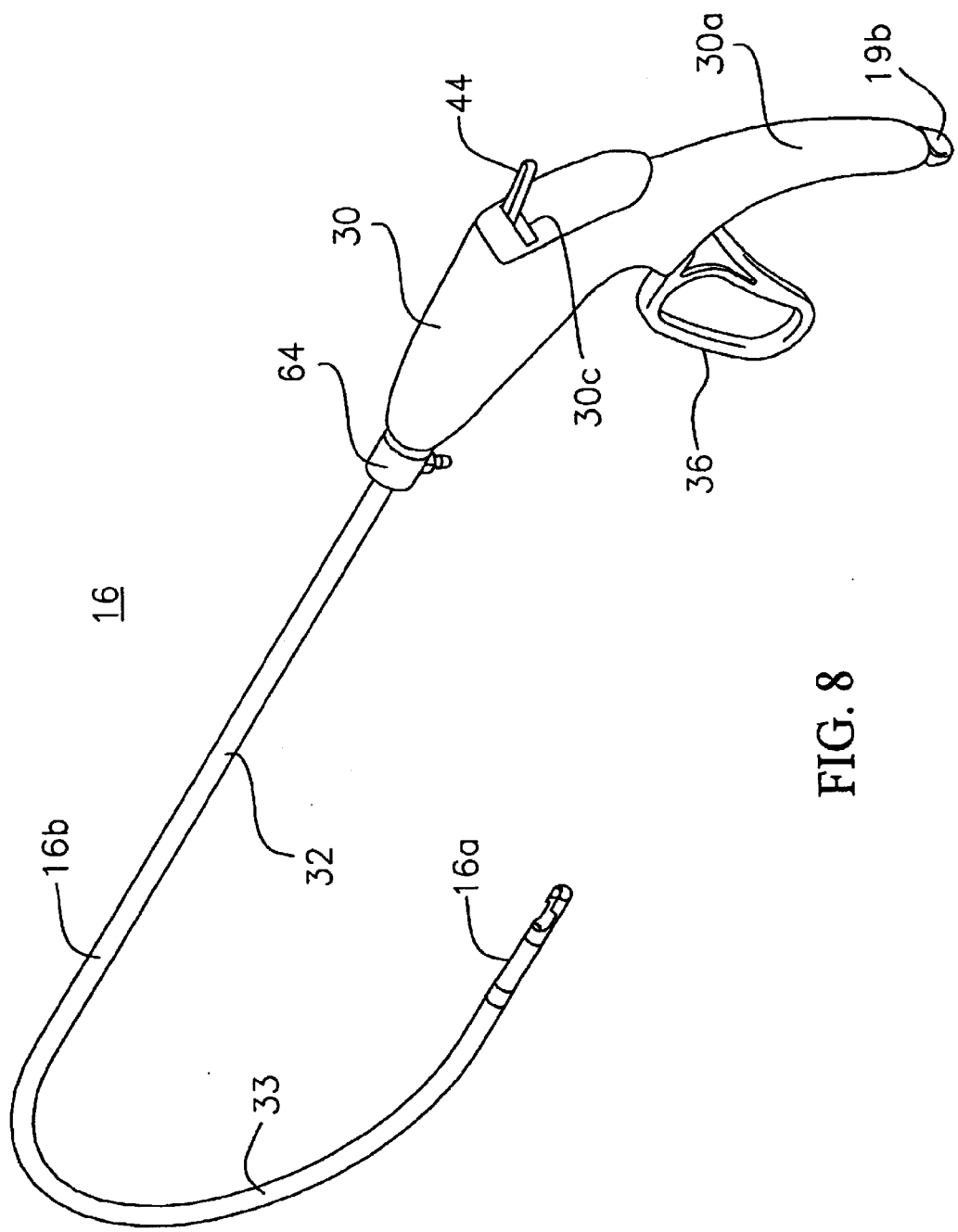
FIG. 8 is a perspective view of the suturing instrument of FIG. 1.
Figure 9:
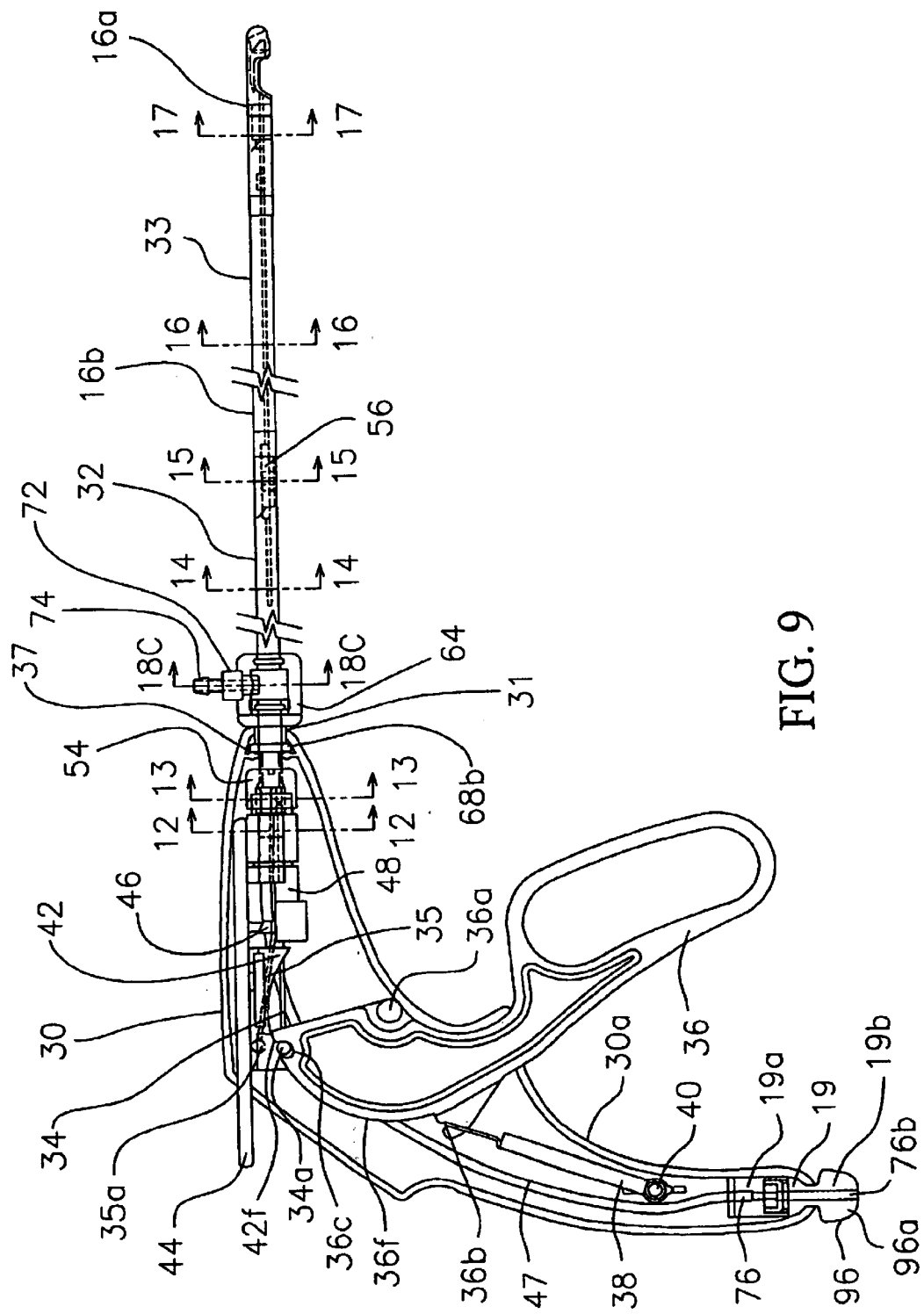
FIG. 9 is a side view of the suturing instrument of FIG. 1 in which the right cover of the housing of the instrument is removed.
Figure 10:
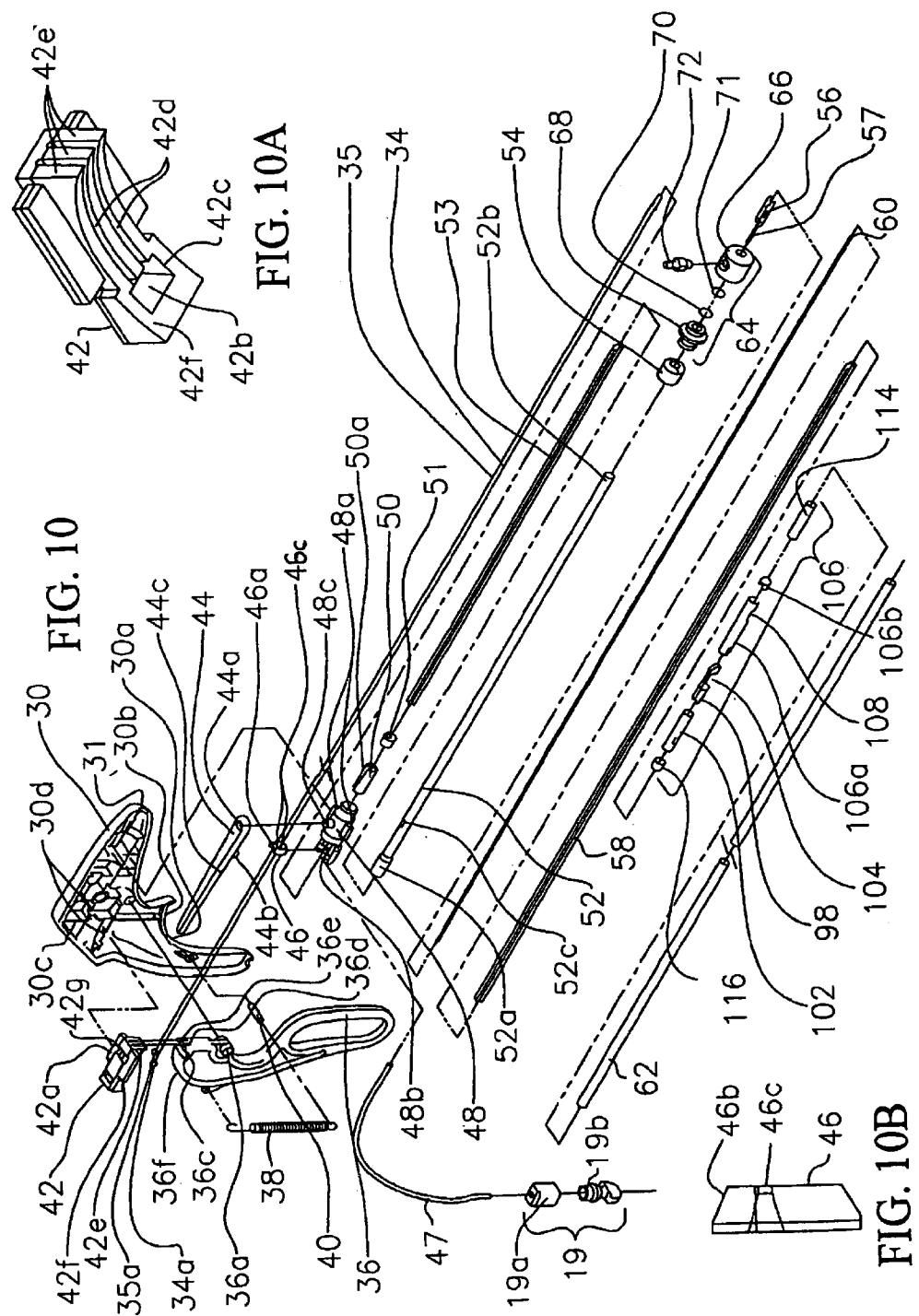
FIG. 10 is an exploded view of the suturing instrument of FIG. 1 in which the right cover of the housing is removed.

Referring to FIGS. 8–10, the suturing instrument 16 of system 10 is shown. Suturing instrument 16 represents the SEW-RIGHT® SR•5™ manufactured by LaserSurge, Inc. of Rochester, N.Y., which has been modified to have a longer and partially flexible shaft 16b extending from a housing 30, and means for selectably establishing suction to capture tissue at its tissue engaging end 16a. The tissue engaging end 16a and needles thereto may be similar to that shown in U.S. Pat. Nos. 5,431,666, 5,766,183, or European Patent No. EP 0669101, filed Feb. 23, 1995 and granted Oct. 14, 1998, which are herein incorporated by reference The shaft 16b represents an assembly of components 51–62 described below. Shaft 16b is rigid along a first section 32 when it extends from opening 31 in housing 30 and then is flexible along a second section 33 until coupling to the tissue engaging end 16a.

The housing 30 has a body shaped like a pistol having a handle portion 30a, and may be made of a two-piece construction of molded plastic. A pair of needles 34 and 35 extends from housing 30 through the shaft 16b into the tissue engaging end 16a. Each needle 34 and 35 has a non-tissue engaging end in the housing having a spherical member 34a and 35a, such as a ball or bearing, respectively, attached thereto. Both needles 34 and 35 and spherical members 34a and 35a may be a made of metal, such as surgical stainless steel. The spherical member 34a and 35a may have a bore into which the non-tissue engaging ends of the needles 34 and 35, respectively, extend and joined thereto, such as by welding or brazing.

The suturing instrument 16 includes an actuator member 36 representing a lever having two pins 36a extending into holes in the sides of housing 30 upon which the actuator member is pivotally mounted in the housing. Actuator member 36 has a portion which extends through an opening 30b (FIG. 10) in housing 30 to enable pivotal movement about pin 36a. An extension spring 38 is provided which hooks at one end in a notch 36b of actuator member 36 and is wound at the other end around a pin 40 located in holes in the sides of housing 30, such that the actuator member 36 is spring biased to retain actuator member 36 normally in a forward position, as shown for example in FIG. 9. The body of housing 30 has a front portion 31 (FIG. 10) providing a stop that limits the pivotal movement of the actuator member 36. A notch 36c is provided in the actuator member 36 which is shaped to received one of the non-engaging ends of needles 34 or 35, i.e., spherical members 34a or 35a, to be driven forward by an operator pulling actuator member 36 to pivot actuator member 36 towards handle portion 30a. Two grooves 36d (FIG. 10) are provided by three fingers 36e into which the needle 34 or 35 near the spherical members 34a or 35a, respectively, may lie.

A retainer member 42 is fixed in housing 30 by two flanges 42a above actuator member 36. As best shown in FIG. 10A, the retainer member 42 has a chamber 42b having a lower opening 42c to chamber 42b and two grooves 42d formed by fingers 42e which allow the spherical members 34a or 35a of needles 34 or 35, respectively, to be received in chamber 42b to restrict movement of the needle when held therein. The lower surface 42f of retainer member 42 is curved and faces correspondingly curved upper surface 36f of actuator member 36, such that the actuator member 36 is slidable along lower surface 42f responsive to the operator pulling the actuator member.

To select which of the needles 34 and 35 is to be driven by actuator member 36, the instrument 16 has a needle selection mechanism having a selector lever (or arm) 44 which is rotationally coupled with a cam member 46. The cam member 46 and selector lever 44 is supported by an adapter 48 in housing 30. Adapter 48 is mounted in housing 30 by two flanges 48a. The selector lever 44 is pivotally mounted by a pin 48c extending upwards from adapter 48 at a hole 44a through the lever. Selector lever 44 extends through an opening 30c in housing 30 and has a downwardly protruding member 44b which is received in a notch 46a of cam member 46 to rotate cam member 46 in a pocket 48b in the adapter 48 as the selector lever 44 is moved left or right. The cam member 46 may have a tapered surface 46b to facilitate its rotation in pocket 48b and two tapered apertures 46c through which needles 34 and 35 respectively extend, as shown in FIG. 10B. To select needle 34 to be driven, the selector 44 is moved right which rotates the cam member 46 to position needle 34 down and needle 35 up, such that end 34a is located in notch 36c and end 35a is located in chamber 42b of retainer member 42. To select needle 35 to be driven, the selector 44 is moved left which rotates the cam member 46 to position needle 34 up and needle 35 down, such that end 35a is located in notch 36c and end 34a is located in chamber 42b of retainer member 42.

The needle selector 44 may further have another downwardly protruding member 44c which rides in a slot 42g on the upper surface of retainer member 42. The slot 42g is contoured to have angled lower regions on either side of a raised region into which member 44c can be located to releasably lock to retain the position of lever 44 left or right.

The adapter 48 has a bore extending there through in which a needle spreader 50 is located. Needle spreader 50 has two channels 50b and 50c into which needles 34 and 35 are respectively located to increase the distance between the needles 34 and 35 as they extend toward cam member 46, such that the needles are properly aligned to apertures 46b in the cam member.

Figure 11:
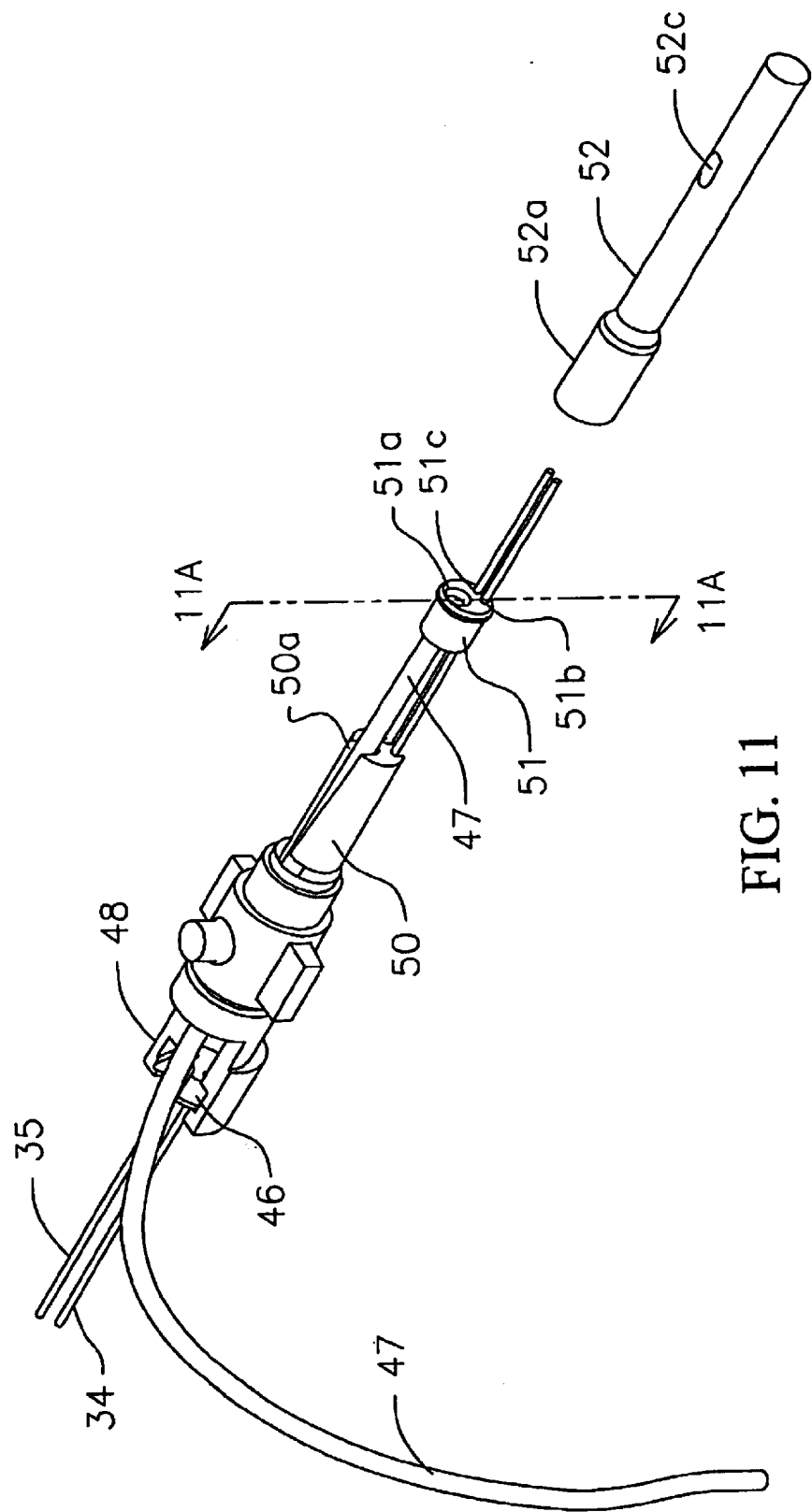
FIG. 11 is a partially exploded perspective view of the adapter, needle spreader, and gasket member of the suturing instrument of FIGS. 9 and 10.
Figure 12:
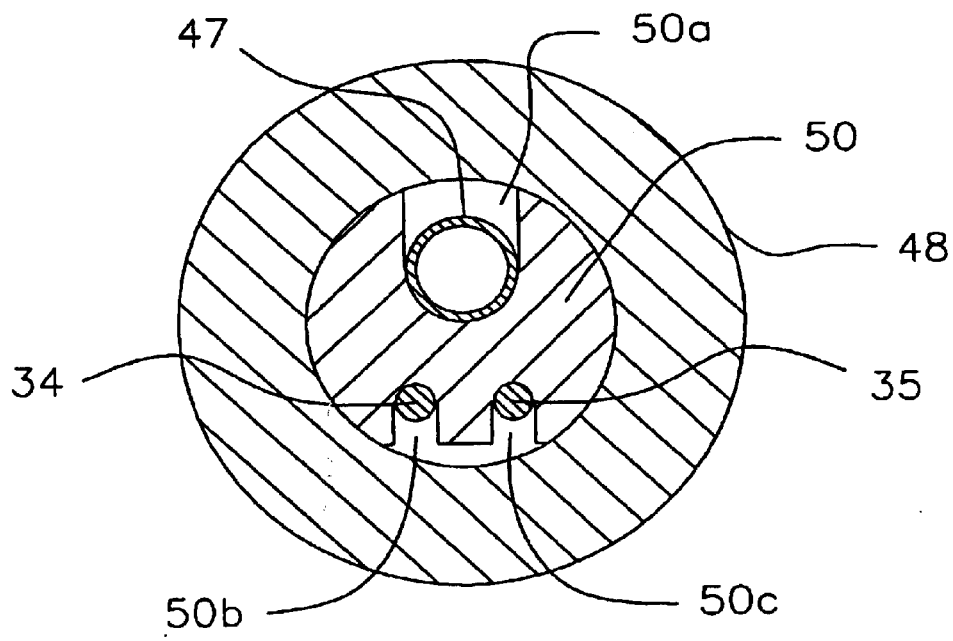
FIG. 12 is a cross-sectional view along lines 12—12 of the suturing instrument of FIG. 9.
Figure 13:
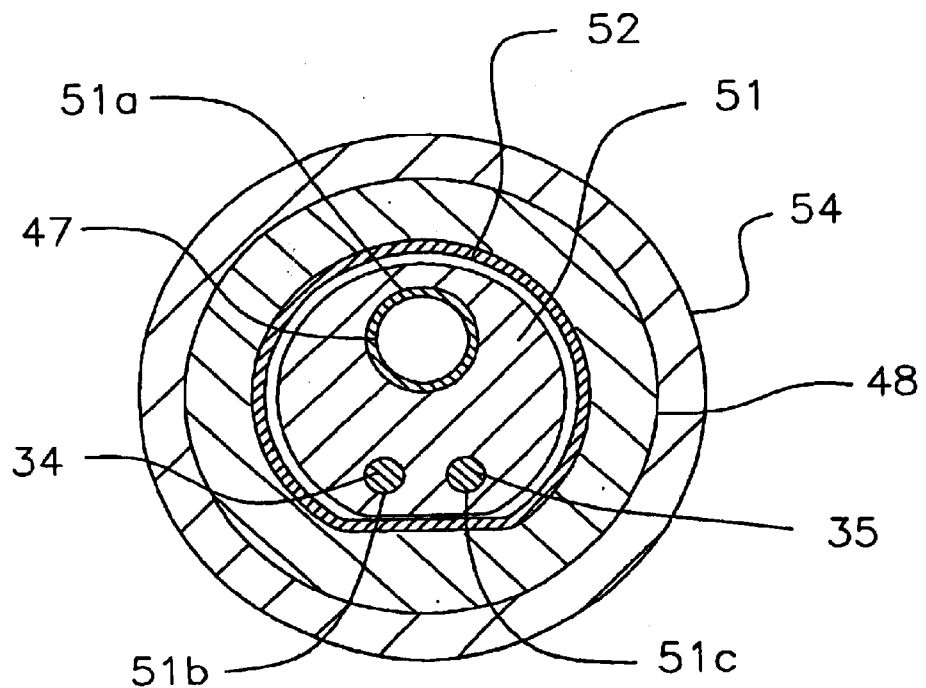
FIG. 13 is a cross-sectional view along lines 13—13 of the suturing instrument of FIG. 9.

A suture routing tube 47 is provided for suture thread in housing 30. Suture routing tube 47 has one end received in a valve assembly 19, described later below, at the bottom of handle 30a of housing 30 and then extends through notches 30d (FIG. 10) along the interior of the left side of housing 30, and a groove 50a along needle spreader 50 (FIGS. 10 and 11). A cross-section through needle spreader 50 and adapter 48 is shown in FIG. 12. The other end of the suture routing tube 47 is then mounted in a hole 51a through gasket member 51. Gasket member 51 further has two holes 51b and 51c through which needles 34 and 35, respectively, extend. A cross-section of shaft 16b through gasket member 51 is shown in FIG. 13. The gasket member 51 may be made of medical grade rubber, such as Santoprene.

Figure 11B:
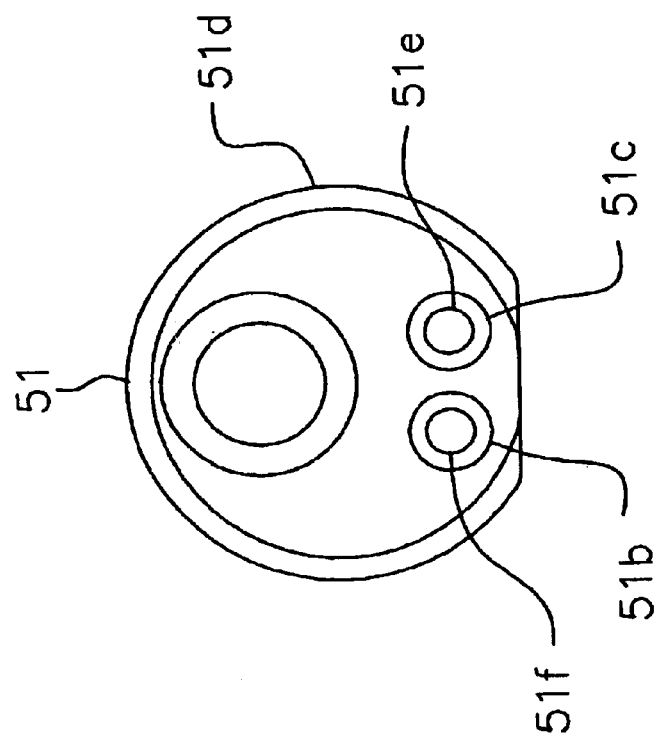
FIG. 11B is an end view of the gasket member of FIG. 11 without suture tube or needles.
Figure 11A:
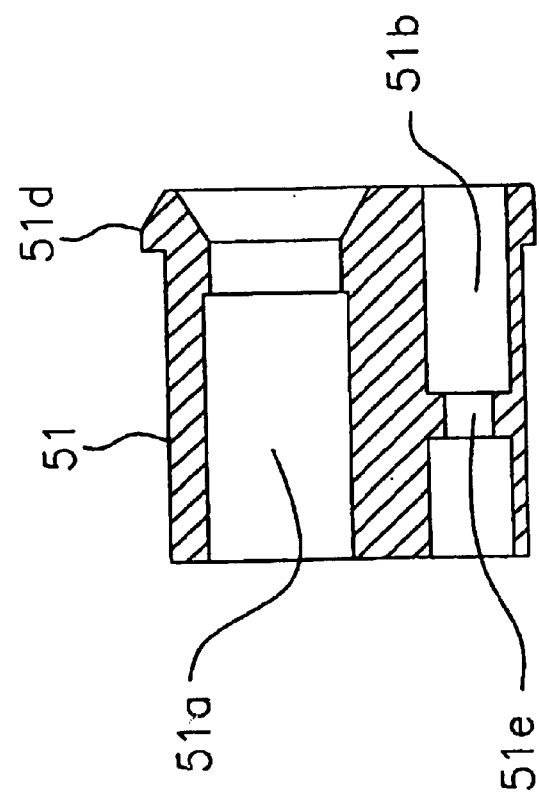
FIG. 11A is a cross-sectional view through lines 11A—11A of FIG. 11 showing the gasket member of the suturing instrument of FIG. 11 without the suture tube or needles.
Figure 14:
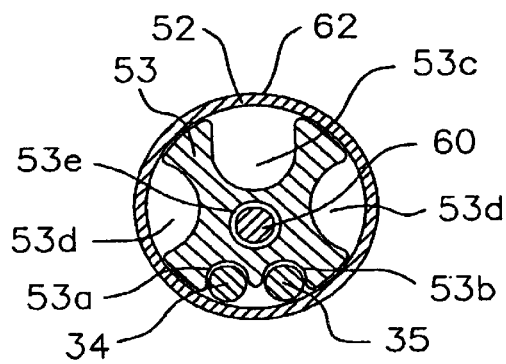
FIG. 14 is a cross-sectional view along lines 14—14 of the suturing instrument of FIG. 9.

A longitudinal guide member 53 is provided multiple tracks along its length, including two needle tracks 53a and 53b for needles 34 and 35, respectively, and a suture track 53c for suture thread extending from opening 51a of gasket member 51. A cross-sectional view of shaft 16b through guide member 53 is shown in FIG. 14. The guide member 53 may be made of extruded flexible material, such as Tecoflex®. A rigid tube 52 is provided which is D-shaped at one end 52a is registered into a corresponding shaped opening in adapter 48, and a threaded nut 54 having an opening which extends over mounting tube 52 and screws onto the end of the adapter 48 to secure tube 52 to housing 30. With the gasket member 51 loaded first into rigid tube 53, guide member 53 extends from the gasket member 51 through the rigid tube. In this manner, tracks 53a, 53b, and 53c each form a channel with the interior surface of rigid tube 52. Rigid tube 52 may be made of stainless steel, or other rigid material, and has for example, rigid tube 53 has an outside diameter of 0.205 inches. FIG. 11 shows the gasket member 51 prior to being positioned in abutment to needle spreader 50 and in end 52a of rigid tube 52. For inside rigid tube 52, gasket member 51 has a ring 51d which frictionally engages the interior surface of tube 52, hole 51a of the gasket member is of a diameter such that the suture tube 47 tightly fits therein and provides a seal around suture tube 47. The suture tube 47 may be held in place in hole 51a by friction, but adhesive may also be used. FIGS. 11A and 11B show gasket member 51 in more detail. Holes 51b and 51c are of a larger diameter than the needle, except for a small section of holes 51b and 51c where the diameter reduces to form flaps 5e and 51f, respectively of gasket material which seal around needles 34 and 35, respectively. This enables movement of the needles back and forth while maintaining a seal about each needle. One feature of the gasket member 51 is that it enables sealing the shaft 16b, such that negative pressure, i.e., suction, may be selectively applied down the shaft via a vacuum connection assembly 64, as described later below.

Figure 15:
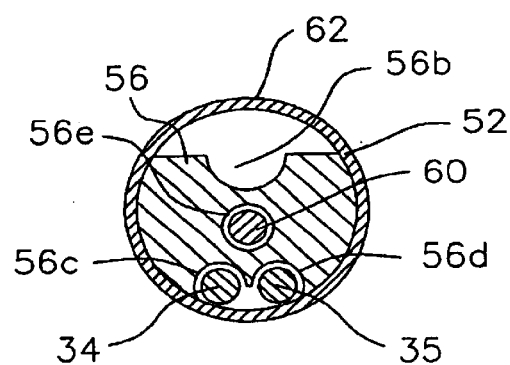
FIG. 15 is a cross-sectional view along lines 15—15 of the suturing instrument of FIG. 9.
Figure 16:
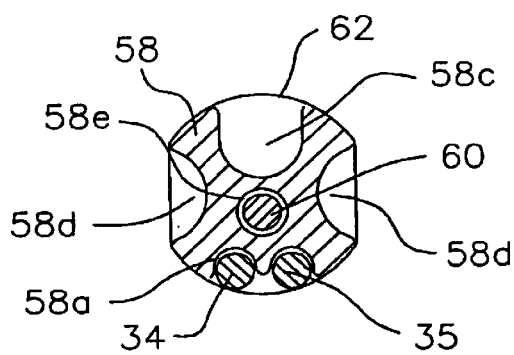
FIG. 16 is a cross-sectional view along lines 16—16 of the suturing instrument of FIG. 9.

At the other end 52b of rigid tube 52, a coupler member 56 is mounted in which two tabs 56a are received in two tracks 53d along two opposing sides of guide member 53. Coupler member 56 joins the non-flexible section 32 of the shaft 16b provided by rigid tube 52 with the flexible section 33 of the shaft 16b (FIG. 8). Coupler member 56 may be composed of stainless steel. A cross-section of shaft 16b through coupler member 56 is shown in FIG. 15. The coupler member has a track 56b for suture, tracks 56c and 56d for needles 34 and 35, respectively, and a central hole 56e. On the side of the coupler member 56 opposite guide member 53 is another longitudinal guide member 58 which extends through the flexible section of shaft 16b to the tissue engaging end 16a. Guide member 58, like guide member 53, is of an extruded flexible material, such as Tecoflex®. Guide member 58 has multiple tracks, including two needle tracks 58a and 58b for needles 34 and 35, respectively, and a suture track 58c for suture thread extending from track 56b of coupler member 56. A cross-sectional view of shaft 16b through guide member 58 is shown in FIG. 16. Two tabs 56f extend from the coupler member 56 into tracks 58d of guide member 58. A wire 60 extends from the tissue engaging end 16a through a central hole 58e of guide member 58 and the central hole 56e of coupler member 56, and then partly into a center hole 53e (FIG. 14) extending into guide member 53. The wire 60 extends partly through central hole 53e to facilitate registration of guide member 53 to coupler member 56 and guide member 58. The wire 60 is located in a central hole which extending into a sew tip 98 at the tissue engaging end 16a and attached thereto, such as by welding or brazing, passed through guide member 58 via hole 58e, and then extended through and in coupler member 56, where it is attached to the coupler member, via a tube coupler 57, such as by welding or brazing. This assembly is described in more detail below in connection with FIG. 17C. With the rigid tube 52, gasket 51, guide members 53 and 58 and central wire 60 in place, a plastic shrink wrap layer or tubing 62 is installed along shaft 16b from the vacuum connection assembly 64 until the tissue engaging end 16a, and shrunk in response to applied heat onto exposed surfaces of shaft 16b. About guide member 58, tracks 58a, 58b, and 58c each form a channel with the interior surface of shrink wrap layer 62.

Figure 17:
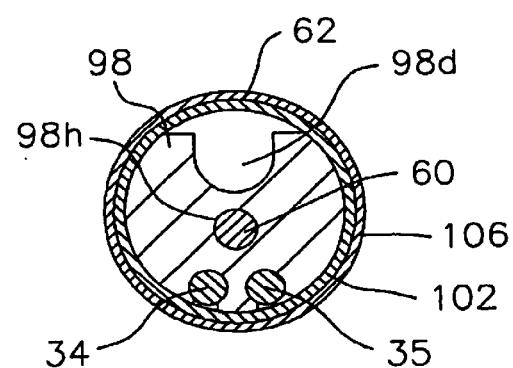
FIG. 17 is a cross-sectional view along lines 17—17 of the suturing instrument of FIG. 9.
Figure 17A:
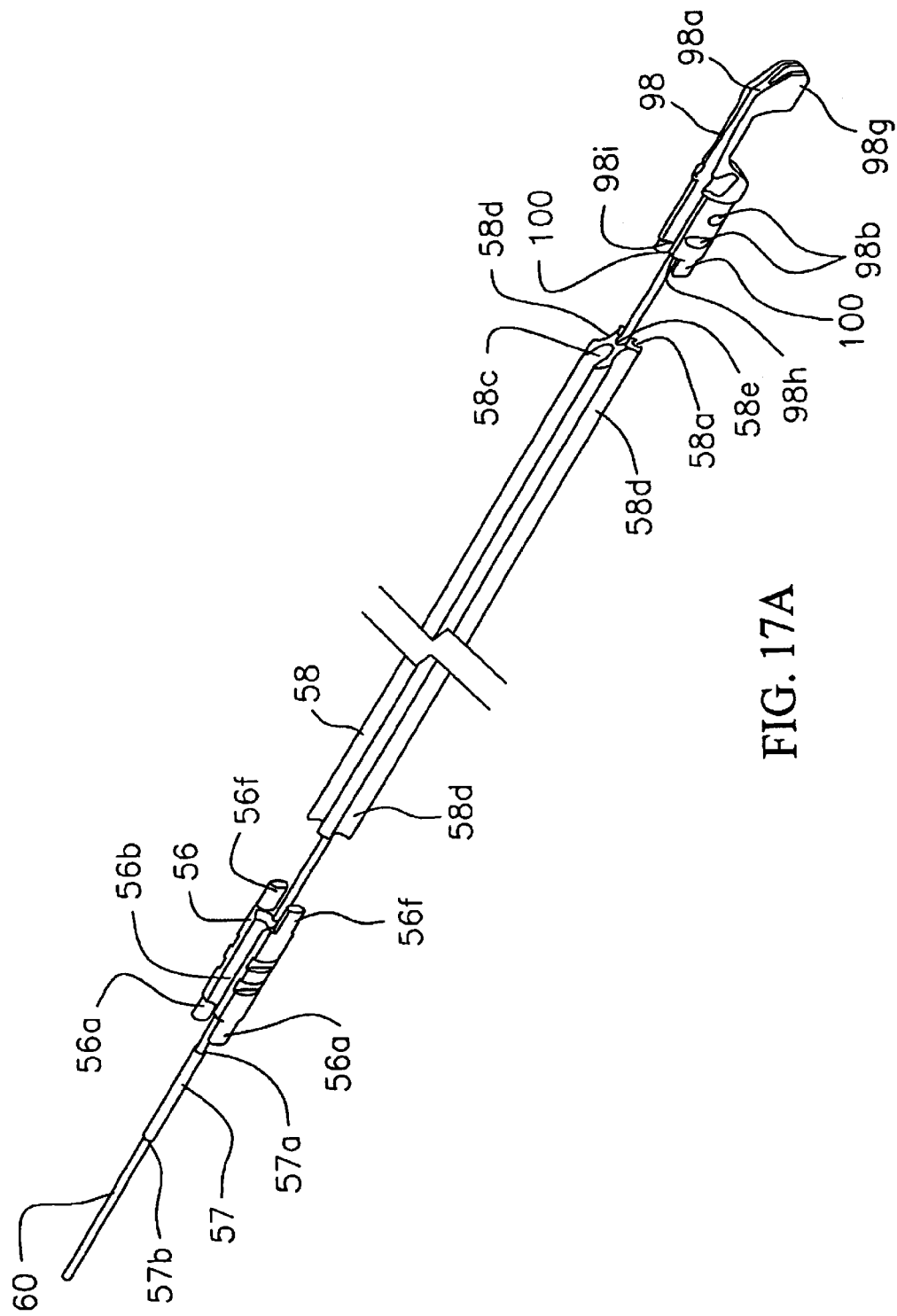
FIG. 17A is an exploded view of the coupler member, sew tip, and the guide member between the coupler member and sew tip, of the suturing instrument of FIGS. 9 and 10.

The connection of coupler member 56, guide member 58 and a sew tip 98 of the tissue engaging end 16a is best illustrated in FIGS. 17A and 17B in which tabs 56f of coupler member 56 are received in tracks 58d at one end of guide member 58, and tabs 100 from sew tip 98 are received in tracks 58d at the other end of guide member 58. Wire 60 extends through coupler member 56, guide member 58 into a hole 98*h* extends into the rear section 98*i* of the sew tip 98 (FIG. 21B). The guide member 58 with the shrink wrap enables the flexible section 33 of shaft 16*b* to bend and flex while maintaining the channels extending there through, while the wire 60 provide longitudinal support to the flexible section as it is attached to non-flexible section 30 at coupler member and the sew tip. Further, needles 34 and 35 are sufficiently flexible to bend without deformation within guide member 58. In order to translate rotational motion from the non-flexible section, tabs 56*a* and 56*f* of coupler member are registered into tracks 53*d* and 58*d* of guide members 53 and 58, respectively, and then tracks 58*d* of guide member 58 into tabs 100 of sew tip 98. Thus rotation occurring at the non-flexible section, such as by rotation of housing 30, is translated to tissue engaging end 16*a*.

FIG. 17C shows the attachment of wire 60, coupler member 56, and flexible section 33 of instrument 16 in more detail, such that possible damage to guide members from the heat of welding or brazing of metal components is avoided. The coupler member 56 has a recessed circular opening 56*h* to central hole 56*e* at the end 56*g* of coupler member 56 into which one end 57*a* of a wire coupler tube 57 is located. Wire coupler 57 represents a metal tube having an outer diameter sized to be received in recessed opening 56*h* and an inner diameter sized to receive there through wire 60. Prior to attachment of coupler member 56 to guide member 53, wire coupler 57 is first attached to coupler member 56, such as by welding or brazing, about recessed opening 56*h* prior to the assembly of the flexible section 33 components, i.e., sew tip 98, and guide member 58, to coupler member 56. Next, wire 60, which has not yet been passed through coupler member 56, is attached, such as by welding or brazing, into hole 98*h* (FIG. 21B) of sew tip 98. Wire 60 is then slid through central hole 58*e* of guide member 58 and hole 56*e* of coupler member 56, and the sew tip 98 at two tabs 100 frictionally engages into two tracks 58*d* of guide member 58 at one end of guide member 58. At the other end of guide member 58, tabs 56*e* of coupler member 56 frictionally engages into tracks 58*d*. With the coupler member 56 integrated with guide member 58, wire 60 is attached at end 57*b* of wire coupler 57, such as by welding or brazing, which integrates the assembly of coupler member 56 with flexible section 33 of the instrument 16, as shown in FIG. 17B. Thereafter, the coupler member 56 at its tabs 56*f* frictionally engages into tracks 53*d* of guide member 53, such that wire 60 partly extends into central hole 53*e* of guide member 53. The guide member 53 and coupler member 56 of the assembly are received into the rigid tube 52, such that guide member 53 abuts gasket 51, and coupler member is attached to rigid tube by mechanical fastening by forming small dents in the metal of the tube 52 with a press into recessed four pockets 56*i* (FIG. 17A), i.e., two on each side of the coupler member 56.

Figure 18:
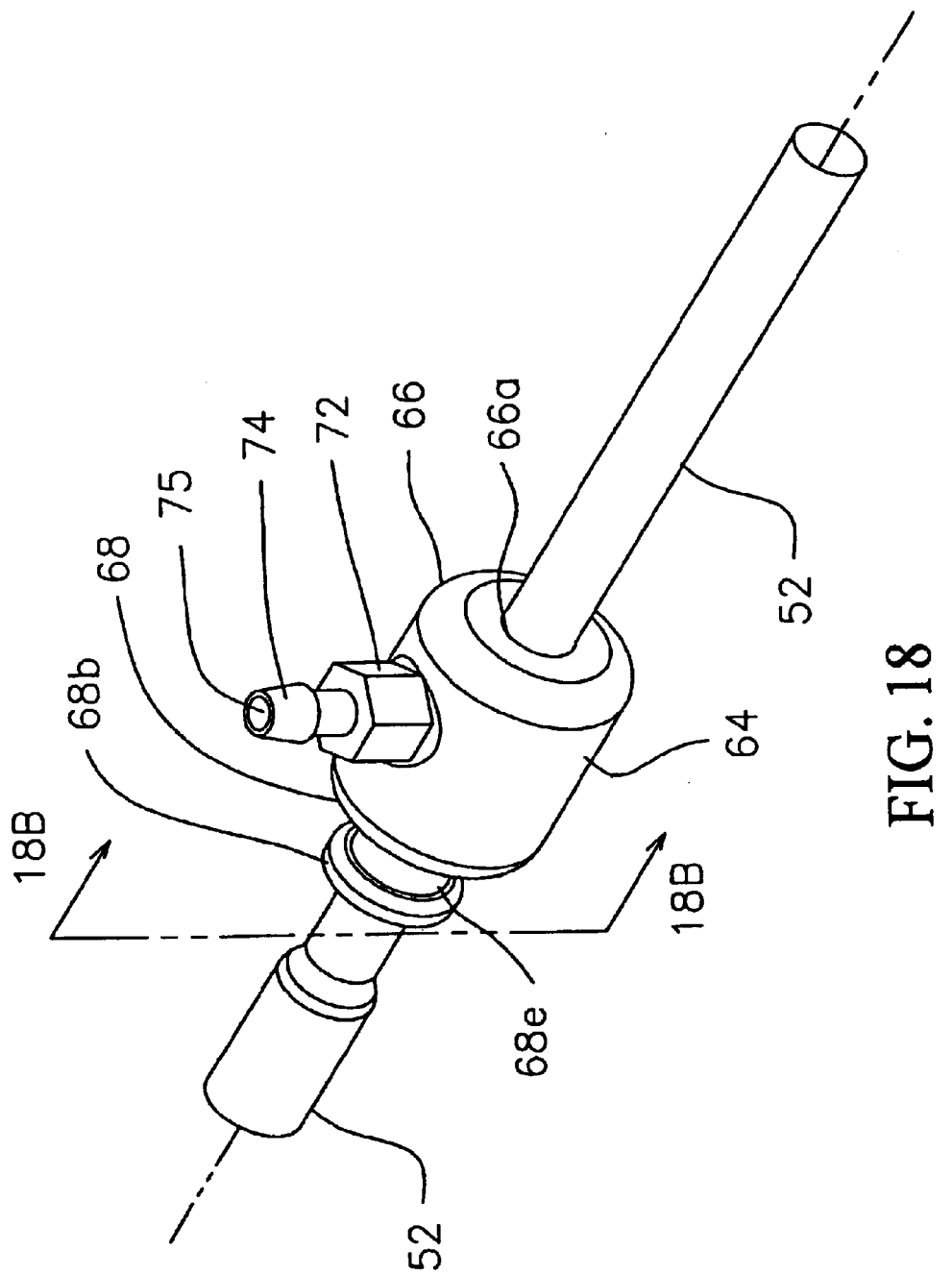
FIG. 18 is a perspective view of the vacuum connection assembly of the suturing instrument of FIGS. 9 and 10 for application of a vacuum or partial vacuum.
Figure 18A:
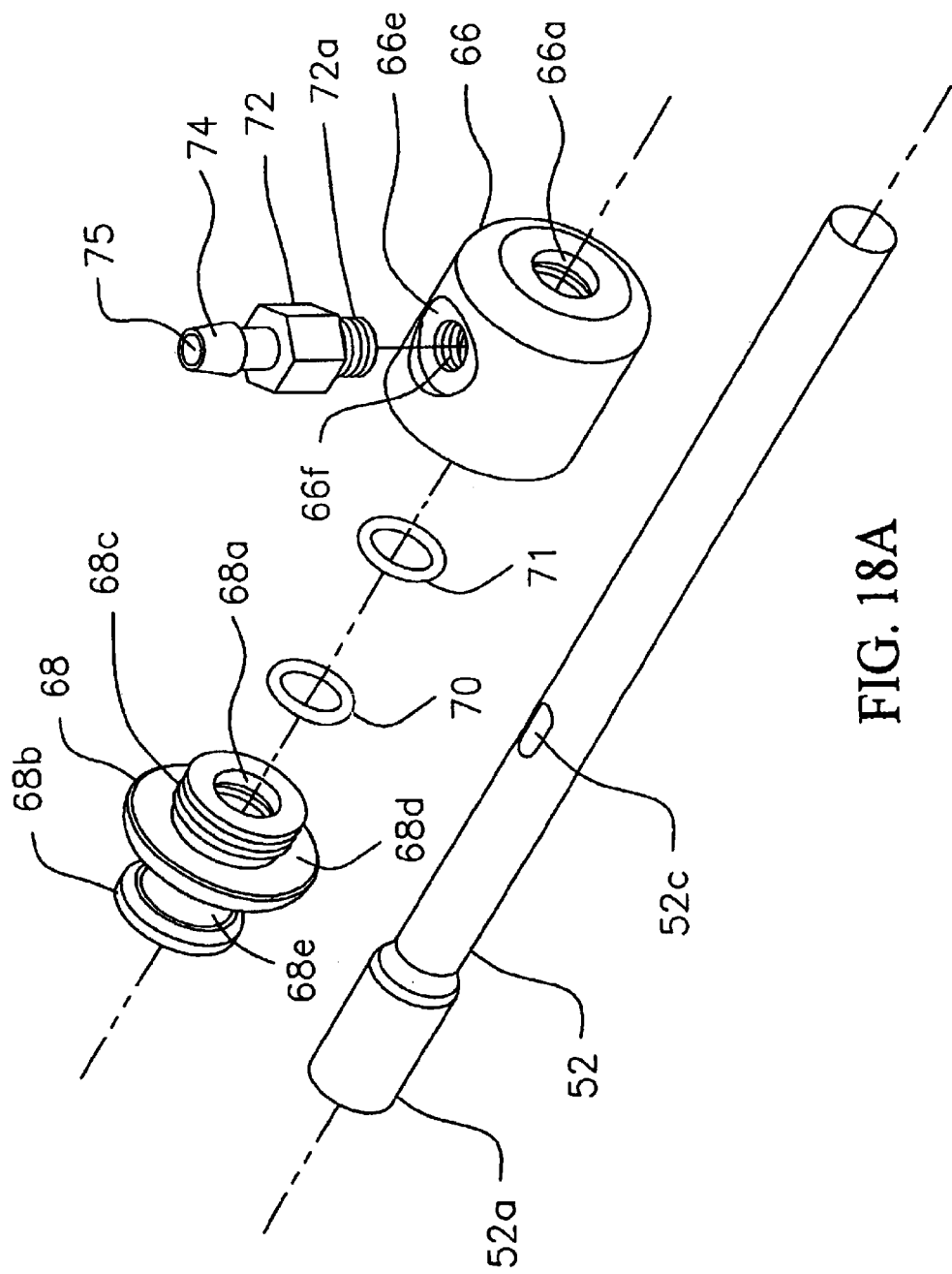
FIG. 18A is an exploded view of the vacuum connection assembly of FIG. 18.
Figure 18C:
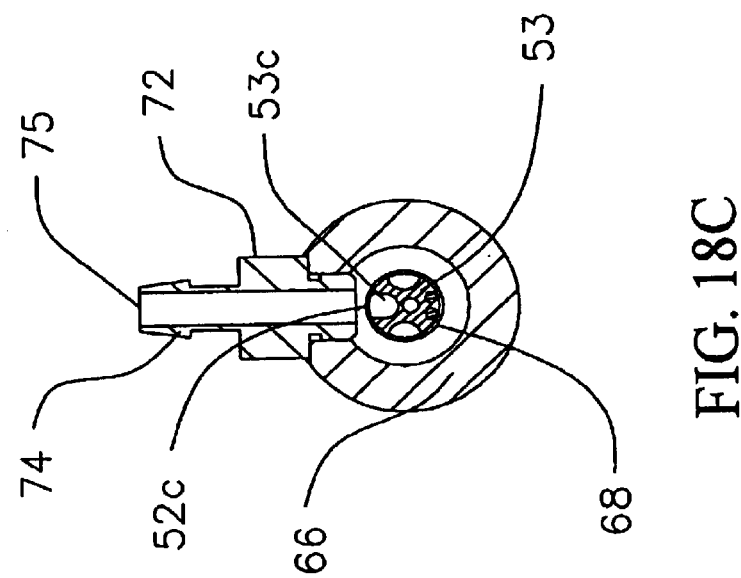
FIG. 18C is a cross-sectional view along lines 18C—18C of the suturing instrument of FIG. 9.
Figure 18B:
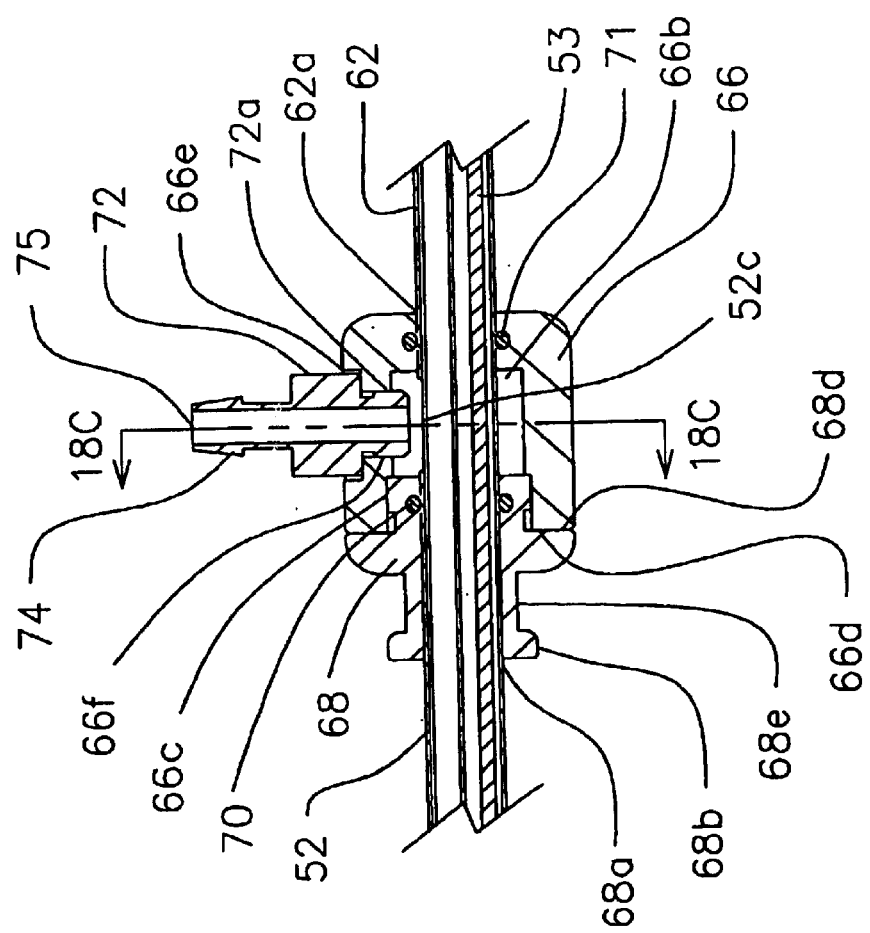
FIG. 18B is a cross-sectional view of the vacuum connection assembly along lines 18B—18B of FIG. 18.

Referring to FIGS. 18 and 18A–C, a vacuum connection assembly 64 for suturing instrument 16 is shown. Vacuum connection assembly 64 includes a front housing member 66 which has a circular opening 66*a* to an interior chamber 66*b*, and a rear housing member 68 having a circular opening 68*a* extending there through. Rear housing member 68 has a first extension toward housing 30 providing a shaft 68*e* having an annular flange 68*b* and a second extension toward front housing member 66 providing a threaded shaft 68*c*. Shaft 68*c* is screwed in a threaded opening 66*c* (FIG. 18B) to chamber 66*b* of front housing member 66, whereby surface 68*d* of the rear housing member tightly fits (mates) along surface 68*d* of the front housing member 66. Circular opening 66*a* is coaxial with circular opening 68*a* through their respective housing members. A rubber O-ring 71 is provided in an annular groove in opening 66*a* of the front housing member 66, while another O-ring 70 is provided in an annular groove in opening 68*a* of rear housing member 68, as illustrated in FIG. 18B. A fitting member 72 is received in front member 66 in a recessed pocket 66*e* to a threaded opening 66*f* extending to chamber 66*b*, such that a port 74 is provided having a bore 75 to chamber 66*b*. Fitting member 72 is threaded along its surface 72*a* to enable the fitting member to screw into threaded opening 66*f* of front housing member 66. Except for O-rings 70 and 71, the components of vacuum connection assembly 64 may be made of stainless steel.

The vacuum connection assembly 64 is placed on rigid tube 52 so that the tube extends through openings 66*a* and 68*a*, O-rings 70 and 71, and chamber 66*b*, and an opening 52*c* in the rigid tube lies in chamber 66*b* and faces bore 75 of the fitting member. The diameter of apertures 66*a* and 68*b* are slightly larger than the outer diameter of rigid tube 52 about opening 52*c*. O-rings 70 and 71 engage the outer surface of rigid tube 52 to seal chamber 66*b*, but for bore 75 and opening 52*c* to suture track 53*c* (FIG. 18C). Flange 68*b* from rear housing member 68 is received in a pocket 37 (FIG. 9) formed when the left and right sides of housing 30 are mated to each other. A vacuum source may be applied via tubing (not shown) to port 74, such that negative air pressure is provided in chamber 66*b* which may be communicated via an opening 52*c* of rigid tube 52 along a suture channel formed by suture track 53*c* of guide member 53 to suture track 58*d* of guide member 58 through track 56*b* of coupler member 56, down to the tissue engaging end 16*a*. Vacuum connection assembly 64 may alternatively be coupled at port 74 to a source for air to provide positive air pressure along the same suture channel, i.e., to drive air down to the tissue engaging end 16*a*.

A valve 19 is provided at the bottom of handle 30*a*, as shown in FIGS. 9 and 10, having a valve seat 19*a* and a valve controller 19*b*, shown as separate components in FIGS. 19A and 19B. Valve seat 19*a* is composed of medical grade rubber, such as Santoprene®, and has a hole 76 extending into an interior chamber 78. One side 79 of this chamber 78 has a lip 80 about an opening 81. Protruding into the chamber 78 facing opening 81 is a raised member 82 of the valve seat 19*a* through which the hole 76 extends to an opening 84, which is recessed near a surface 82*a* of the raised member 82. The recess of opening 84 forms the shape of an eye having two opposing corners 86 when valve 19 is open. Two opposing fingers 88 of the raised member 82 extend from the top and bottom of the eye of opening 84. A valve controller 19*b* composed of molded plastic, or other rigid material, has a circular section 90 having an opening 92 to an interior surface forming a cam 94, and a recessed retainer ring 95. Circular section 90 is received through opening 81 such that retainer ring 90 is captured by lip 80 to retain valve controller 19*b* in valve seat 19*a*. Fingers 88 and corners 86 of the raised member 82 of the valve seat lie against the surface of cam 94 of the valve controller 19*b*. The cam surface is wider along one dimension and narrower along a perpendicular dimension, such that when the fingers 88 lie along the narrower dimension, they compress the recess of opening 84 into a closet slit to close valve 19, and when fingers 88 lie along the wider dimension, the recess of opening 84 returns to its normal shape and the valve 19 is open. Adjusting the dimensions of the cam surface 94*a* controls the amount of pressure applied to compress opening 84, and thus the integrity of the closed valve's seal. Another hole 76*b* (FIG. 9) extends through opening 92 to the bottom 96a of turn knob 96 of the valve controller. The suture routing tube 47 is received in hole 76 of valve seat 19a, as shown in FIG. 9, such that suture material from the tube can pass through openings 76 and 84 of the valve seat and then through hole 76b of the valve controller.

Figure 20C:
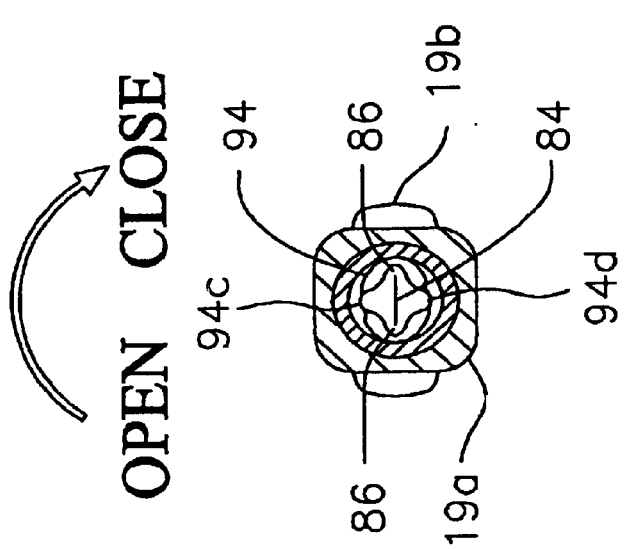
FIGS. 20A, 20B, and 20C illustrate the valve seat in response to the rotation of the valve knob from an open state to a closed state to seal one end of the suture tube of the suturing instrument of FIGS. 9 and 10.
Figure 20B:
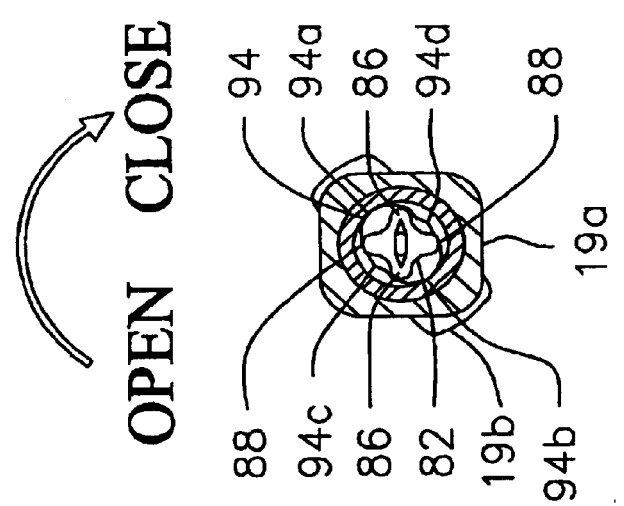
Figure 20A:
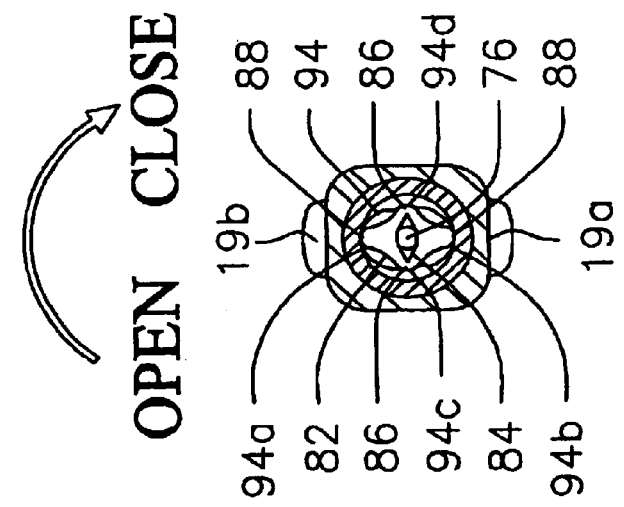

As shown in FIG. 20A, the valve 19 is open when the finger 88 align along surface 94a and 94b of the cam 94, and corners 86 are each received in corresponding detents 94c and 94d of cam 94. To close valve 19, a turn knob 96 of the valve controller 19b is rotated as shown in FIG. 20B. This starts compressing fingers 88 against the surface of the cam 94 until the fingers 88 lie in detents 94c and 94d compressing opening 84 of the valve seat to close the valve, as shown in FIG. 20C. To open the valve 19, the turn knob 96 is again rotated until the corners 86 lie in detents 94c and 94d. The turn knob 96 may be rotated clockwise or counterclockwise to open and close valve 19. Valve 19 may be closed to seal the suture tube 47 when suction is applied via vacuum connection assembly 64, but allows suture to be drawn under slight tension through the valve.

Other types of valve 19 may alternatively be used, such as shown in FIG. 19D, which provides a seal, but enables the suture to be drawn under slight tension through the valve. In FIG. 19C, the bottom of handle 30a is shown in which the suture tube 47 is received in a duckbill valve 128 providing a chamber 128a and two flaps 128b extending into the chamber along the length of suture 105 which extends through suture tube 47 between flaps 128b and through an opening 129 in housing 30. In response to negative air pressure in suture tube 47, the two flaps 128b meet along edges 128c providing a seal about the suture 105 in chamber 128a. FIG. 19C illustrates the valve when closed, when open flaps 128b at edges 128c may separate from each other.

Figure 21:
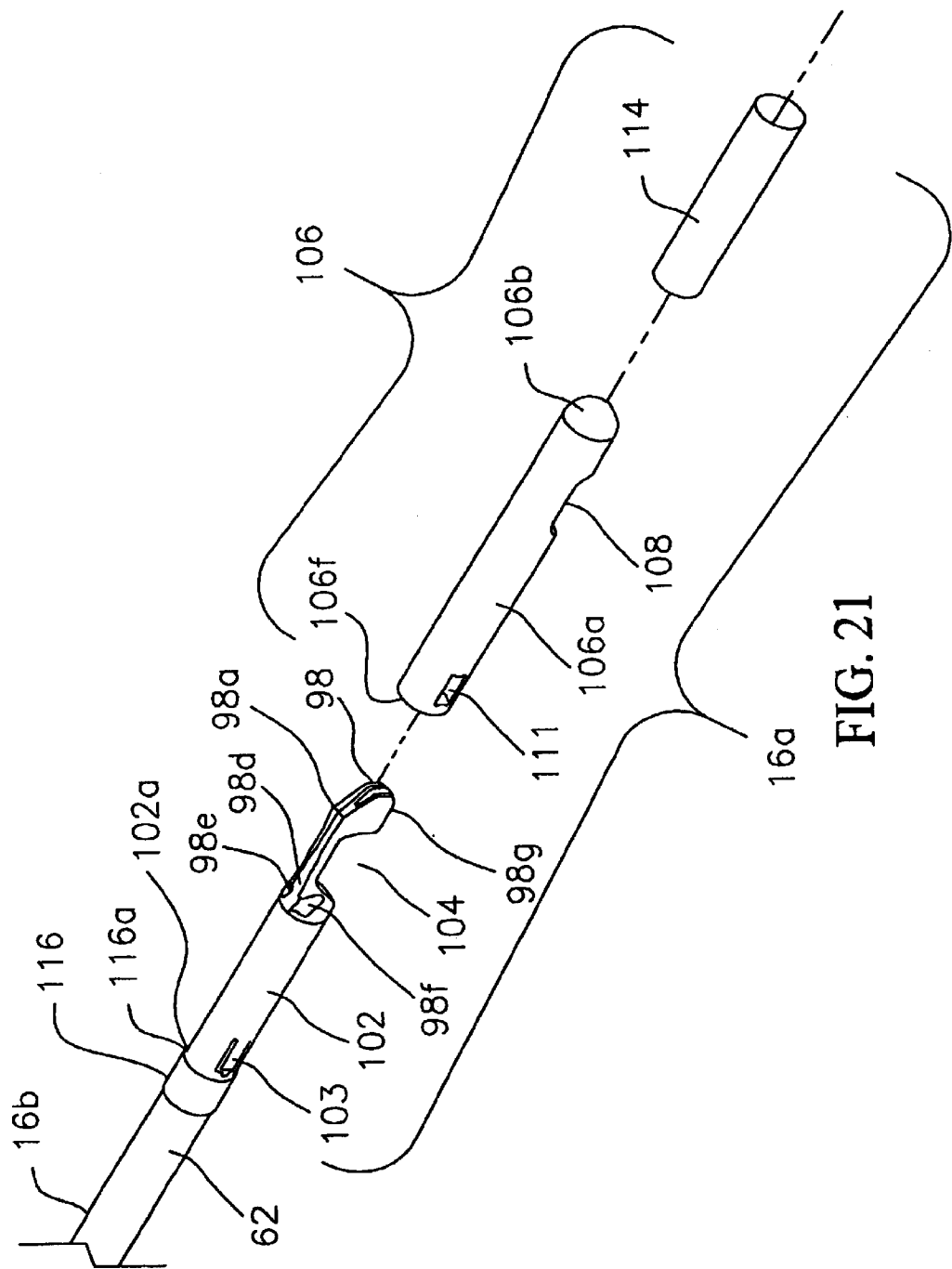
FIG. 21 is an exploded view of the distal end of the suturing instrument of FIG. 9.
Figure 21A:
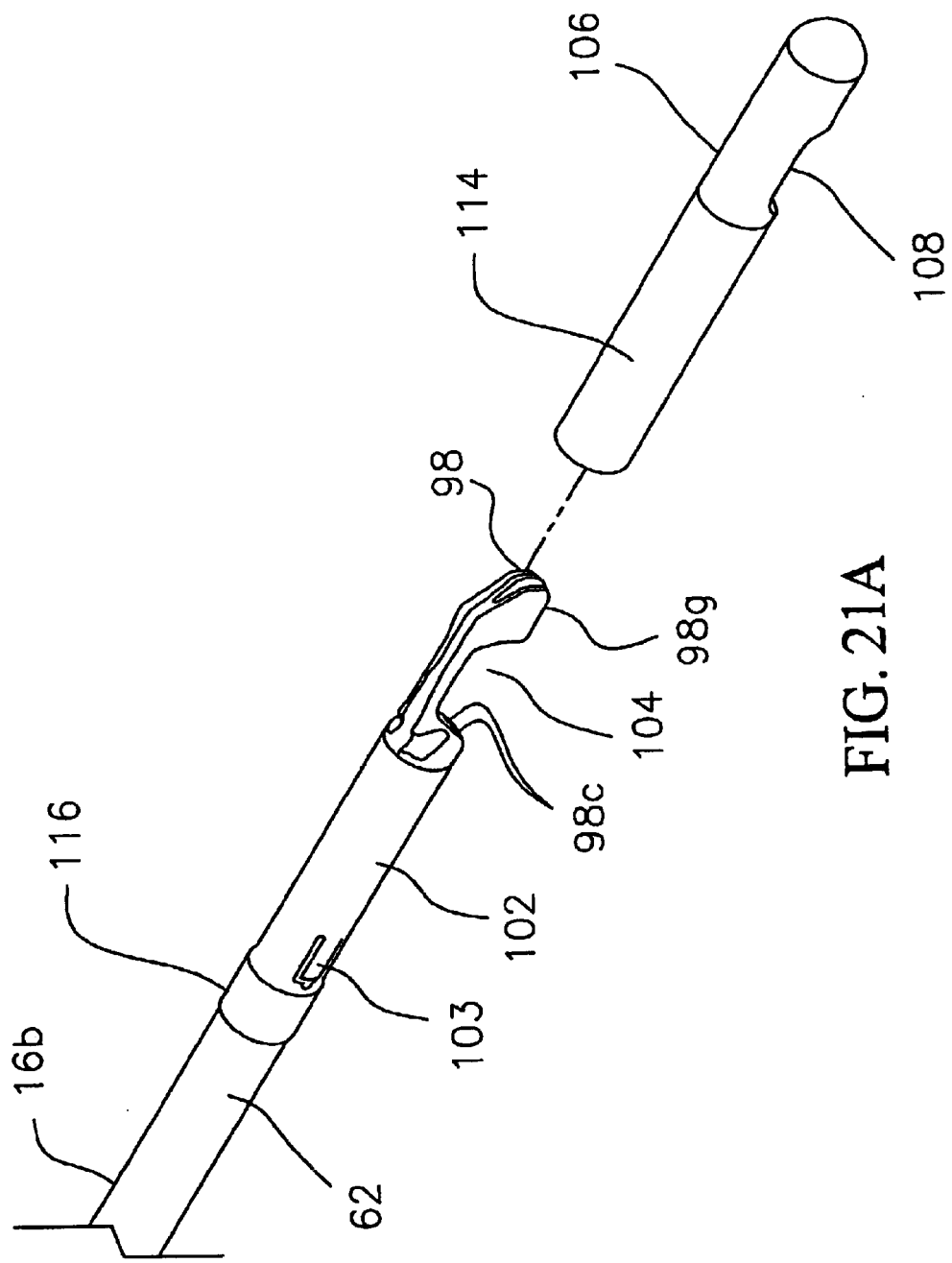
FIG. 21A is an exploded view of the distal end of the FIG. 9 showing the sleeve into which the tissue engaging end of the suturing instrument is received.
Figure 21B:
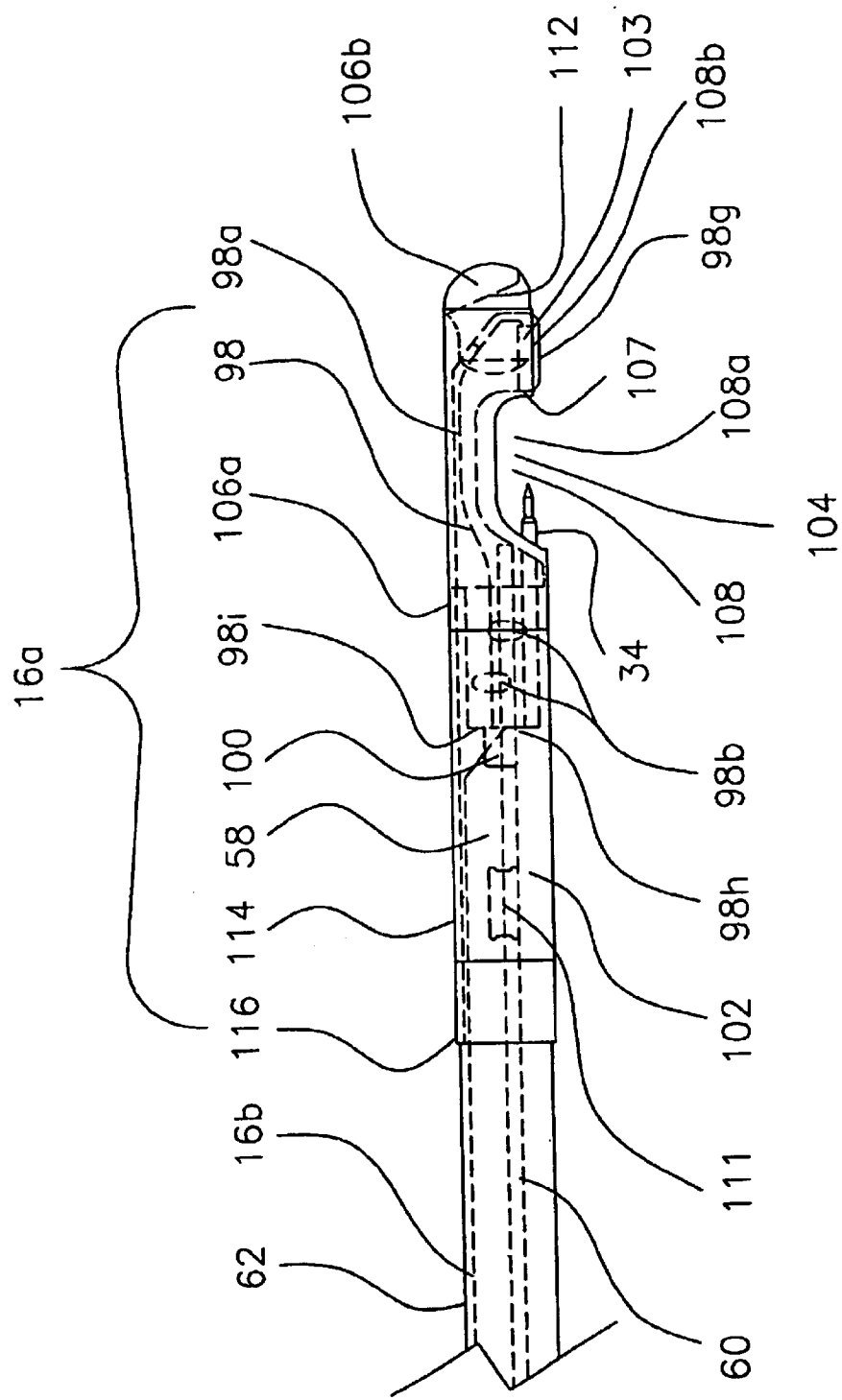
FIG. 21B is a side view of the tissue engaging end of the suturing instrument with the sleeve of FIGS. 21 and 21A.

Referring to FIGS. 21, 21A and 21B, the tissue engaging end 16a of the suturing instrument 16 is shown having the sew tip 98 which is mounted in a tip tube 102, such that the front section 98a of the sew tip extends from tube 102. The mounting of the tip tube 102 to the sew tip 98 may be achieved by mechanical fastening by forming small dents in the metal of the tip tube 102 with a press into recessed four pockets 98b, i.e., two on each side of the sew tip (FIG. 17A). The sew tip 98 has a gap 104 in a C-shaped jaw having two openings 98c at one side of the gap through which each of needles 34 and 35 may extend to capture ferrules 103 having one end of suture material 105 located in openings 107 at the other side of gap 104, and after each needle captures a ferrule, the needle retracts back into their respective opening 98c carrying the suture material on its tip. A channel 98d is provided in the sew tip which aligns with suture track 58c of guide member 58, as shown in FIG. 17B. The channel 98d extends along the length of the sew tip and then fork into two channels, each leading to one of the two openings 107 having ferrules 103 to which the end of the suture thread is attached. Openings 107 retain ferrules 103 but are slotted to enable release of suture after a ferrule 103 is captured. The operation of sew tip 98 will be described in more detail below in connection with FIGS. 22A–22I.

Figure 21D:
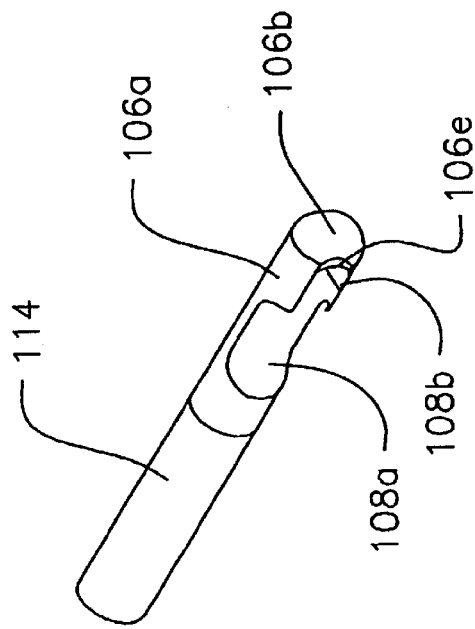
FIGS. 21C and 21D are perspective views showing assembly of the sleeve of FIGS. 21 and 21A.
Figure 21C:
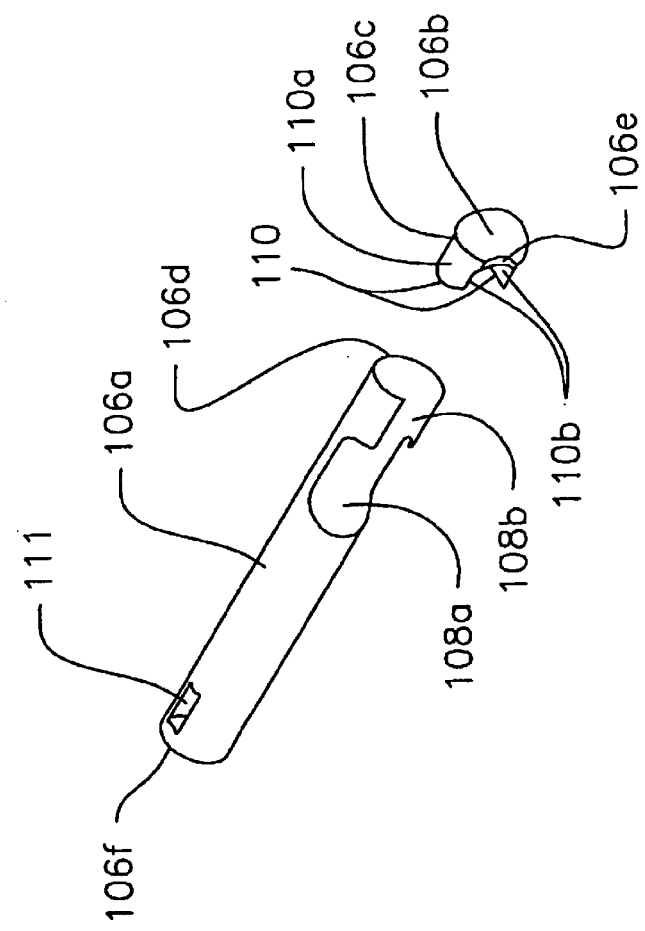

A vacuum sleeve 106 is provided having a tube 106a, and a rounded cap 106b which closes one end of tube 106. The cap 106b has an edge 106c which mates with the edge 106d of tube 106a and two extending flanges 110 which are received in tube 106a to hold the cap in place (FIGS. 21C and 21D). Between flanges 110 the interior surface of the cap is angled to provide a ramp 112 (FIG. 21B). The sew tip 98 in tip tube 102 is received through the open end 106f of tube 106b, such that an opening 108 of tube 106b is located over gap 104 of the sew tip. The two flanges 110 of cap 106d register with the two sides of the forward part 98g of the sew tip 98 to properly align sew tip 98 and tip tube 102 in the vacuum sleeve 106. The opening 108 represents a cut into tube 106a to provide a oval shaped window 108a and a forward slot 108b which extend from window 108a to the end of tube 106a meeting cap 106b, such that the forward (ferrule carrying) part 98g of the sew tip 98 partially extends through slot 108b (FIG. 21B). Cap 106b has a notch 106e located adjacent slot 108b at edge 106d of tube 106a (FIG. 21D). The ramp 112 is negatively sloped at an angle towards slot 108b, as shown in FIG. 21B, to facilitate the suturing process, as will be described later. Two fingers or prongs 103 extend from the sides of the tip tube 102 and are received in two corresponding openings 111 of the vacuum sleeve 106 to latch the sleeve in position over the sew tip. Guide member 58 extends into tip tube 102 as shown in FIGS. 18B–21B. Shrink wrap or tubing 114 is then applied over tube 106a, such that openings 111 are sealed closed, to complete the assembly of the vacuum sleeve 106, as shown in FIG. 21A. A short metal ring 116 is placed over the end 102a of the tip tube 102 and the edge of the shrink wrap 62 extending along shaft 18b. In placing ring 116, shrink wrap 62 is first applied over shaft 18b and tube 102, and then cut back to an edge 106a of ring 116. Tubes 102 and 106a are both made of metal, such as stainless steel, and cap 106a may be made of molded plastic. A cross-section of tissue engaging end 16a through the sew tip 98, tip tube 102, and vacuum sleeve 106, is shown in FIG. 17. This vacuum sleeve 106 enables a vacuum or partial vacuum to be applied to the path of the suture following gasket member 51, via the vacuum connection assembly 64, to channel 98d of the sew tip 98, such that the upflow of air into the gap 104 of the sew tip through opening 108 of vacuum sleeve 106 can pull the tissue into the gap. The suction from the vacuum or partial vacuum is applied to gap 104 of the sew tip 98 via two openings 98e in channel 98d to two cavities 98f each located on opposite sides of the sew tip in the space between the sides of sew tip 98 and vacuum sleeve 106 near gap 104 (FIG. 21). Although cap 106b as described herein is preferred, cap 106b may be provided by a metal cap 118, such as of stainless steel attached to the end of tube 106a, and provides a small ramp 118a.

The tissue engaging end of suturing instrument 16 may be as described in U.S. patent application Ser. No.09/686,420, filed Oct. 11, 2000, which is herein incorporated by reference. This Patent Application describes the loading of a length of suture material, i.e., thread, whose ends are affixed to ferrules in the sew tip 98. Before such loading, the vacuum sleeve 106 is removed from tube tip 102 by pushing in fingers 103 to release them from openings 111 and then simultaneously pulling the vacuum sleeve 106 away from tube tip 102. After loading, the vacuum sleeve 106 is replaced and latched back (i.e., fingers 103 in openings 111) onto the tube tip 102 and the loop of suture extends from the ferrules through the suture tracks 53a and 58a of guide members 53 and 58 to suture routing tube 47, via track 56b of the coupler member 56 and opening 51a of the gasket member 51, out holes 76 and 76a of valve 19. Proper orientation of the vacuum sleeve 106 over tube tip 102 and sew tip 98 is provided by flanges 111 of cap 106b, as described earlier, and also by ramp 112 being angled such that it prevents upside down misalignment of the vacuum sleeve over the sew tip. The forward section 98g of the sew tip will be stopped by ramp 112 before fingers 103 reach to the tube tip openings 111, preventing the vacuum sleeve 106 from latching. For example, the suture material may represent monofilament suture material or braided suture material.

Figure 22A:
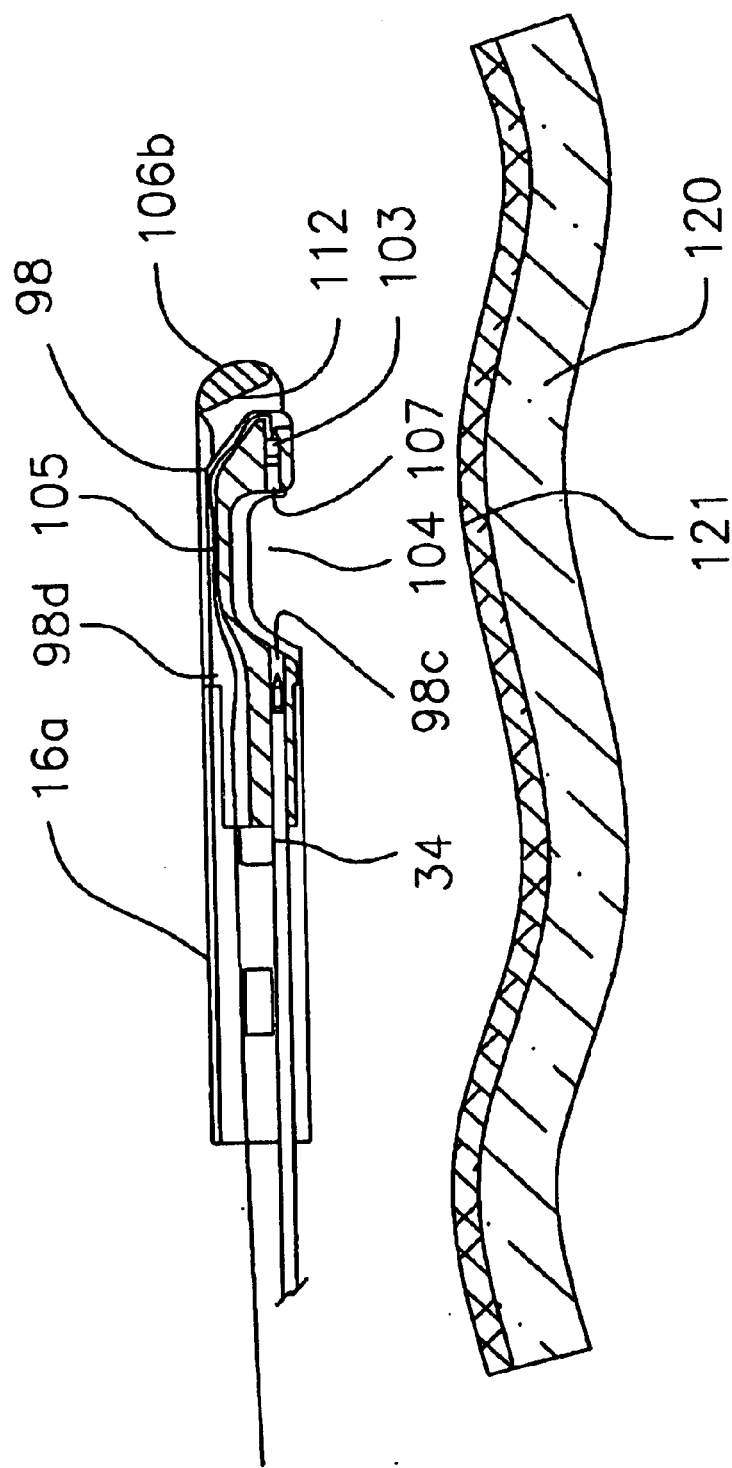
FIGS. 22A–22H illustrates at the tissue engaging end of the suturing instrument the process of applying one end of a loop of suture through tissue with either one the two needles of the instrument.
Figure 22B:
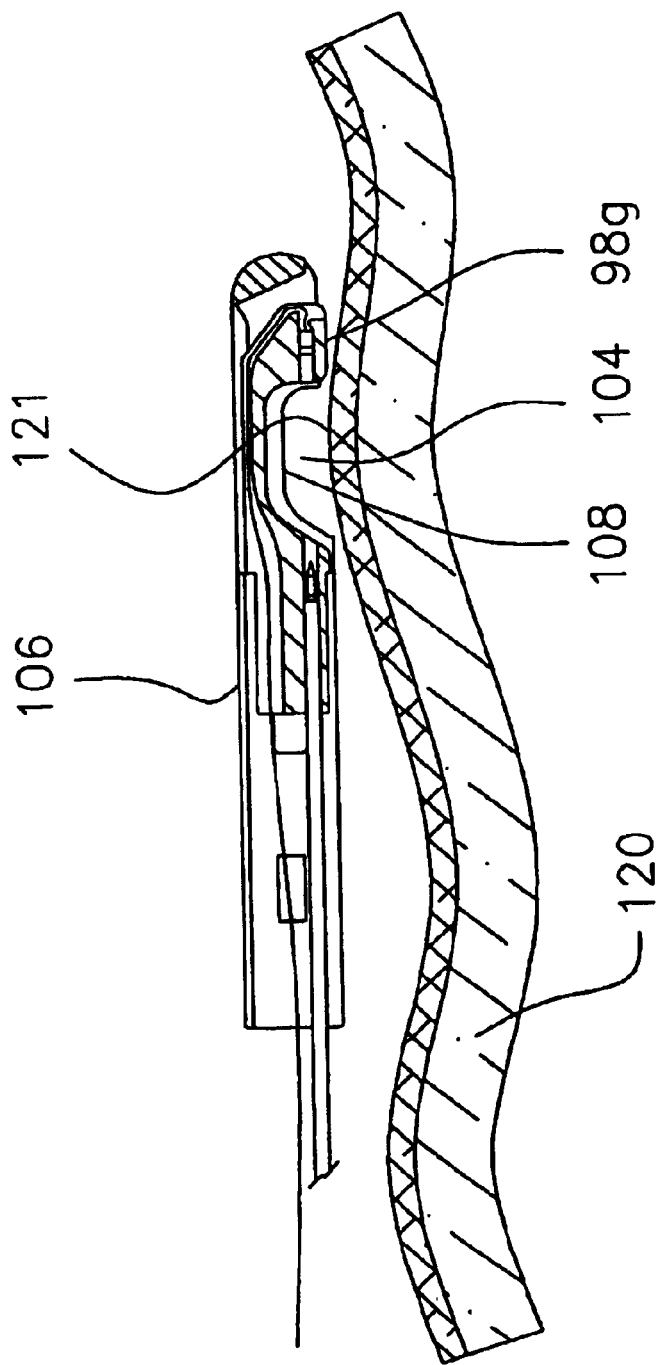
Figure 22C:
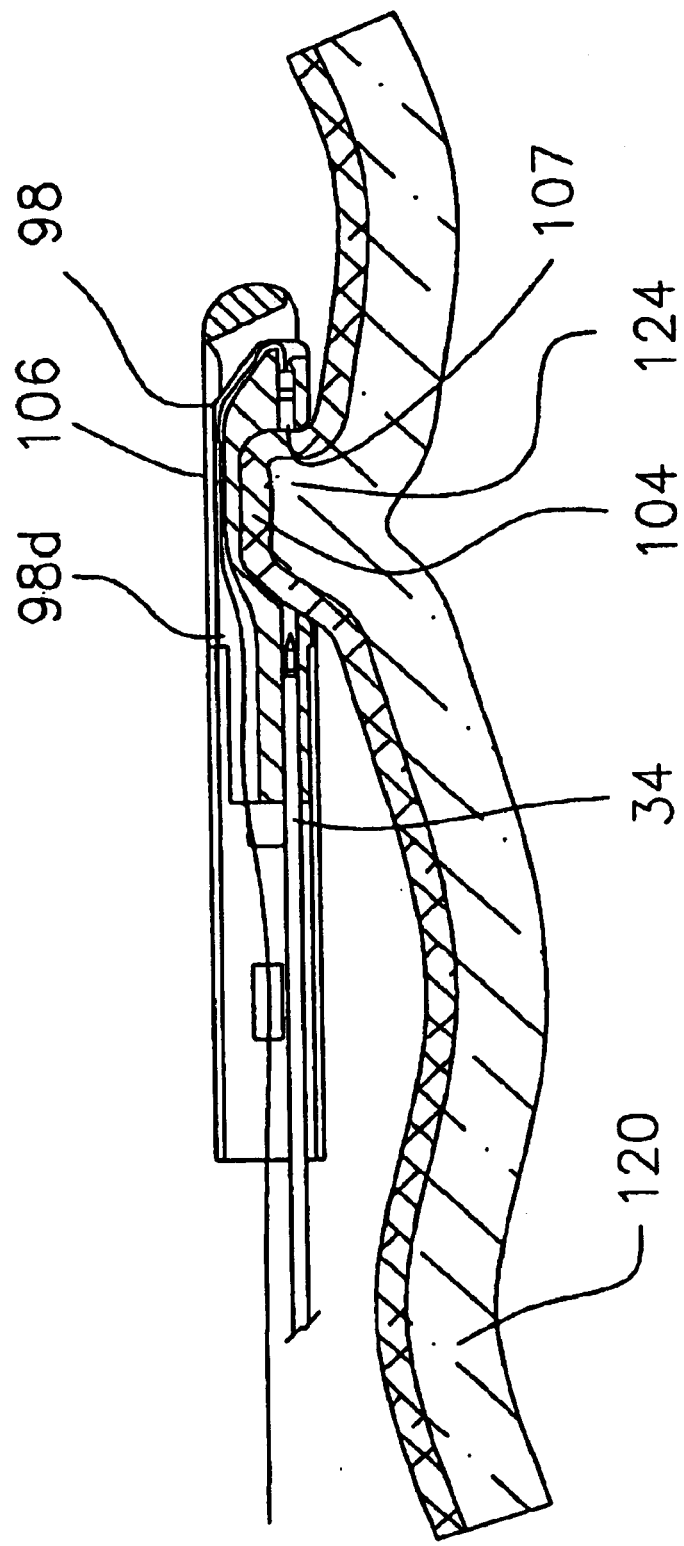
Figure 22D:
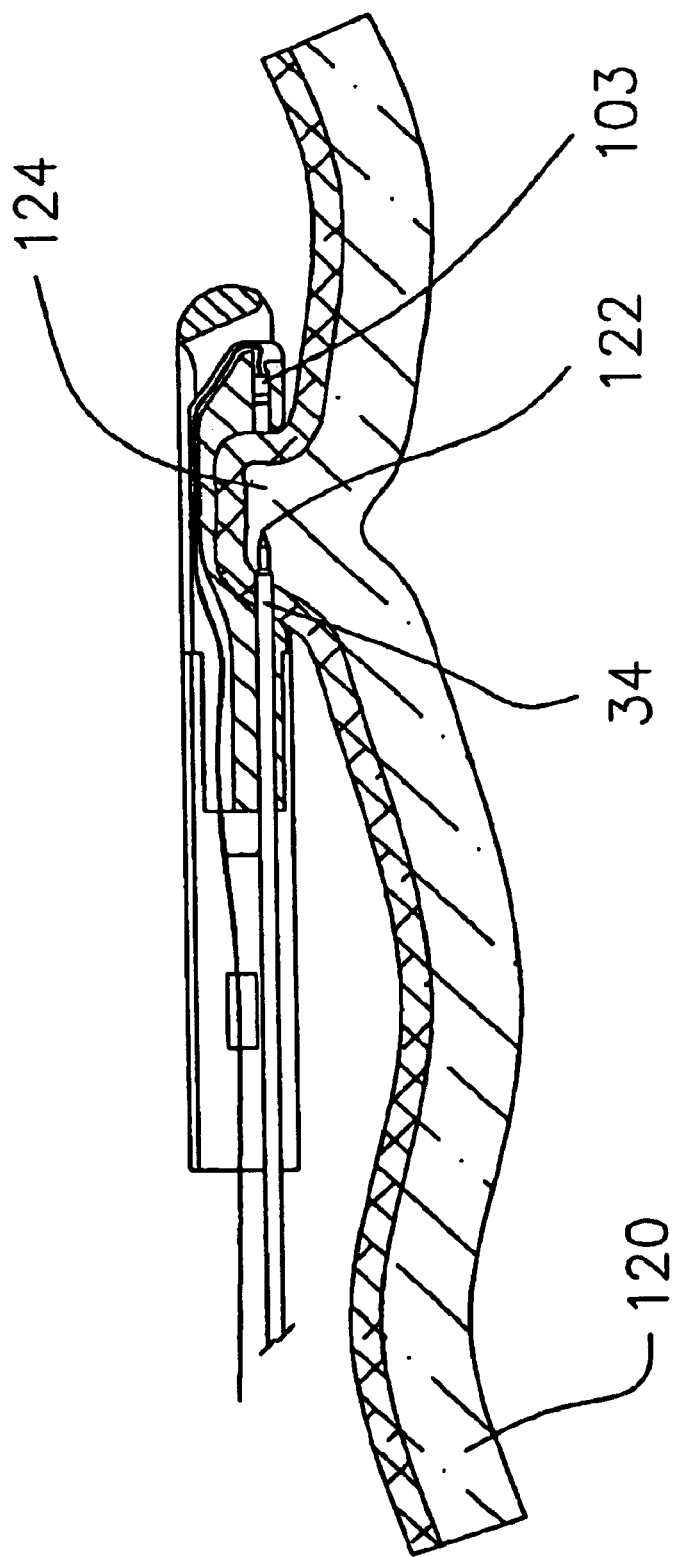
Figure 22E:
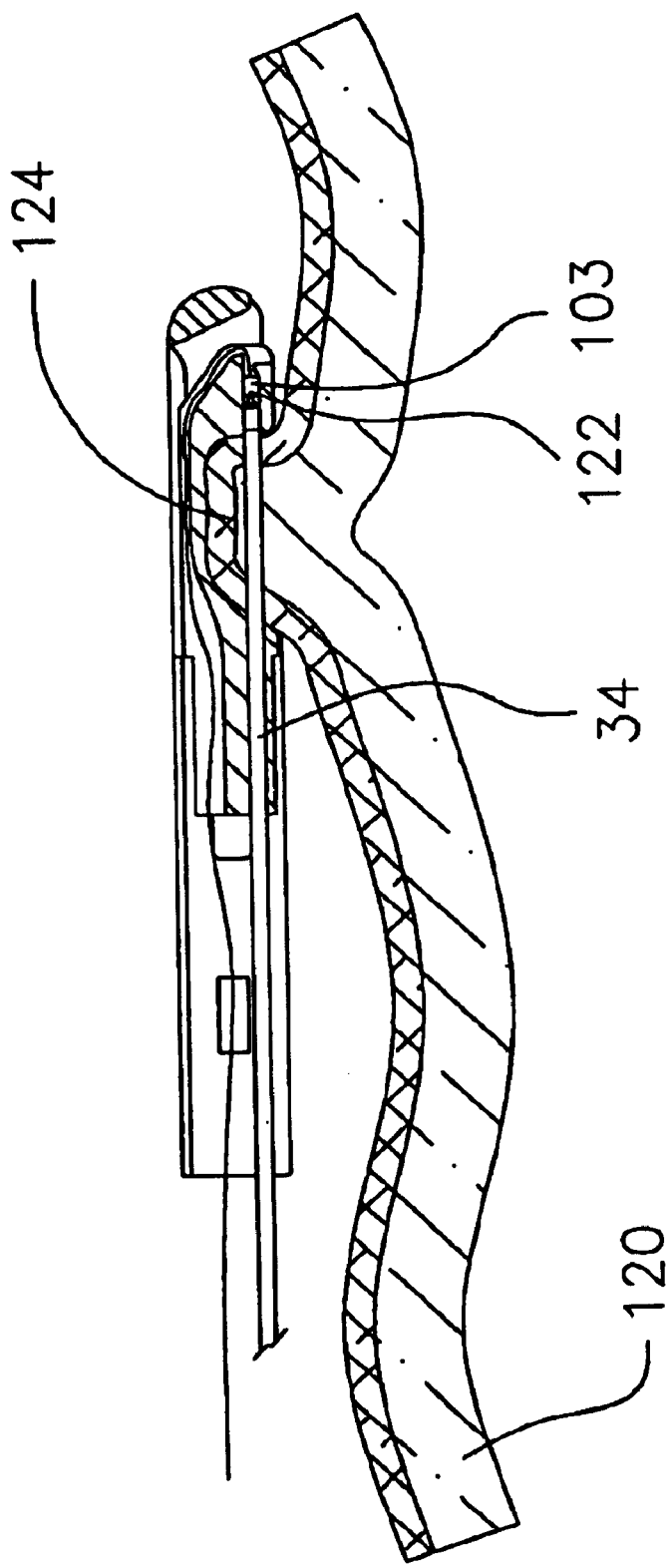
Figure 22F:
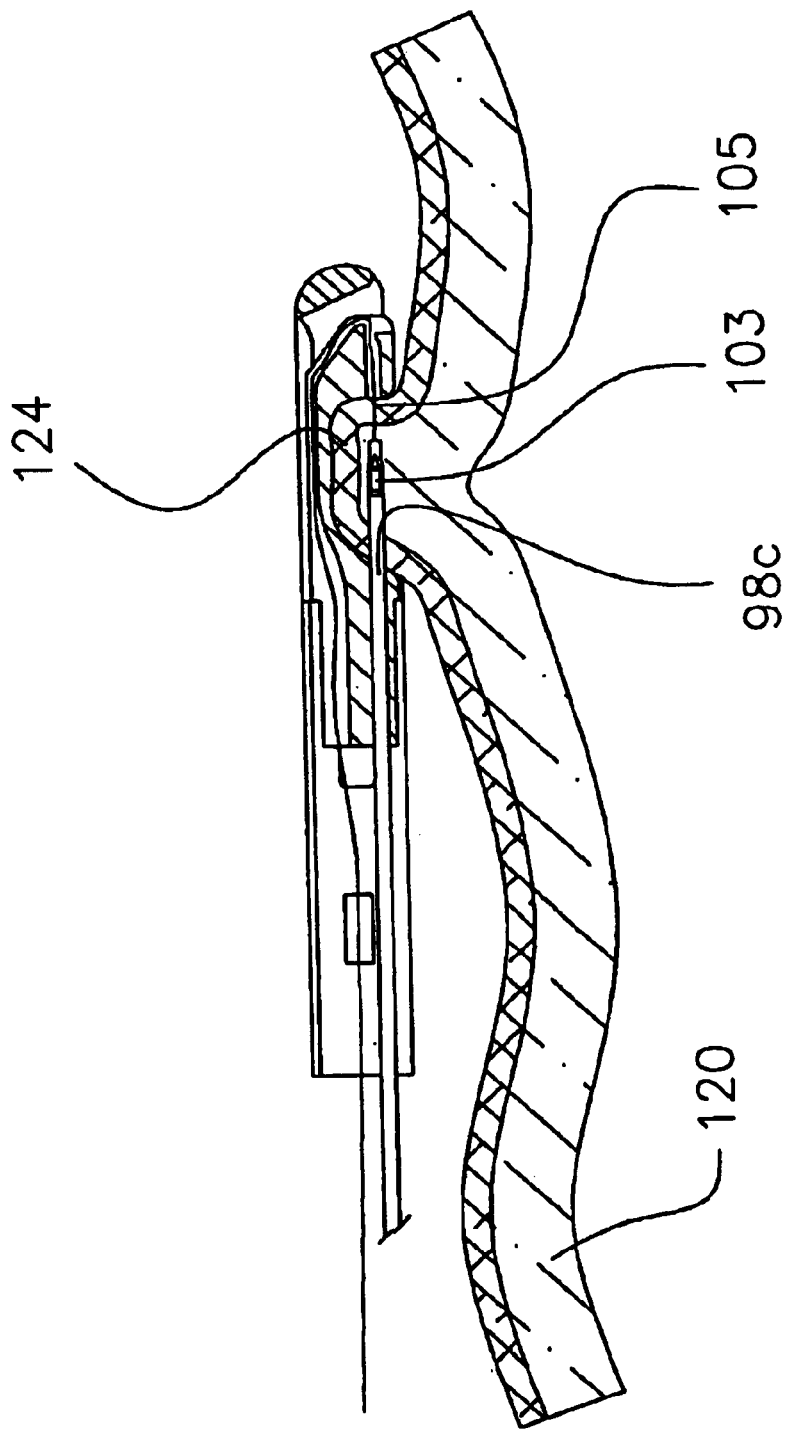
Figure 22G:
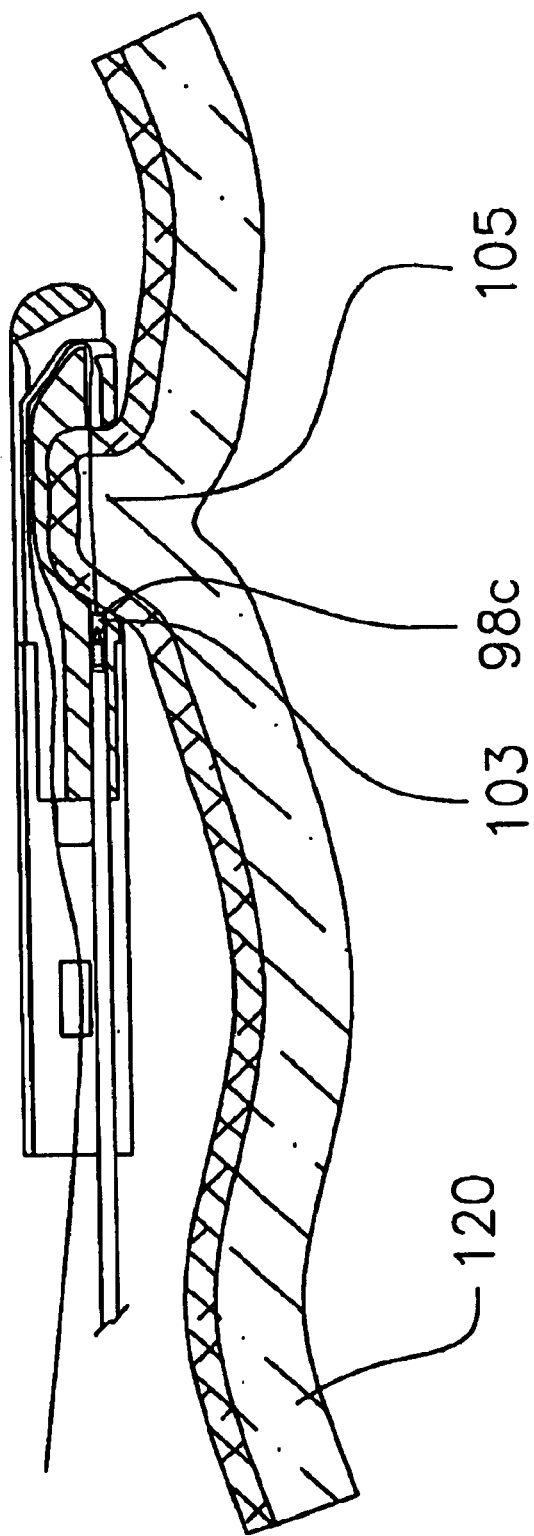
Figure 22H:
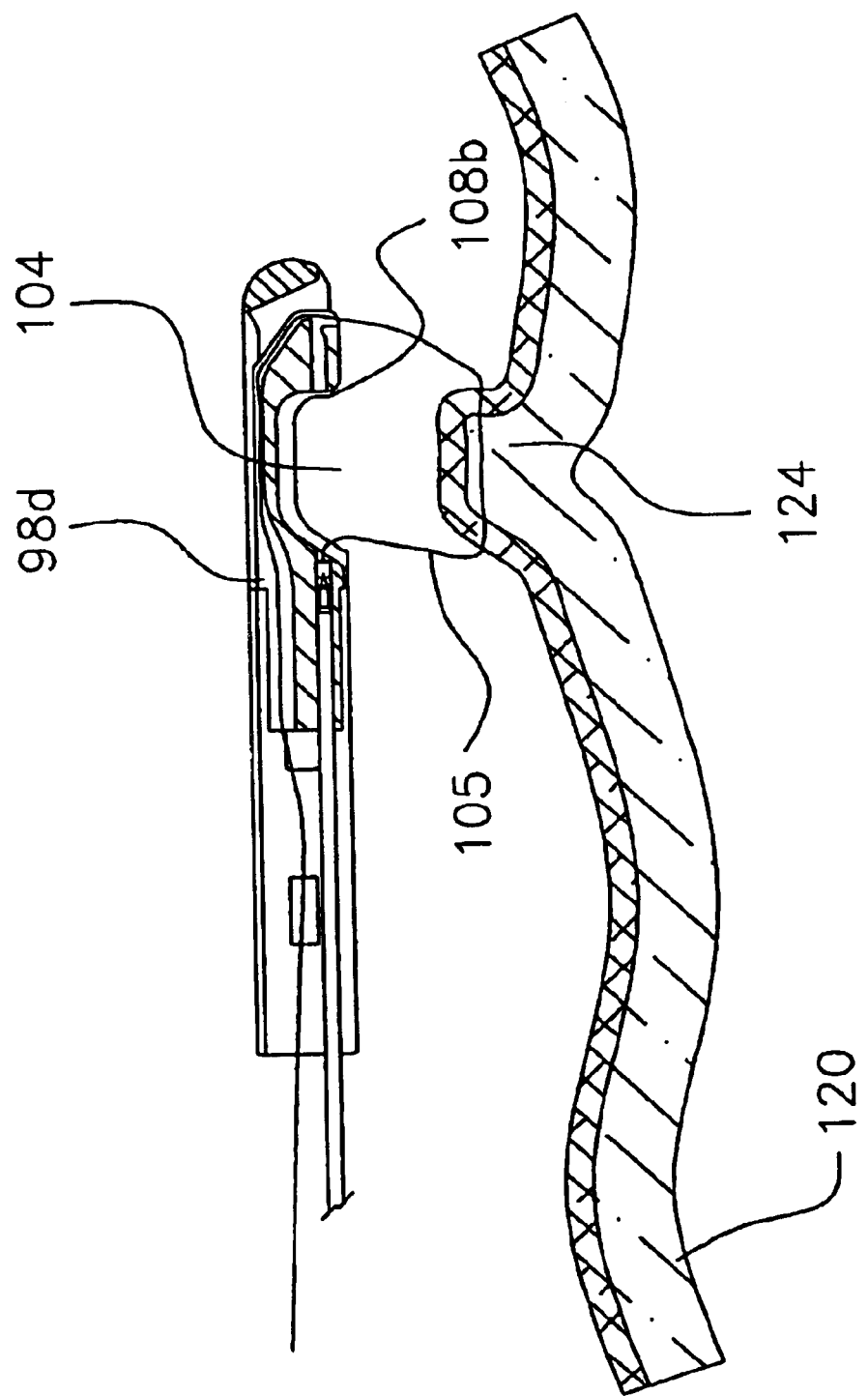
Figure 22I:
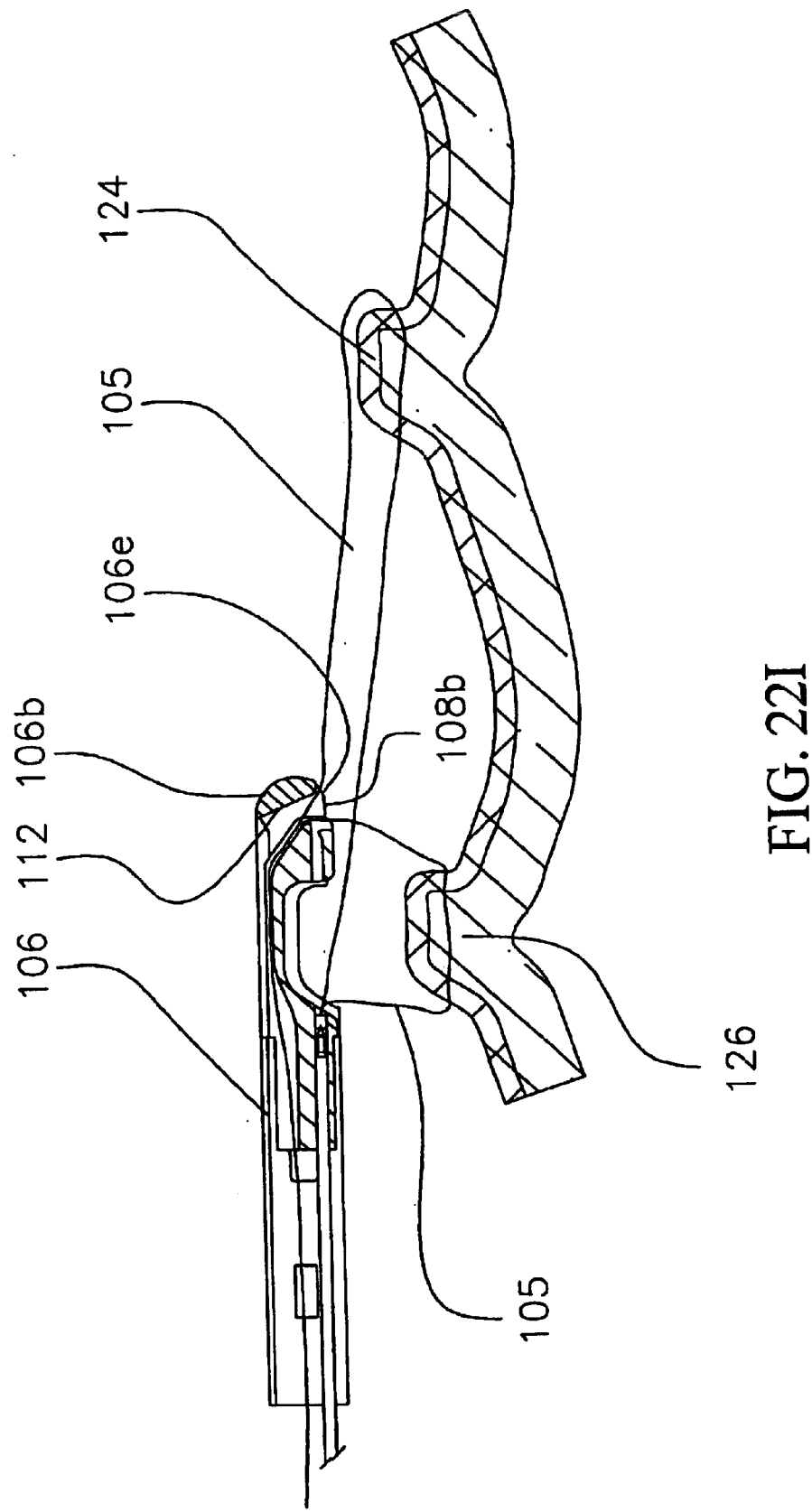
FIG. 22I illustrates at the tissue engaging end of the suturing instrument after both of the needles of the instrument have applied the two ends of the suture loop in the tissue, such that removal of the instrument leaves the suture loop through the tissue.

Referring to FIGS. 22A–22I, the operation of the suturing instrument 16 at the tissue engaging end 16a is shown after the suturing instrument is located, via accessory tube 12, near the tissue to be sutured. FIGS. 22A–22H show the process of applying one end of the suture through tissue 120 with needle 34, the same process is repeated for the other end of the suture for needle 35. Suturing with needles 34 and 35 may be provided in any order. In FIG. 22A, the tissue engaging end 16a is shown with suture material 105 loaded in the sew tip 98, such that the two free ends of the loop of suture extend from the suture track 58a of tube guide 58, via a passage 98d of the sew tip 98, to two ferrules 103 coupled to the two suture ends in the sew tip 98. Opening 98c at one end of gap 104 face ferrules 103 in openings 107 for respectively needles 34 and 35. The tissue engaging end 16a is placed adjacent a first target area 121 in tissue 120 where the first end of the suture will be placed (FIG. 22B). Suction is then applied to pull the target area 121 of tissue 120 via gap 104 of the sew tip through opening 108 in the vacuum sleeve 106 to capture a fold 124 of tissue 120 at target area 121 (FIG. 22C). To apply suction, valve 19 is closed and a vacuum source, such as a vacuum pump 200 (FIG. 29B), provides suction to shaft 16b, via tubing, to port 74 of the vacuum connection assembly 64. The vacuum is communicated into gap 104 via opening 52c of rigid tube 52 to the suction channel in shaft 16b formed by suture track 53c of guide member 53, track 56b of coupler member 56, and then suture track 58d through coupler member 56 to channel 98d and cavities 98f of the sew tip 98. Principally, the suction is applied to cavities 98f, however the suction may occur elsewhere about gap 104, such as the space between the sew tip 98 and the interior surface of the vacuum sleeve 106, or via openings 107. With the suction maintained, and needle 34 selected by an operator using selector lever 44, and the actuator member 36 is pulled by the operator towards handle 30a (FIG. 8), the needle passes through the tissue (FIG. 22D) and then into ferrule 103 (FIG. 22E), such that the tip 122 of the needle is captured in the ferrule. Although valve 19 is closed, the suture may be drawn through the valve seat 19a. The actuator member 36 rotates against the bias of spring 38 until needle tip 122 engages ferrule 103. The amount of rotation of actuator member 36 depends on the distance the needle must transverse before engaging a ferrule, such distance may vary depending on the degree of flexing of shaft 16b along its flexible section 33. The needle 34 is then retracted by the operator releasing actuator member 36, to pass the needle and captured ferrule 103 back through the tissue (FIG. 22F) and into opening 98c (FIG. 22G). The suction generates negative air pressure near the tissue 120 sufficient to pull the tissue into gap 104 of the sew tip 98 without damaging the tissue. The suction is then discontinued, such as by turning off the vacuum source 200, and the valve 19 opened to release the tissue from gap 104 of the sew tip (FIG. 22H). The end of the suture thread extends from the captured ferrule on the needle tip through tissue 120 to channel 98d. The suture releases through the slot extending along opening 108b and the suture extends from captured ferrule through the tissue to channel 98d. The process of FIGS. 22A–22H is then repeated at a second target area in the tissue with needle 35 selected to place the second end of the suture in the tissue. FIG. 22I shows the result after both suture ends are placed through tissue, where one suture end extends through tissue fold 124 and the other through fold 126. For example, the second target area may be located directly after placing the first suture end through the tissue by rotating the housing 30 of the instrument 180 degree to rotate the tissue engaging end 180 degrees. The entire operation is observed by the operator via the gastroscope, and in this manner, the first and second target located by the operator in the tissue. The operator may be a surgeon, gastroenterologist, or other skilled physician.

Figure 23:
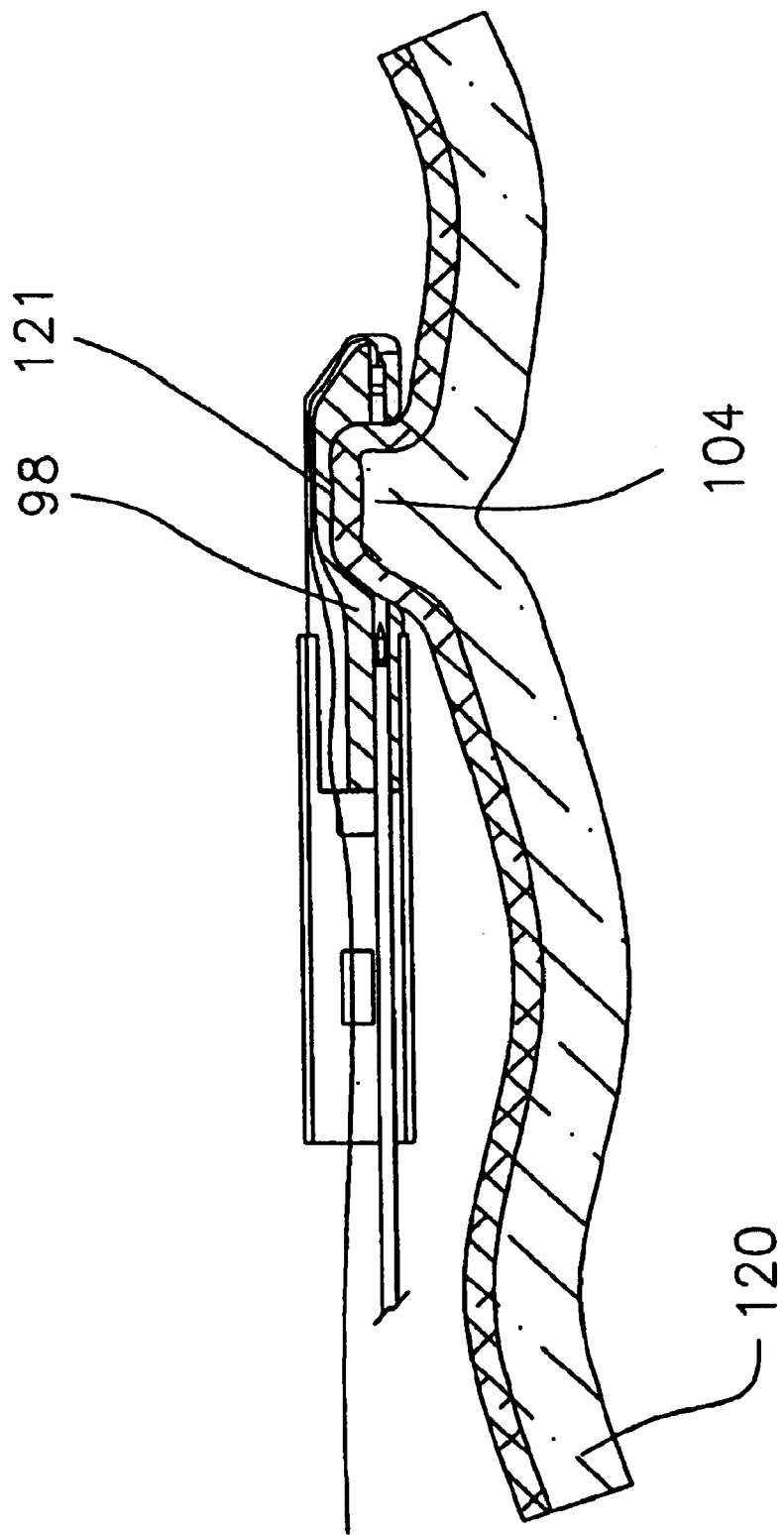
FIG. 23 illustrates the operation of the tissue engaging end of the suturing instrument in accordance with another embodiment of the instrument without the outer sleeve of the tissue engaging end, where suction is not needed to capture tissue in applying a suture.

Alternatively, the suturing instrument may operate to apply a suture without suction if the target area of tissue can be sufficiently received in gap 104 of the sew tip 98. For example, the target area may represent a raised portion of tissue to be sutured. Further, the suturing instrument operating without section, may be used with the vacuum sleeve 106 removed from the tissue engaging end 16a, such as shown for example in FIG. 23.

After two ends of the suture have been placed through the tissue, as illustrated in FIG. 22I, the suturing instrument 16 is removed from the accessory tube 12, which pulls the loop of suture, which extended from housing 30, down to tissue 120. As the suture passes through the tissue engaging end 16a, the suture follows from channel 98d of the sew tip over the ramp 112 and notch 106e of cap 106b. The suture may then be secure by a suture securing instrument 130 described below.

Figure 24:
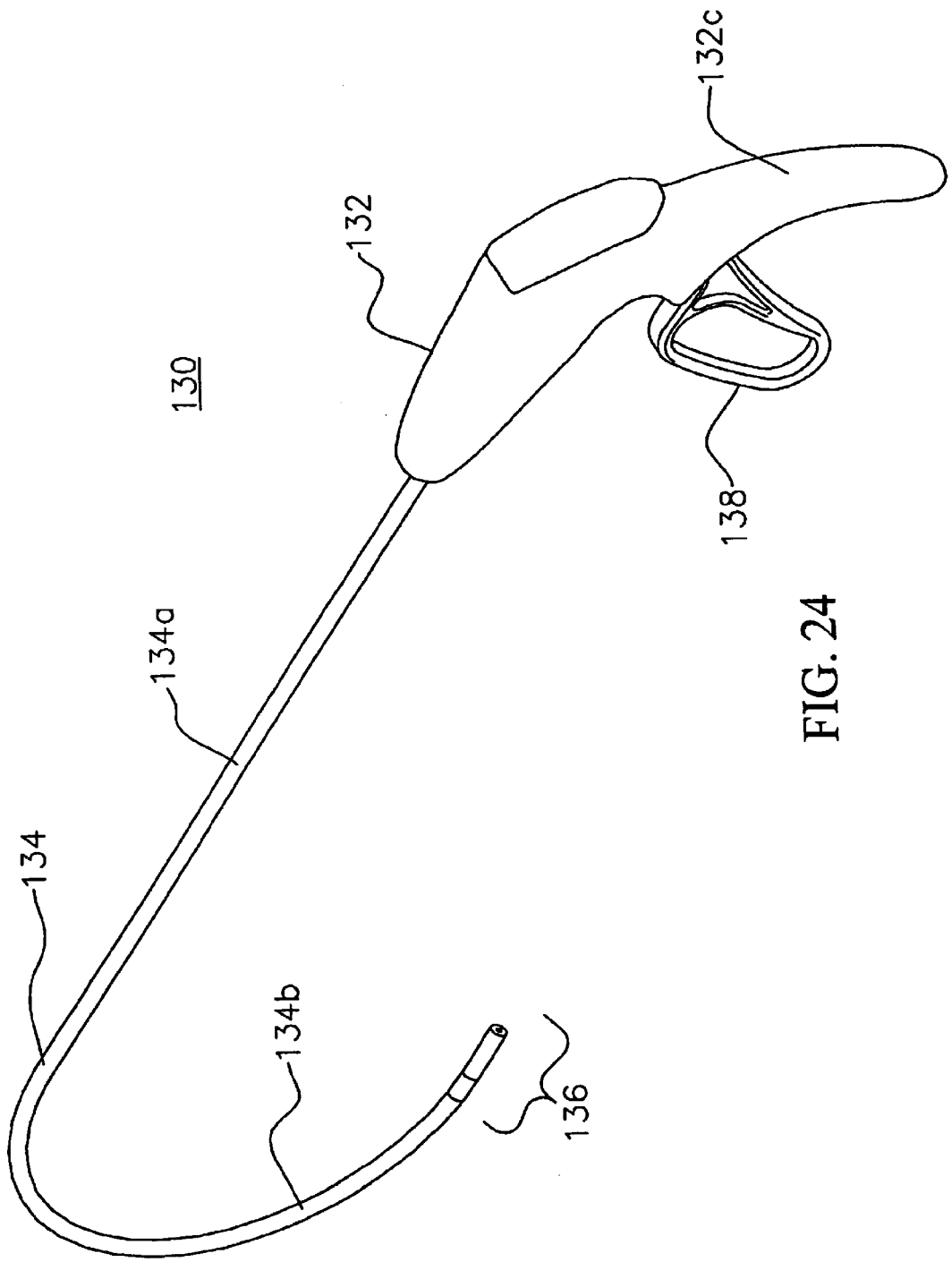
FIG. 24 is a perspective view of the suture securing instrument of the system in accordance with the present invention to retain close the suture applied by the suturing instrument.
Figure 24A:
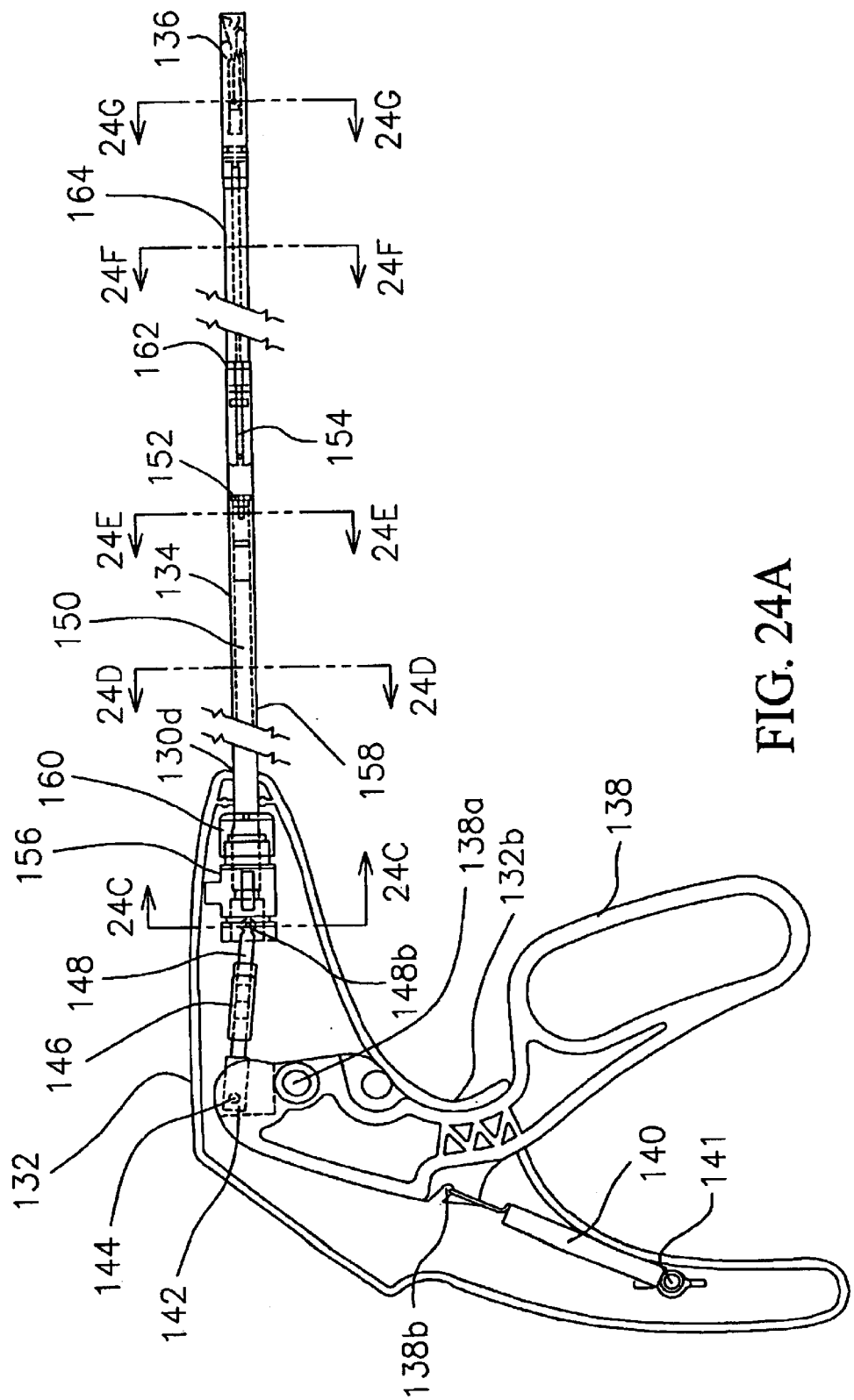
FIG. 24A is a side view of the suture securing instrument of FIG. 24 in which the right cover of the housing of the instrument is removed.
Figure 24B:
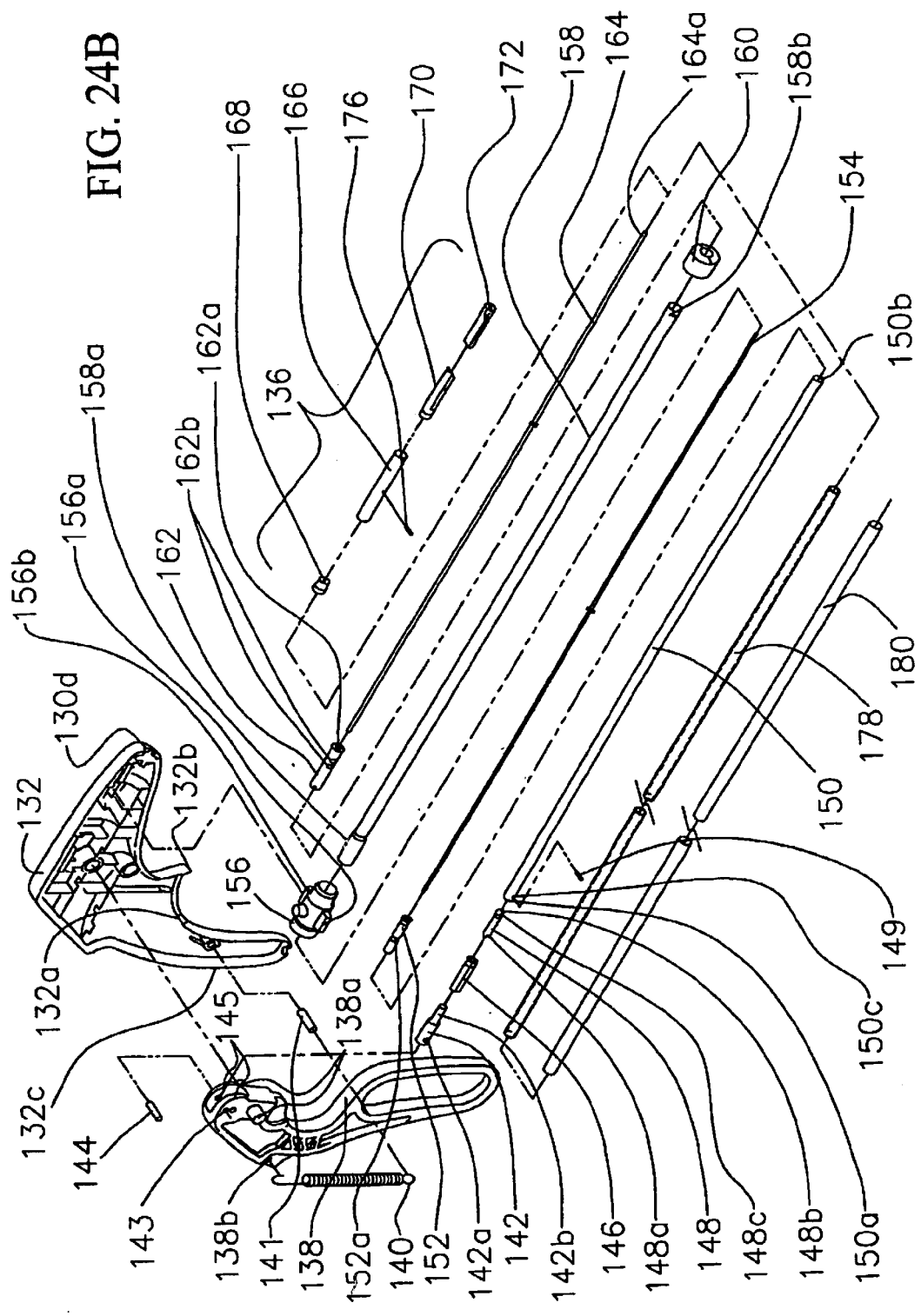
FIG. 24B is an exploded view of the suture securing instrument of FIG. 24 in which the right cover of the housing is removed.

Referring to FIGS. 24, 24A, and 24B, the suture securing instrument 130 of the system is shown having a housing 132 similar to housing 30 of suturing instrument 16. Suture securing instrument 130 represents the Ti-KNOT® TK•5™manufactured by LaserSurge, Inc. of Rochester, N.Y., except that its shaft 134 is longer and partially flexible, and means are provided for calibrating the length of a drive wire to the distal end 136 of the instrument 130. The distal end of instrument 130 may be similar to that described in U.S. Pat. Nos. 5,669,917, 5,643,289, 5,520,702, or European Patent Application No. 95102587.3, filed Feb. 23, 1995 and published Feb. 2, 1994 under Publication No. 0669103A1, which are herein incorporated by reference. The suture securing instrument 130 includes an actuator member 138 representing a lever having two pins 138a extending into holes in the sides of housing 132 upon which the actuator member is pivotally mounted in the housing. Actuator member 138 has a portion which extends through an opening 132a in housing 132 to enable pivotal movement about pin 138a. A extension spring 140 is provided which hooks at one end in a notch 138b of actuator member 138 and is wound at the other end around a pin 141 located in holes in the sides of housing 132, such that the actuator member 138 is spring biased to retain actuator member 138 normally in a forward position, as shown for example in FIG. 24A. The body of housing 132 has a front portion 132b providing a stop that limits the pivotal movement of the actuator member 138. A pivot barrel 142 is coupled by a pin 144 which extends through an opening 142a through the pivot barrel and two holes 143 between flanges 144 of actuator member 138. A turnbuckle 146 is provided representing a tubular member which has an interior surface right-hand threaded from one end and left-hand threaded from the other end. The turnbuckle 146 is attached to a threaded circular end 142b of pivot barrel 142 and then to the threaded circular end 148a of a ball connector 148. The ball connector has a ball 148b having a hole 148c there through. Drive tube 150 has one end 150a into which ball 148b is received and then coupled to the tube, via a pin 149, which extend through hole 148c of the ball 148b and two holes 150c in drive tube 150. An adapter 152 is received in the other end 150b of the driver tube 150 and has a hole partially extending there through in which is received and attached a drive wire 154. The adapter 152 is mounted in driver tube 150 for rotational movement about an annular groove 152a of the adapter 152. Multiple detents (not shown) are formed in the tube 150, such as by deforming the metal by pressure, over the annular groove 152a. The detents extend into the annular groove 152a to form a track guide within which the adapter 152 may be rotated.

Another adapter 156 is provided which has flanges 156a received in the two sides of housing 132. A rigid tube 158 having an end 158a which is D-shaped is registered into a corresponding shaped opening in adapter 156, and a threaded nut 160 having an opening which extends over mounting tube 158 and screws onto the end of the adapter 156 to secure tube 158 to adapter 156. Rigid tube 158 extends from housing 132 via an opening 130d in the housing. The assembly of components 142, 146, 148, 150, 152, and 154 described above are received in the adapter 156 and through rigid tube 158, as shown in FIG. 24A. A cross-section of the adapter 156 and rigid tube 158 at pin 149 is shown in FIG. 24C. Cross-section of shaft 134 through the rigid tube 158 at the drive tube is shown in FIG. 24D, and at the adapter 152 in FIG. 24E. The drive tube 150 is moveable through rigid tube 158. At the other end 158b of the rigid tube 158 is another adapter 162 which is cylindrical and has a central hole 162a extending there through. The adapter 162 is mounted in tube 158 by mechanical fastening in which small dents in the metal of the tip tube formed with a press into two slots 162b on either side of the adapter 162. The drive wire 154 extends through hole 162a of the adapter 162 and into an extension tube 164 which extends from the adapter 162 to the distal end 136 of instrument 130. Extension tube 164 is a stainless steel tube having for example, an inner diameter of 0.041 inches and an outer diameter of 0.059 inches, and is mounted in hole 162a of adapter 162, such as by welding or brazing, while enabling movement of the drive wire through adapter 162 and extension tube 164. Drive wire 154 may be, for example, stainless steel music wire. A cross-section of shaft 134b through extension tube 164 is shown in FIG. 24F. Pivot barrel 142, turnbuckle 146, ball connector 148, drive tube 150, adapter 152, rigid tube 158, and adapter 162 may be made of metal, such as stainless steel, while adapter 156 may be made of molded plastic.

Figure 25:
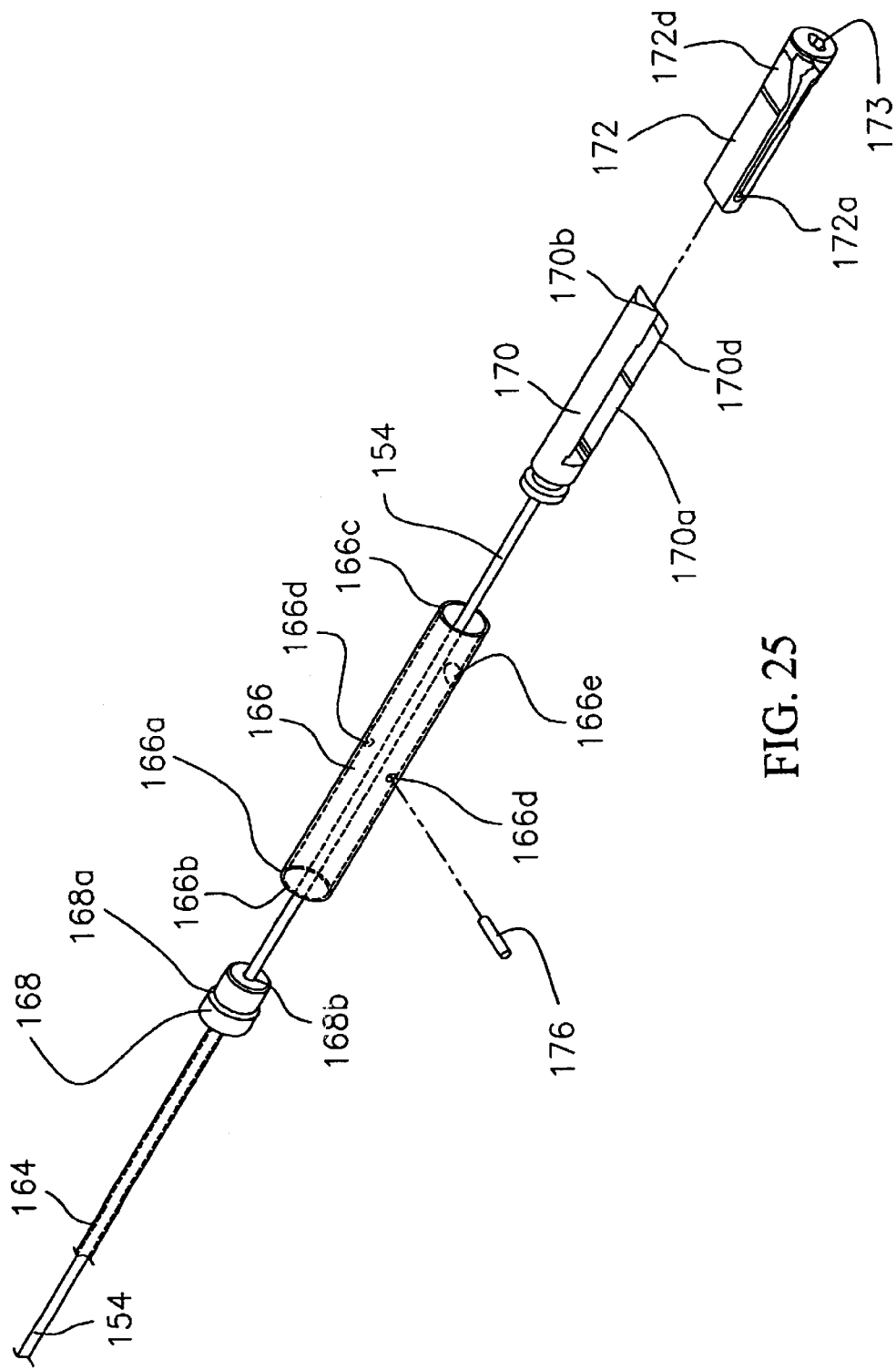
FIG. 25 is exploded view of the distal end of the suture securing instrument of FIG. 24.
Figure 25A:
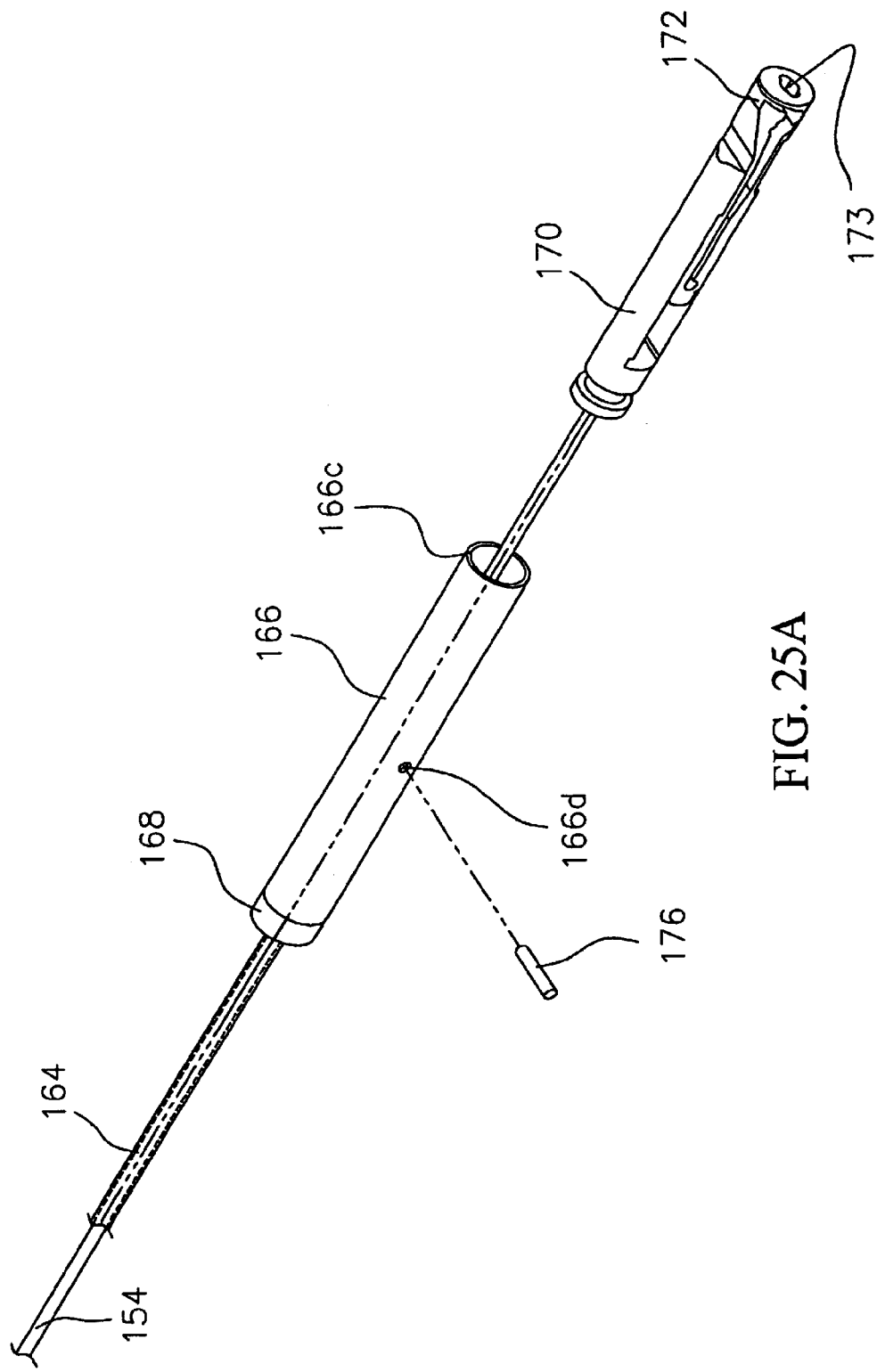

The assembly of the distal end 136 is best shown in FIGS. 25, 25A, and 25B. A tip tube 166 is provided having an end 166a into which is inserted a couple member 168 having an edge 168a which mates along the edge 166b of tip tube 166. The end 164a of extension tube 164 is received into a central hole 168b through coupler member 168 in which the drive wire 154 extends through the coupler member 168 and is received and attached in opening 171 (FIG. 25C) in a wedge tip section 170, where it is attached thereto, such as by welding or brazing. The wedge tip section 170 has a slot 170a partially there through into which is received the hammer and anvil section 172, such that the hammer and anvil section is slidable in slot 170a. Sections 170 and 172 are received in the tip tube 166. A pin 176 extends through two holes 166d and an opening 172a through hammer and anvil section 172 to retain section 172 in tube 166.

A chamber 173 is provided in the hammer and anvil section into which a securing sleeve member 174 (FIG. 25B) is located. The securing sleeve member 174 may be a Titanium Knot™ titanium tube manufactured by LaserSurge, Inc. of Rochester, N.Y. Cross-sections through the distal end 136 of the suture securing instrument are shown in FIGS. 24G and 25C. The wedge tip section has an upper member 170b and a lower member 170d having a knife 170d when wedge tip section 170 is driven forward upper member 170b abuts ramp 172d of the hamper and anvil section 172 to first push hammer 172b down to deform and crimp sleeve member 174 against anvil 172c, and then knife 170d cut sutures extending from sleeve member 174 near opening 166e of tip tube 166. Thus, with ends of suture extending through the sleeve member 174 and exit the opening 166e of the tube tip 166, wedge tip section 170 and the hammer and anvil section 172 provides for crimping the sleeve member to retain the suture and then cuts the suture in response to forward movement of the drive tube 150 and drive wire 154. Drive tube 150 and drive wire 154 are moved forward by an operator pulling actuator member 138 towards handle 132c of housing 132, as will be described in more detail in connection with FIGS. 27A–H. Rotation of adapter 152 in tube 150 facilitates freedom of wedge tip 170 to translate, or tilt, along its center axis, which extends in the direction of wire 154, as the wedge tip is driven forward against the ramped surface of hammer 172b. Rotational movement of actuator member 138 is enabled by pivoting of the pivot barrel 142 about the axis defined by pin 144 in flanges 145.

Before attachment of the distal end 136 to extension tube 164 through which drive wire 154 extends, tube 164 is passes through a flexible plastic tubing 178, such as of Tygon. This tubing 178 extends from end 158b of rigid tube 158, until distal end 136 when mounted to extension tube 164. The diameter of tubing 178 is substantially matched to the outside diameter of tube 158 and tip tube 166. A shrink wrap layer 180 is applied on the entire length of shaft 134 of instrument 130 until distal end 136.

The entire length of the instrument 130 is such that it can extend through accessory tube 12 in which its shaft 134 has a non-flexible section 134a defined by the extend of rigid tube 158, and a flexible section defined by the extent of extension tube 164 in tubing 178. For example, the shaft 134 may be 31.5 inches in length, where its non-flexible section 134a is 12.0 inches in length, and the flexible section 134b is 19.5 inches in length.

Figure 26D:
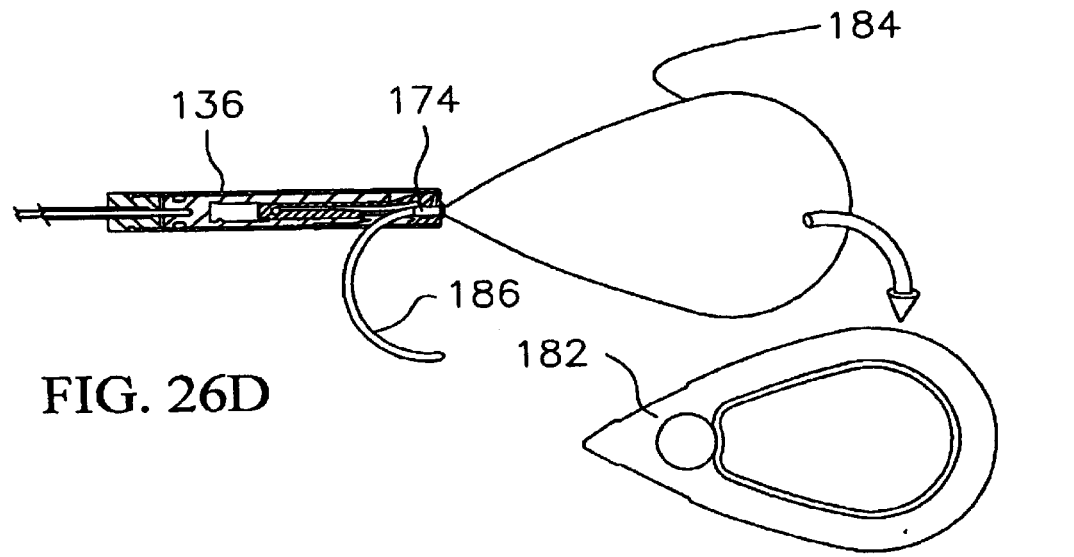
Figure 26E:
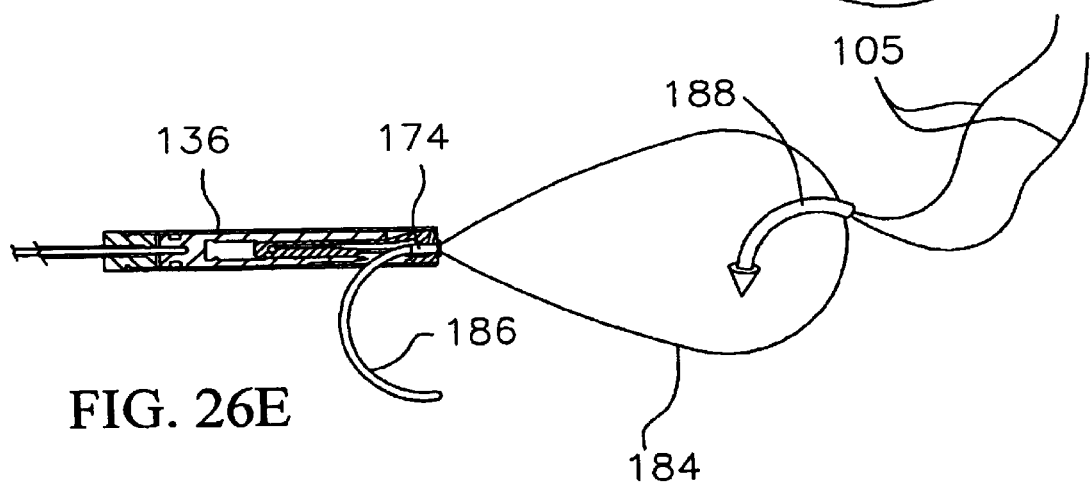
FIGS. 26E–26I illustrate use of the guide wire loop of FIG. 26D to load the suture through the sleeve member at the distal end of the suture securing instrument of FIG. 24.
Figure 26F:
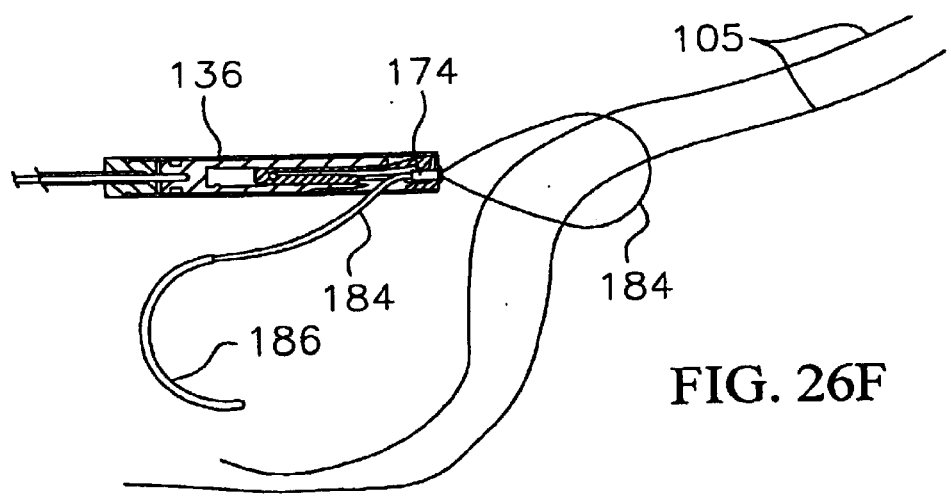

Referring to FIGS. 26A–26D, the loading of sleeve member 174 into the distal end 136 of the suture securing instrument 130 is shown using a flexible holder 182 having a outer groove (not shown) around which a wire 184 is passed to forming a loop. This loading holder is commercially available as a Ti-KNOT® TK•5™ Quick Load™ unit from LaserSurge, Inc., Rochester, N.Y. Holder 182 may be made of molded rubber, and having an opening 182a for the fingers of an operator. The ends of the wire loop 184 are attached to a C-shaped or curved handle 186, which may be composed of metal. A sleeve member 174 is slid along ring 186 until reaches the end of the ring at 186a (FIG. 26A). The ring 186 is then passed through chamber 173 of the distal end 136 between the hammer 172b and anvil 172c of section 172 and then exits through opening 166e of the tip tube 166 (FIG. 26B), until sleeve member 174 is located in chamber 173 (FIG. 26C). The flexible holder 184 may then be removed (FIG. 26D).

Figure 26G:
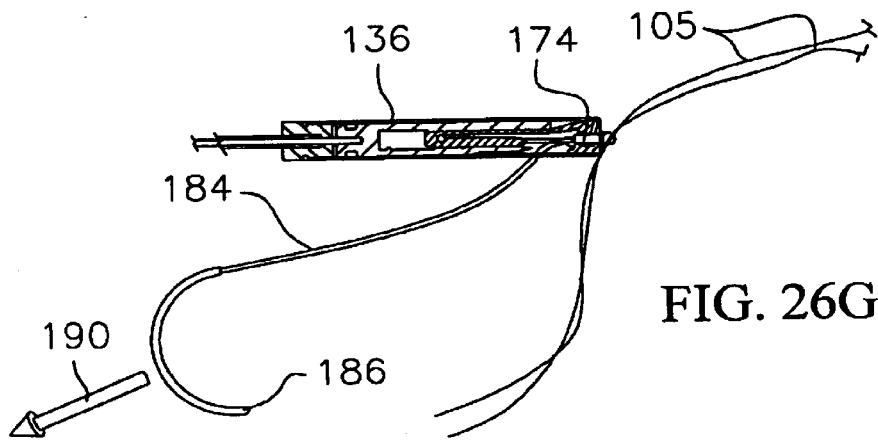
Figure 26H:
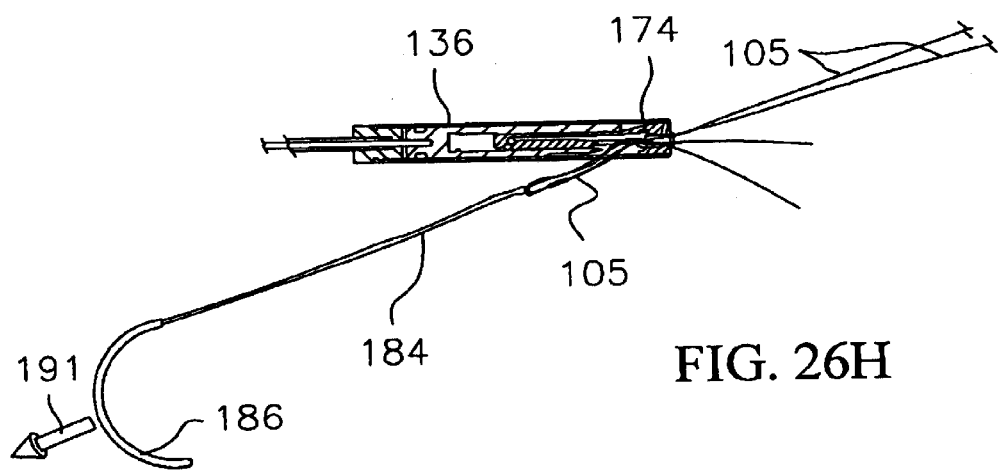
Figure 26I:
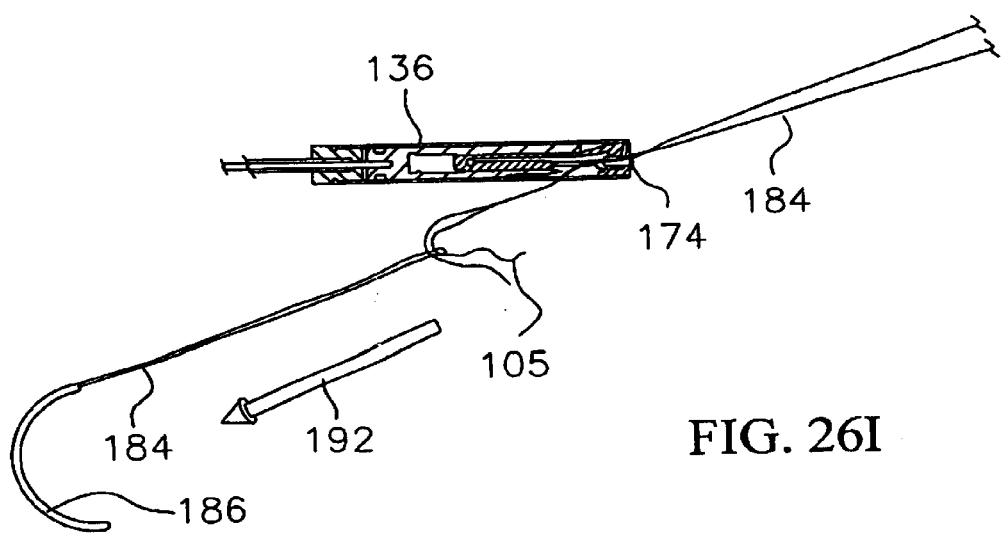

Referring to FIGS. 26E–26I, the loading of the two ends of a loop of suture 105 through a loaded sleeve member 174 in the distal end 136 of the suture securing instrument 130 is shown. The two ends of suture 105 are passed through the wire loop 184 (FIG. 26E), as shown by arrow 188, and are captured by the wire loop as the C-shaped handle 186 is used to pull the wire loop through the sleeve member 174 (FIG. 26F) and opening 166e of the tube tip 166, thereby pulling the two ends of the loop of suture through the sleeve member and opening 166e in the direction indicated by arrows 190–192 (FIGS. 26G–26I).

Figure 27A:
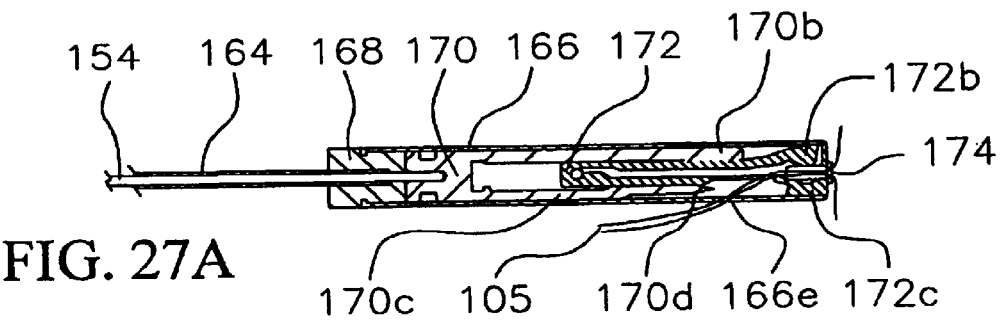
FIGS. 27A–27I illustrates at the distal end of the suture securing instrument the process of fastening a sleeve member to retain the sutured tissue closed and cutting of the suture.
Figure 27C:
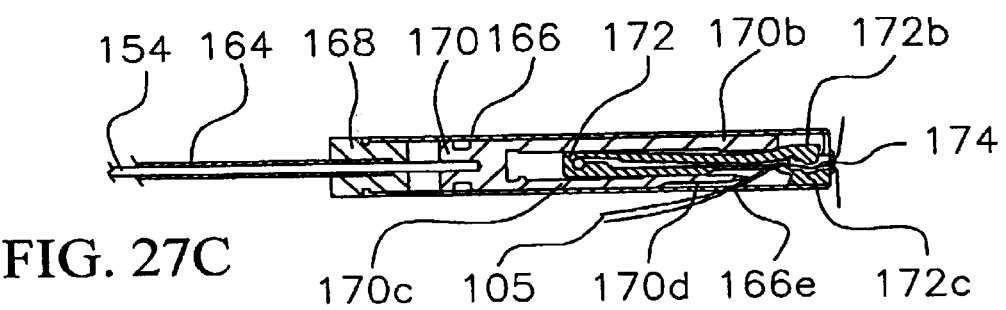
Figure 27E:
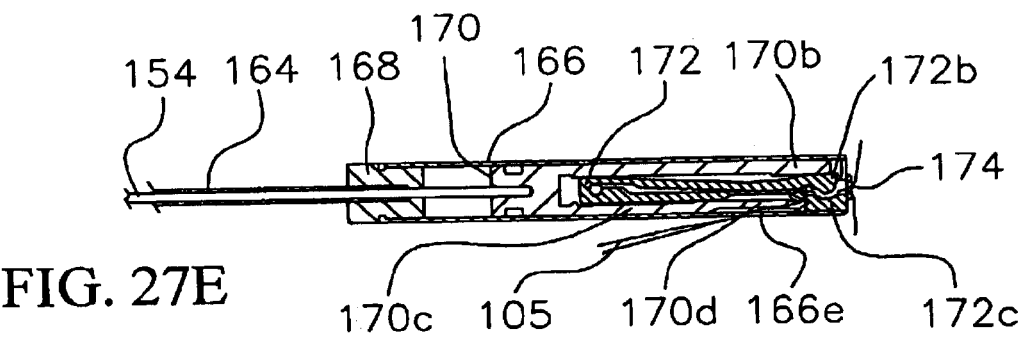
Figure 27G:
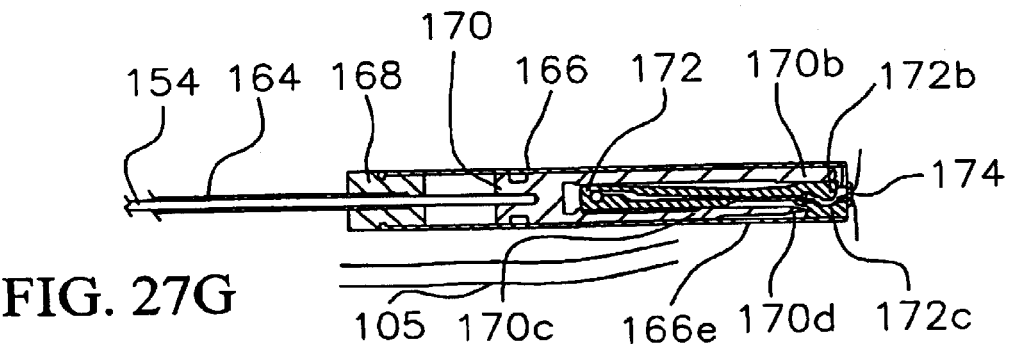
Figure 27B:
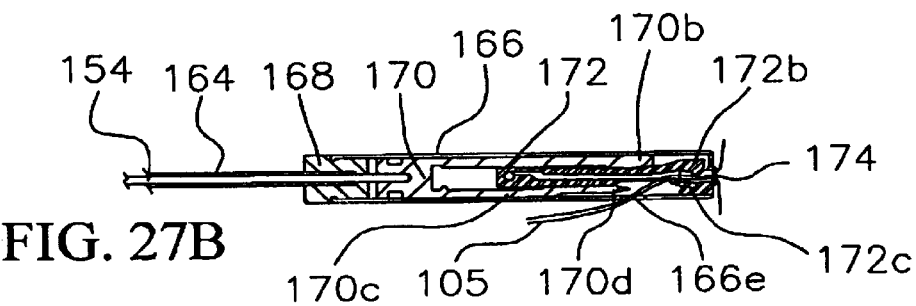
Figure 27D:
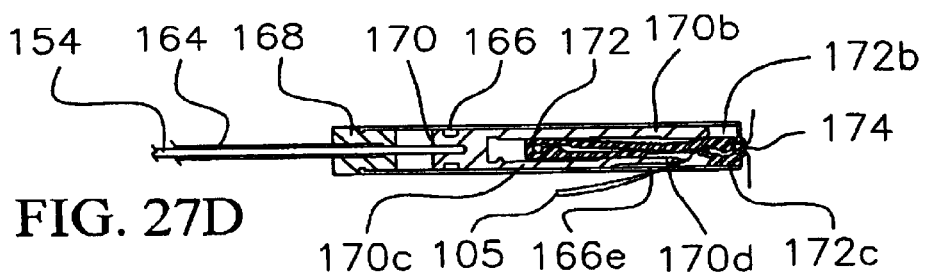
Figure 27F:
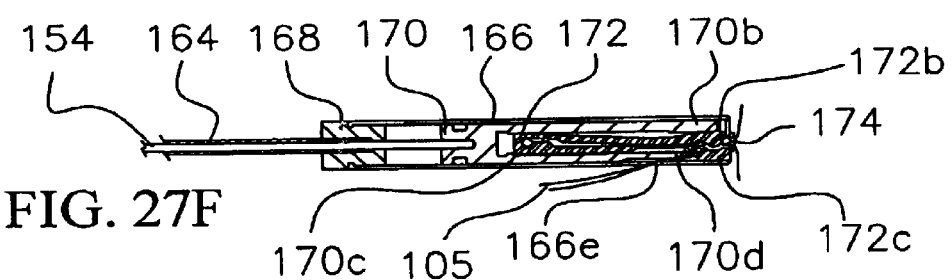
Figure 27H:
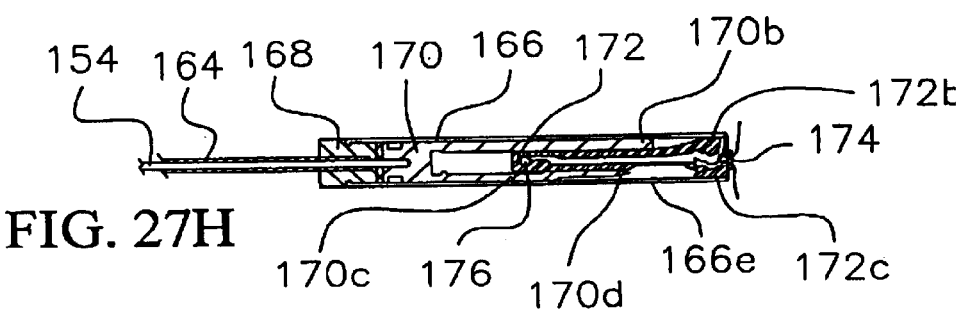
Figure 27I:
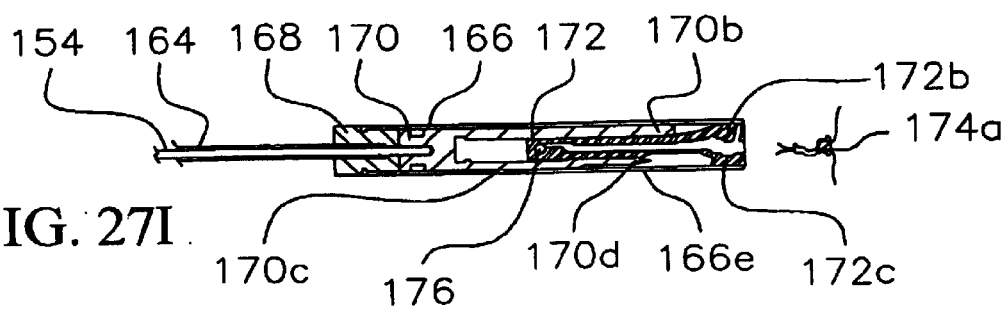

FIGS. 27A–27H shows the operation of suture securing instrument 130 to secure and cut the suture. With the ends of the loop of suture 105 extending through the sleeve member 174 at the distal end 136 of the suture securing instrument 130, the instrument maybe inserted into the accessory tube 12 down to the tissue through which the suture loop extends. The ends of the suture are pulled through the distal end 136, until sleeve member 174 is located adjacent the tissue (FIG. 27A). An operator then pulls the actuator member 138 towards handle 132c, driving forward the wedge tip section 170 in which the motion is translated through shaft 134 via pivot barrel 142, turnbuckle 146, ball connection 148, through drive tube 150 and drive wire 154. In response, the upper member 170b of the wedge tip section 170 slides forward against hammer 172b deforming the sleeve member against anvil 170c to retain the suture. FIGS. 27B–27E illustrates the downwards movement of the hammer deforming on the sleeve member as the wedge tip section 170 is driven forward. The knife 170d at the lower member 170c of the wedge tip section 170 is also driven forward against the suture (FIG. 27F), to cut the ends of the suture near the sleeve member 174 (FIG. 27G). The operator then releases the actuator member 138 which automatically retracts in response to the forward bias by spring 140, and the wedge tip section 170 retracts releasing the sleeve member 174 from between hammer 172b and anvil 172c (FIG. 27H). The distal end 136 of suture instrument 130 is then removed leaving the crimped sleeve member 174a to retain the sutured tissue closed (FIG. 27I).

Figure 29A:
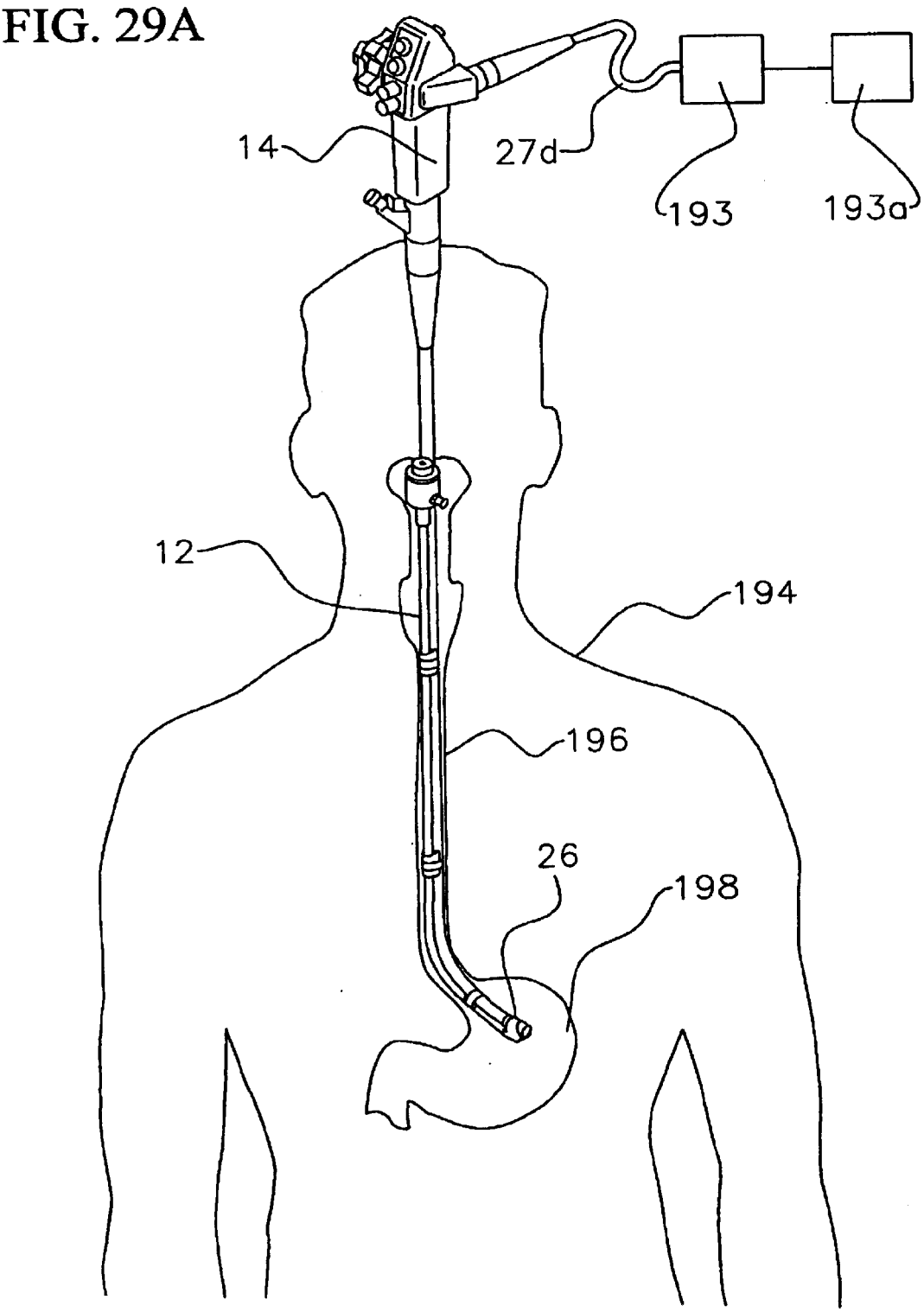
FIG. 29A is an example of the system of the present invention positioned in the gastroesophageal tract of a patient before insertion of the suturing instrument.
Figure 29B:
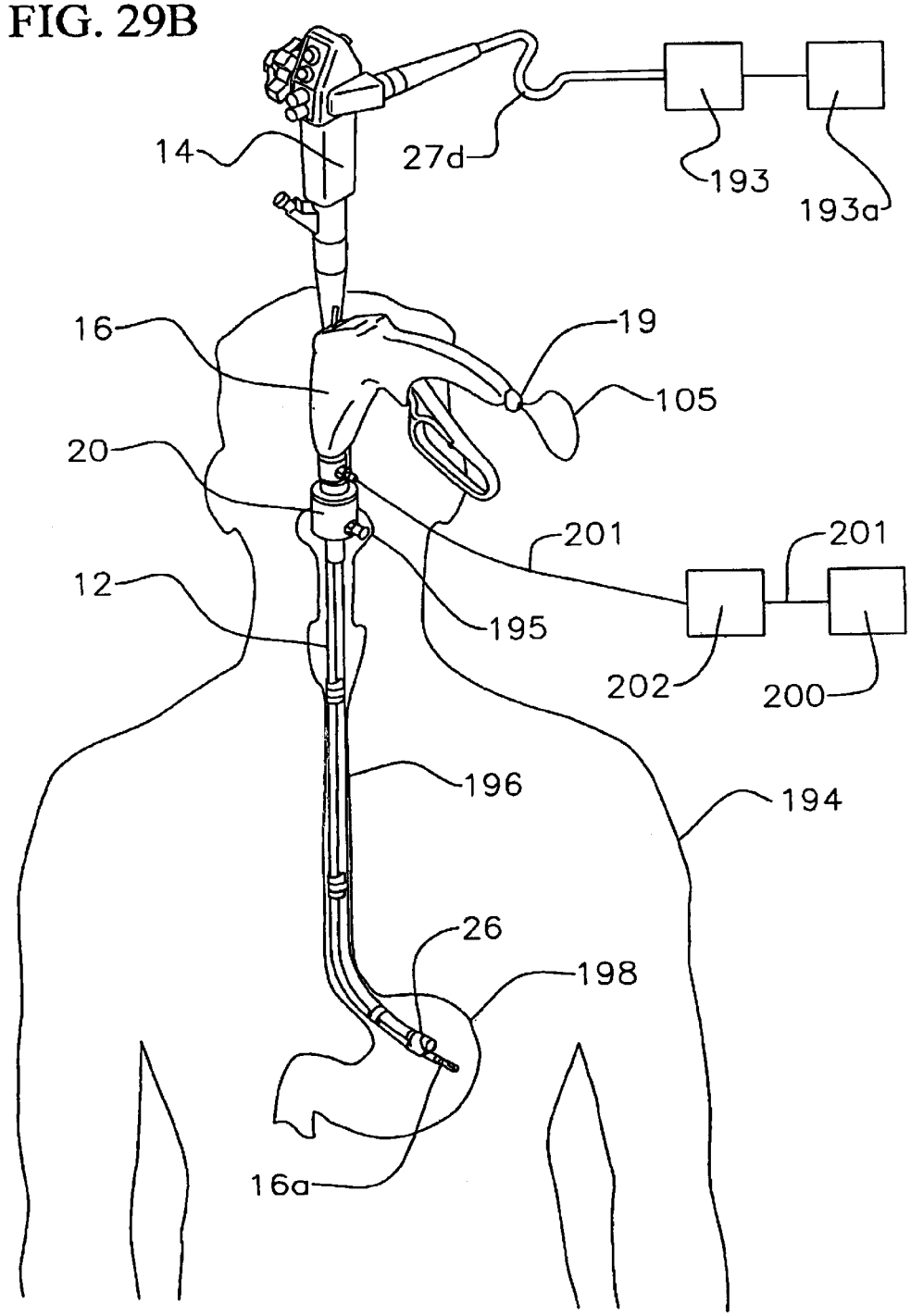
FIG. 29B is an example of the system of the present invention positioned in the gastroesophageal tract of a patient showing insertion of the suturing instrument through the accessory tube of the system.
Figure 29C:
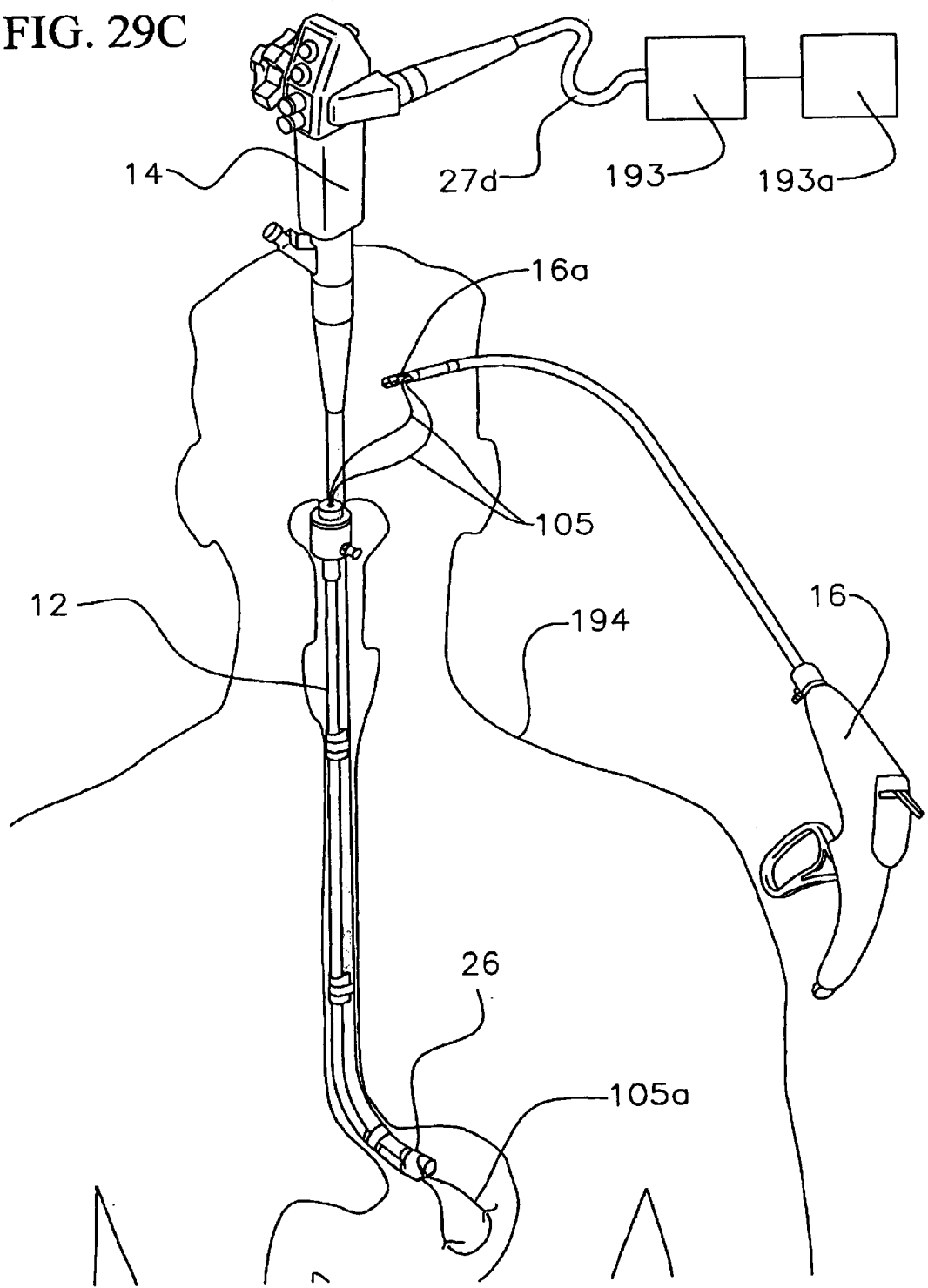
FIG. 29C is an example of the system of the present invention positioned in the gastroesophageal tract of a patient after placement of the suture thread and removal of the suturing instrument from the accessory tube of the system.
Figure 29D:
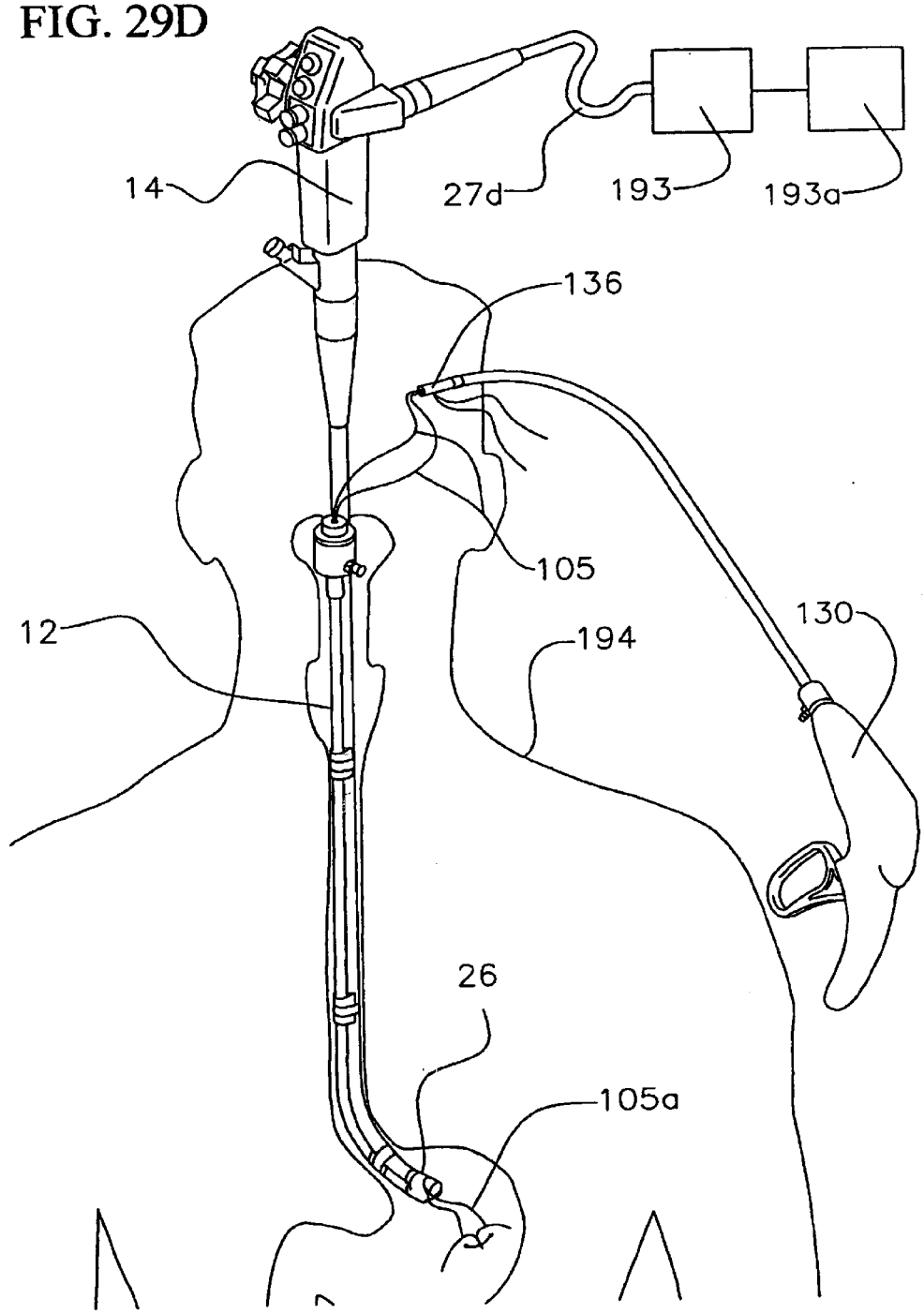
FIG. 29D is an example of the system of the present invention positioned in the gastroesophageal tract of a patient showing placement of the suture thread loop in the suture securing instrument.
Figure 29E:
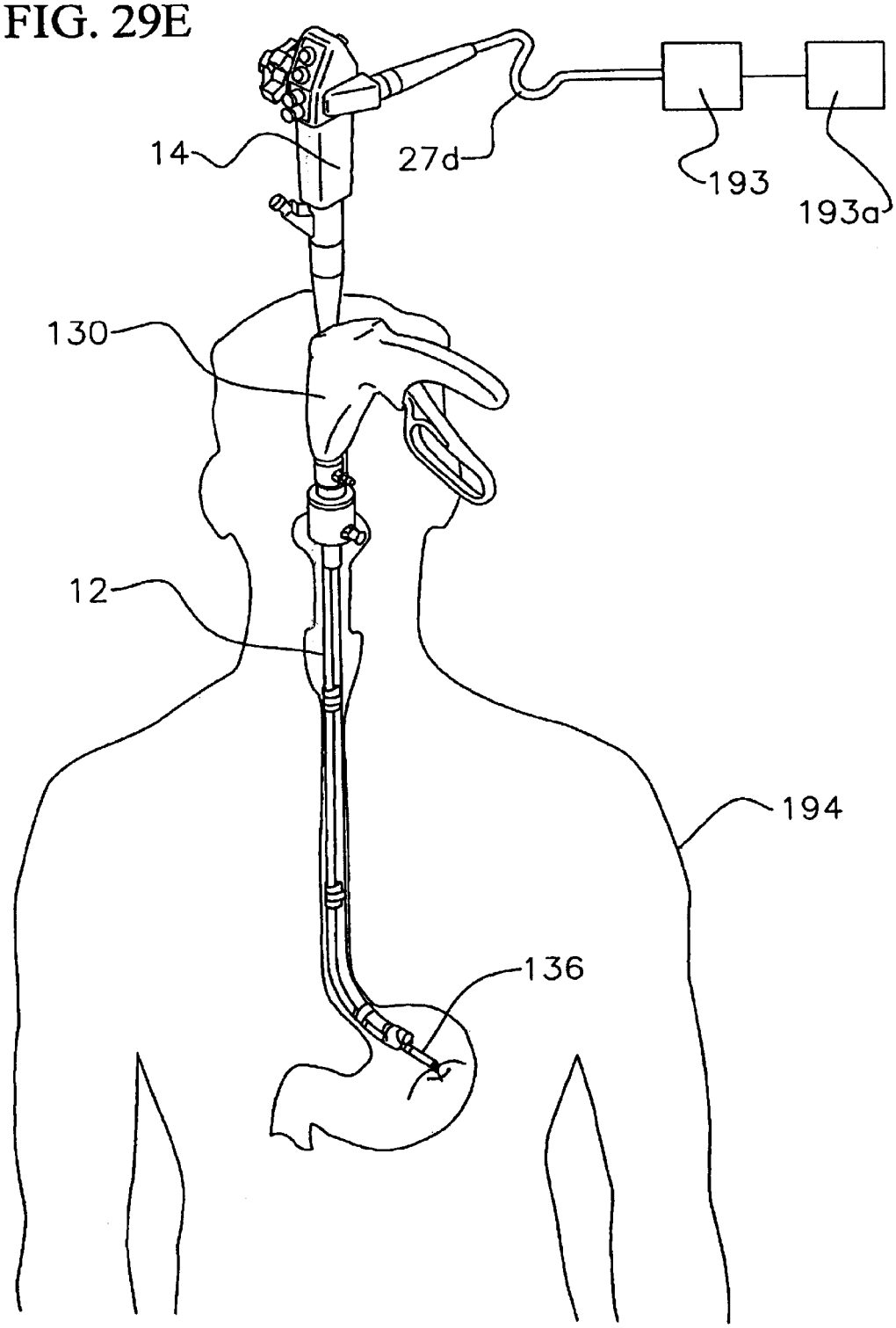
FIG. 29E is an example of the system of the present invention positioned in the gastroesophageal tract of a patient showing insertion of the suture securing instrument through the accessory tube of the system.
Figure 29F:
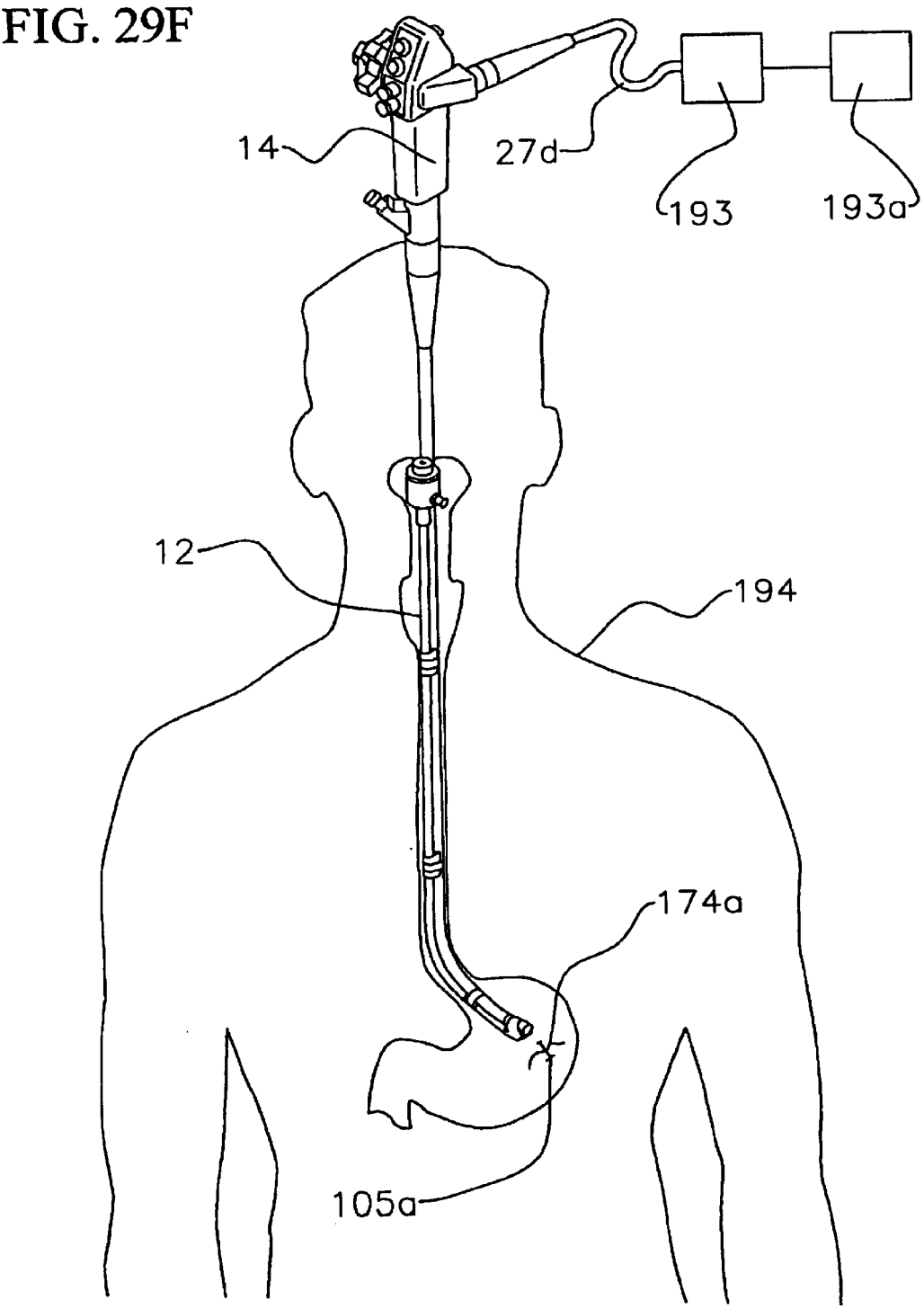
FIG. 29F is an example of the system of the present invention positioned in the gastroesophageal tract of a patient showing the secured suture remaining after removal of the suture securing instrument.
Figure 30:
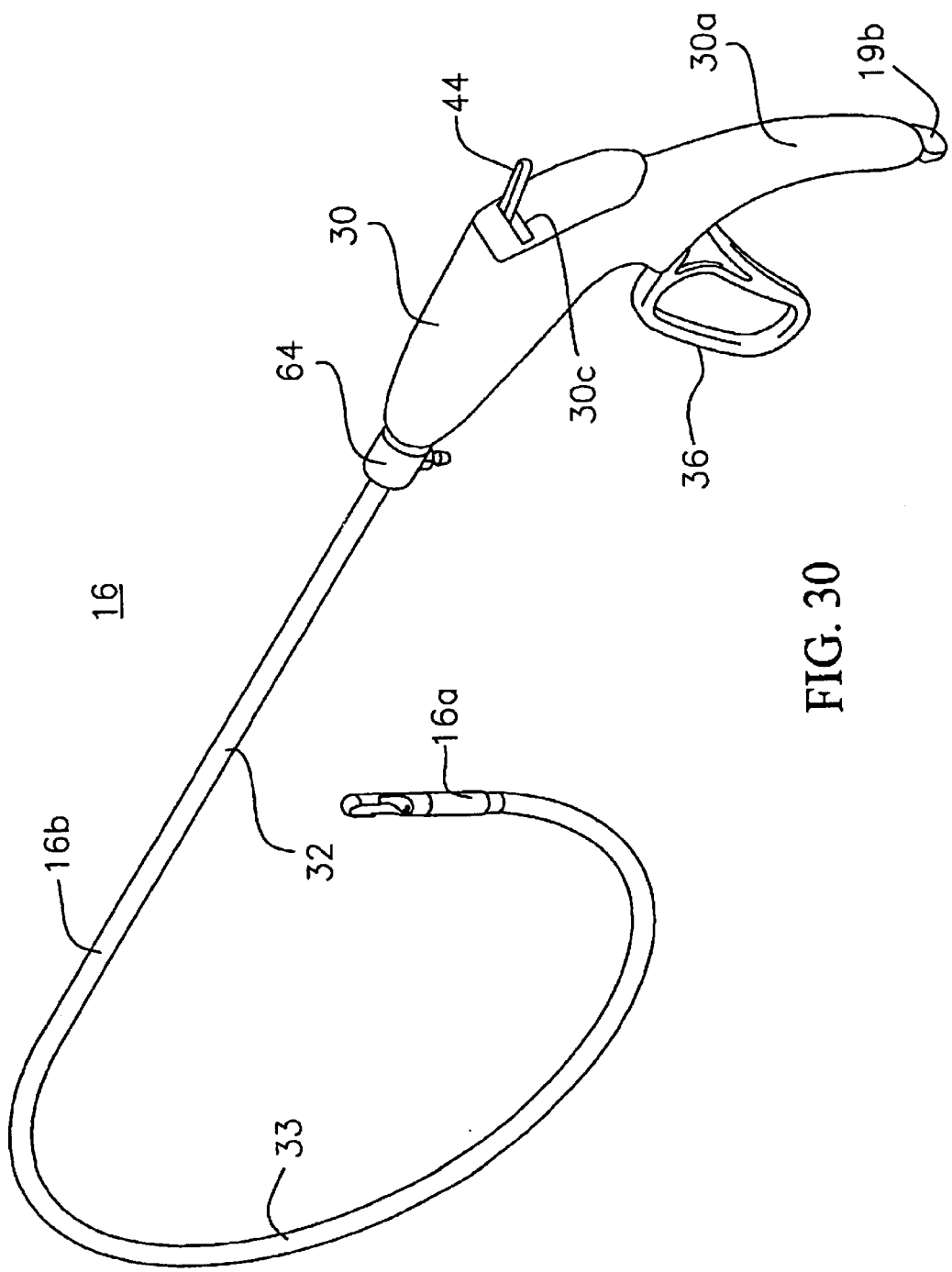
FIG. 30 is a perspective view of another embodiment of the suturing instrument in the system of FIG. 1 having enhanced flexibility.

Referring to FIGS. 28A–28M and 29A–29F the overall operation of system 10 will now be described in which FIGS. 28A–28M illustrate examples of the images on a display 193 provided by the gastroscope 14, and FIGS. 29A–29F illustrate the relative position of the gastroscope 14, accessory tube 12, and instruments 16 and 130 during suturing and suture securing. With the patient 194 ready for the procedure, the gastroscope 14 and attached accessory tube 12 are inserted through the mouth 195 down the esophagus 196 and into the stomach 198 where the suturing will take place (FIG. 29A). The suturing instrument 16 with a loop of suture 105 loaded is then inserted into the accessory tube 12 via cannula 20, until the distal end 16a passes through attachment tip 26 (FIGS. 28A and 29A). The tissue engaging end 16a of the suturing instrument 16 is viewable to the operator on display 193 through the gastroscope (FIG. 28A). With the target area of the tissue located, the valve 19 is closed, and suction is applied to instrument via a vacuum source 200 and control (or regulator) 202 via tubing 201 to pull the tissue into gap 104 of sew tip 98, as described earlier (FIG. 28B). Control 202 may be integrated in vacuum source 200 or along tubing 201, and is used to selectably enable and disable suction to the sew tip 98 in vacuum sleeve 106. A first one of needles 34 or 35 is then extended and retracted by the operator, as described earlier, to locate the first end of the suture in the tissue. The suction is then disabled, valve 19 opened, and the sew tip is lifted leaving the suture extending through the tissue (FIGS. 28C, 28D, 28E, and 28F). The target area for the second end of the suture is then located, valve 19 closed, and vacuum again enabled to pull the tissue into the sew tip 98 (FIG. 28F). A second one of needles 34 or 35 is extended and retracted to locate the second end of the suture in the tissue. The suction is then disabled, valve 19 opened, and the sew tip lifted leaving the suture extending through the tissue. FIG. 28G shows an image of the first and second ends of the suture in the tissue. The suturing instrument 16 is then removed from the accessory tube as shown in FIG. 29C, pulling a loop 105a of suture 105 through the stomach tissue (FIGS. 28H–28J). The ends of the suture material are cut from the suturing instrument 16 and then loaded through the suture securing instrument 130 which has been loaded with a sleeve member 174, as shown in FIG. 29D. The suture securing instrument 130 is then inserted into the accessory tube 12 while gentle tension is applied to the free ends of the loop of suture (FIG. 28K). The distal end 136 of the suture securing instrument passes through the attachment tip 26 and is located near the suture loop extending from the tissue (FIG. 28L). The suture securing instrument 130 is positioned adjacent to the tissue, appropriate suture tension applied and the instrument is then actuated as described earlier to crimp and cut the sleeve member (FIG. 28M), and then the instrument 130 is removed leaving the crimped sleeve member 174a to close the suture (FIG. 28N). FIG. 29F illustrates the patient after the suture is closed and the suture securing instrument is removed. The gastroscope 14 and attached accessory tube 12 remains in the patient during both the suturing and suture securing operations, and this procedure does not require the use of an overtube. If additional suturing is required, the suturing instrument 16 may be reloaded with another suture loop and above described procedure repeated with the suture securing instrument reloaded with another sleeve member to secure the suture closed. In this manner, multiple sutures may be made in the stomach tissue with a single insertion of the gastroscope 14. When suturing is completed, the gastroscope 14 and attached accessory tube 12 are removed from the patient.

Although the suturing instrument 16 and suture securing instrument 130 are described for use with gastroscope 14, instruments 16 and 130 may be used separately from the gastroscope 14 and accessory tube 12. Further, suturing instrument 16 and suture securing instrument 130 may pass through an internal channel 28d (FIG. 1B), often called a working or biopsy channel, provided in gastroscope 14 to its distal end 14a sized to receive the respective shaft of the instrument.

Figure 31:
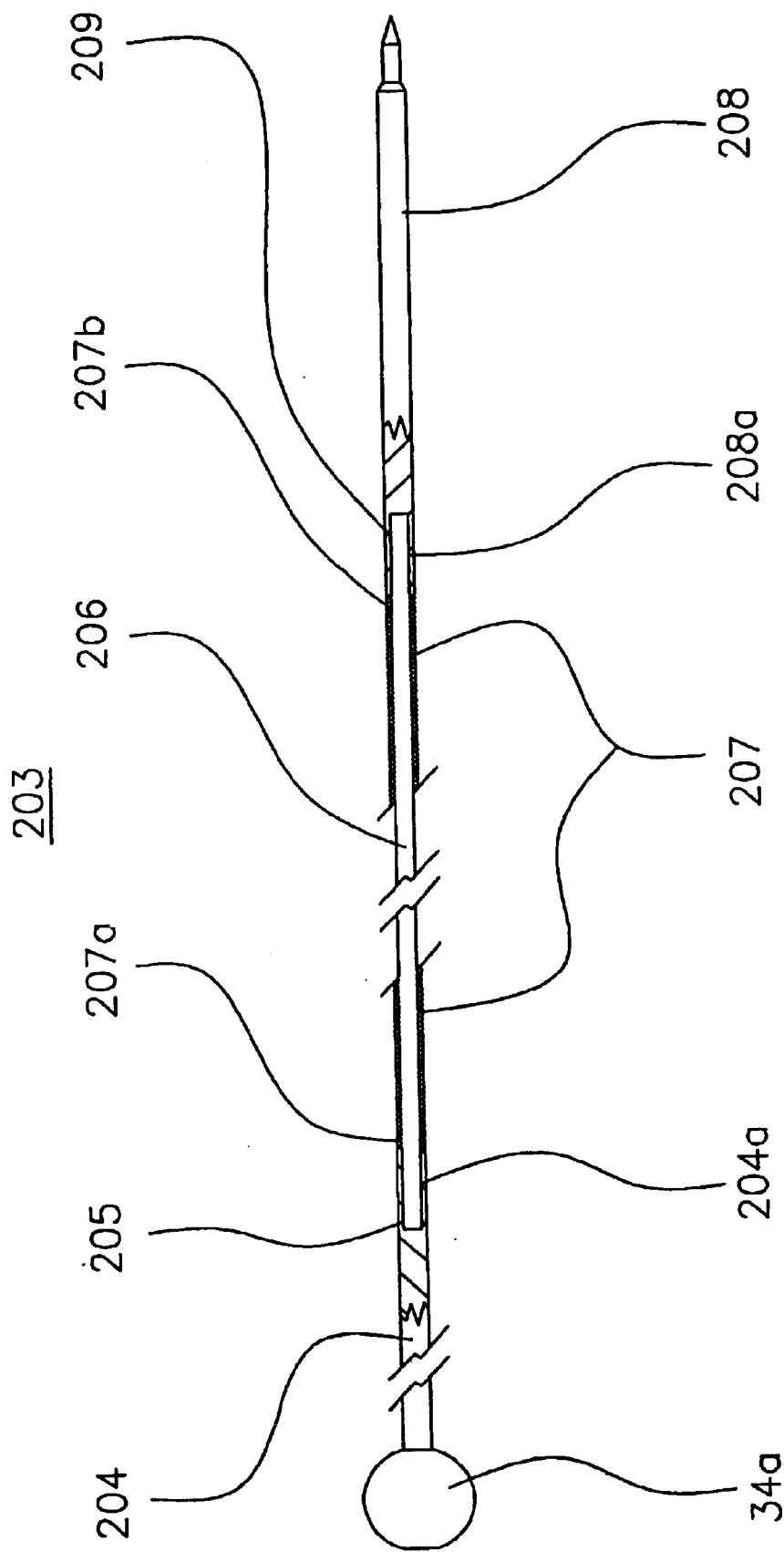
FIG. 31 is a schematic diagram of the needle assembly for each of the two needles in the embodiment of the suturing instrument of FIG. 30.

Referring to FIGS. 30–35, another embodiment of the suturing instrument 16 is shown to provide additional flexibility within section 33 of shaft 16b of the instrument. This additional flexibility facilitate further freedom for section 33 to flex in the accessory tube 12 with the flexing of gastroscope shaft 14a in positioning the distal end 14b of the gastroscope. Suturing instrument 16 is the same in this embodiment except for the components in section 33 between coupler member 56 and sew tip 98. Needles 34 and 35 in this embodiment are illustrated in FIG. 31 as needle assembly 203. For illustration purposes, needle assembly 203 for needle 34 is shown, since needles 34 and 35 are identical. A needle driver 204 is coupled to ball 34a by welding or braising into a hole in the ball. Needle driver 204 is a stainless steel wire or tube. A cable 206 is received in a hole 205 in one end 204a of needle driver 204. A spring 207 is installed at one end 207a over the cable 206 and attached, such as welded or crimped, to end 204a of the needle driver 204. The other end of cable 206 is received in a hole 209 at end 208a of needle 208, and the end 207b of spring 207 is attached such as welded or crimped, to end 208a of the needle. Cable 206 is a stainless steel wire or braided cable. Spring 207 is a stainless steel extension spring which is normally compressed, and has an inner diameter slightly larger than the outer diameter of cable 206. For example, inner diameter of spring 207 may be 0.020 inches, and the outer diameter of cable 206 maybe 0.018 inches. The outside diameter of spring 207 may be matched to the outside diameters of needle driver 204 and needle 208. The length of needle driver 204, needle 208, and cable 206 in spring 207, is such that the tip 122 of the needle 208 lies in the sew tip 98 when the needle is fully retracted.

Figure 32:
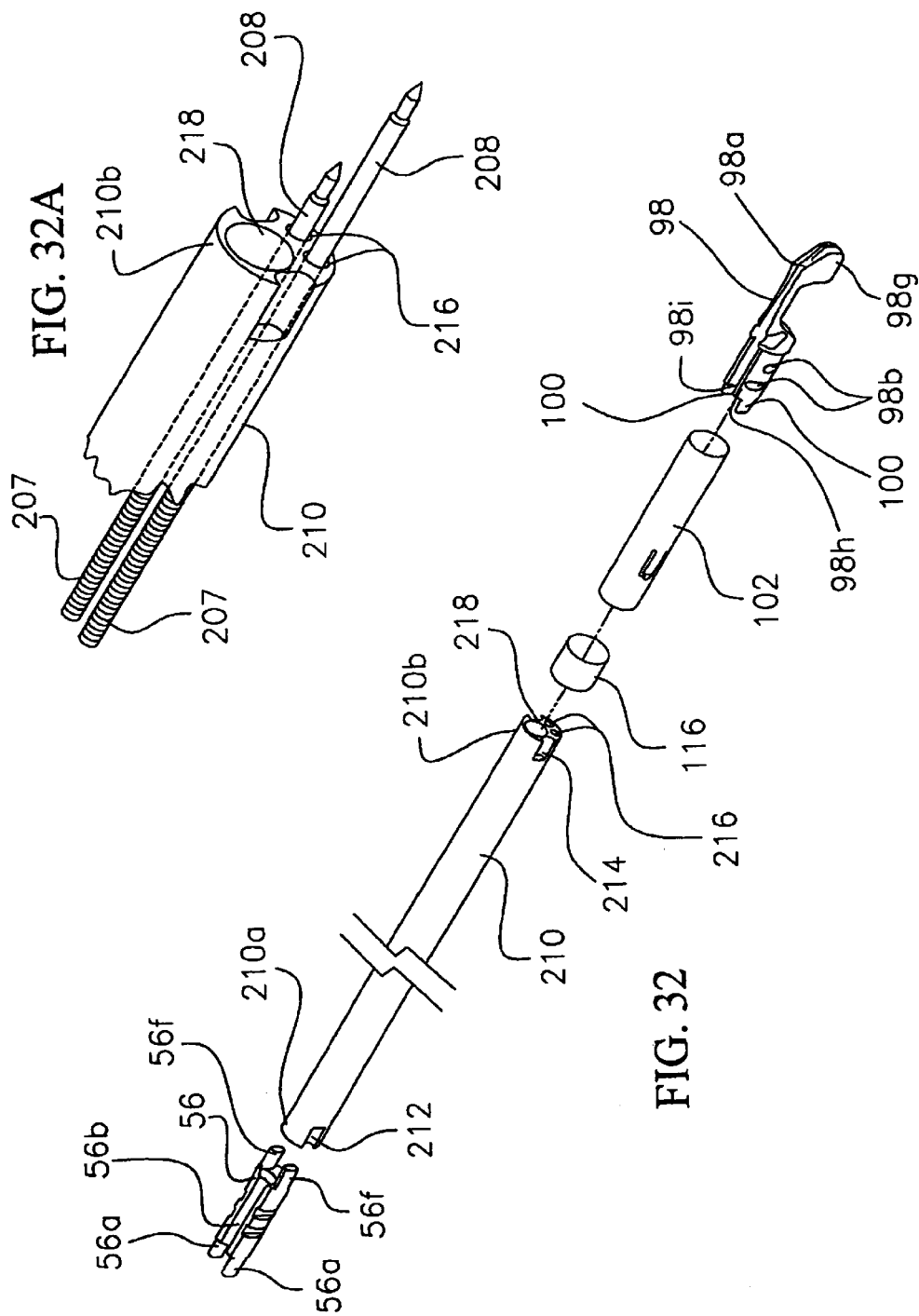
FIG. 32 is an exploded view of the coupler member, sew tip, and multi-lumen tube in the embodiment of the suturing instrument of FIG. 30 in which the needles are removed.

Needle assembly 203 for each of needles 34 and 35 extends through a multi-lumen tube 210 which is attached at end 210a to coupler member 36 by tabs 56f being received in corresponding pockets 212 at end 210a, and is attached to sew tip 98 by tabs 100 of sew tip 98 in pocket 214 at end 210b. For purposes of illustration, needles are not shown in FIG. 32. Multi-lumen tube 210 is made of flexible material, such as plastic, polyurethane, or pebex, and has two holes 216 through which needles 34 and 35, respectively, each extend, as best shown in FIG. 32A, where the spring 207 and needle 205 are shown through holes 216. The holes 216 have a diameter slightly larger than the outside diameter of the spring 207. The tube 210 is longitudinally reinforced, such that it cannot be substantially stretched or elongated. Such longitudinally reinforcement of the tube may be provided by a stainless steel kevlar, or nylon weave installed in the tube when it is extruded, or the weave may be adhesively bonded to the outer surface of tube 210. A suture hole 218 extends through tube 210 for passage of suture, and negative or positive air pressure, similar to hole 58d of guide member 58. End 204a of needle driver 204 and end 208a of needle 208 are located in tube 210 for each needle in holes 216. Attachment of tip tube 102, ring 116, and sew tip 98 is the same as described earlier.

The operation of suturing instrument 16 in this embodiment is the same as described earlier, except that when actuator member 36 of instrument 16 is pulled by an operator for needle 34 or 35, forward movement is translated to needle 208 via needle driver 204 and spring 207, which compresses to assist in pushing forward needle 208 in sew tip 98. When actuator member 36 is retracted, the cable 206 and spring 207 assist in pulling needle 208 back.

Figure 33:
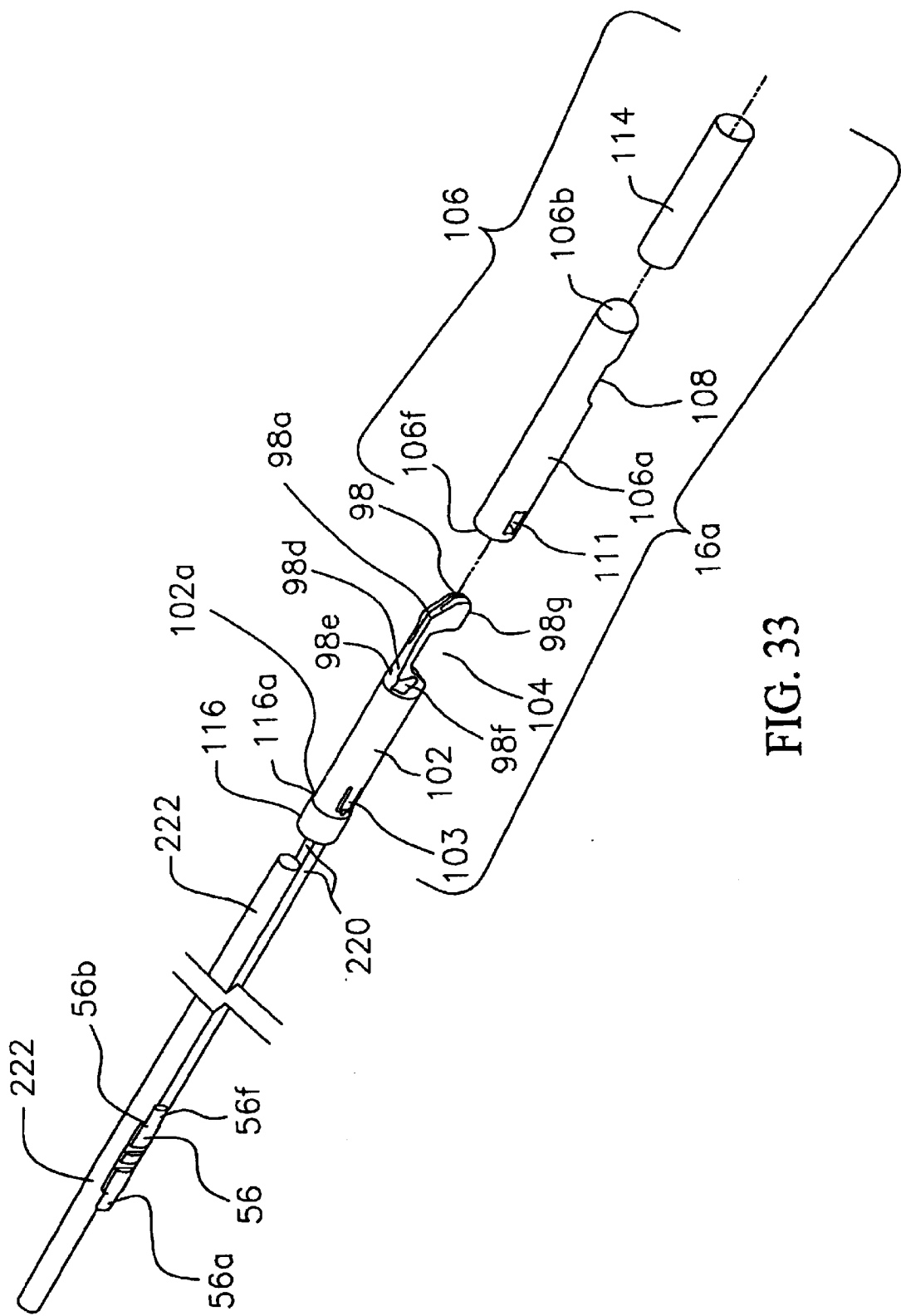
FIG. 33 is an exploded view of coupler member and sew tip of the embodiment of the suturing instrument of FIG. 30 in which the multi-lumen tube of FIG. 32 is replaced by two needle carrying tubes and one suture supply tube.
Figure 34:
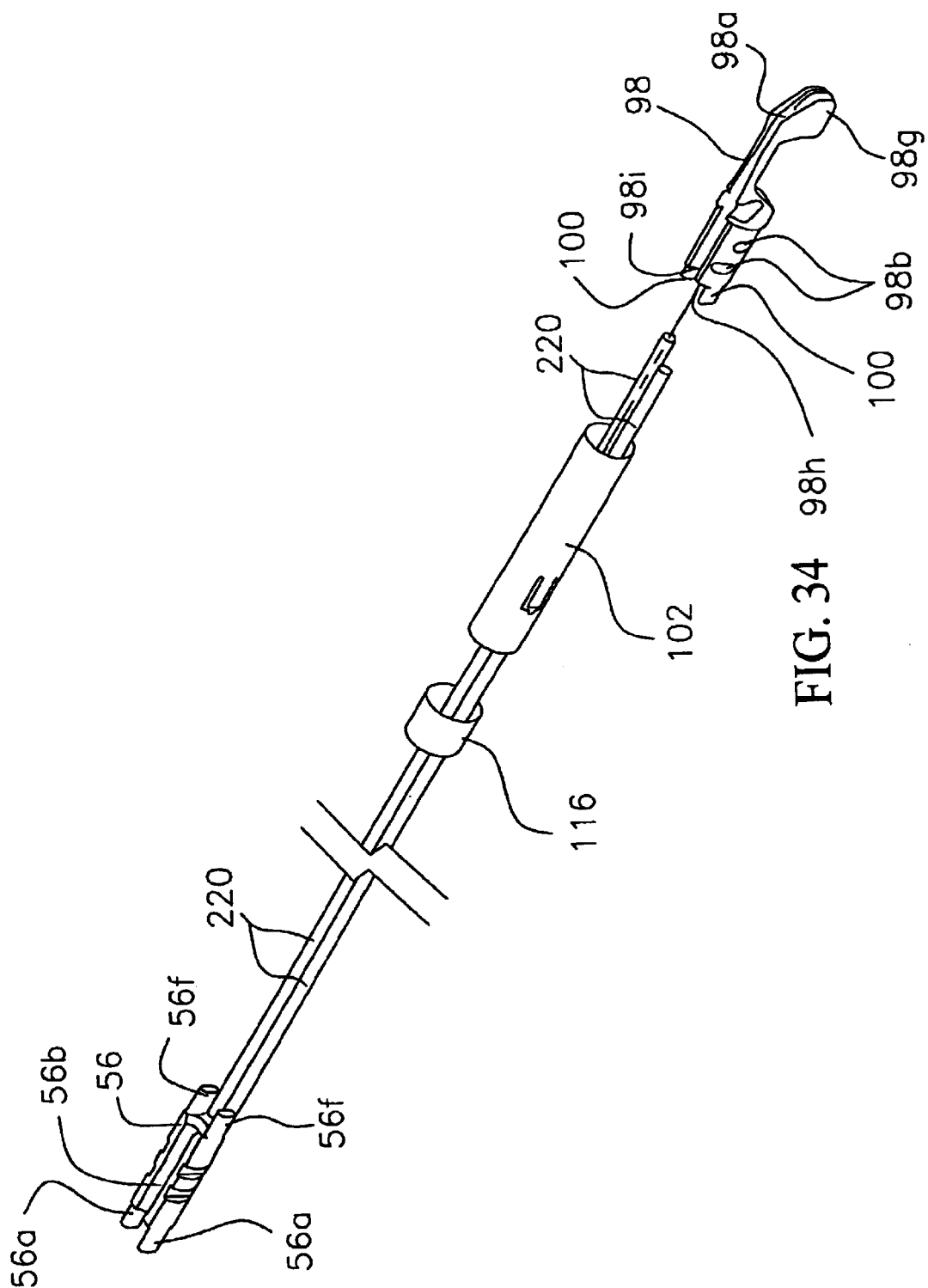
FIG. 34 is an exploded view similar to FIG. 33 showing in more detail the needle carrying tubes of FIG. 33.
Figure 35:
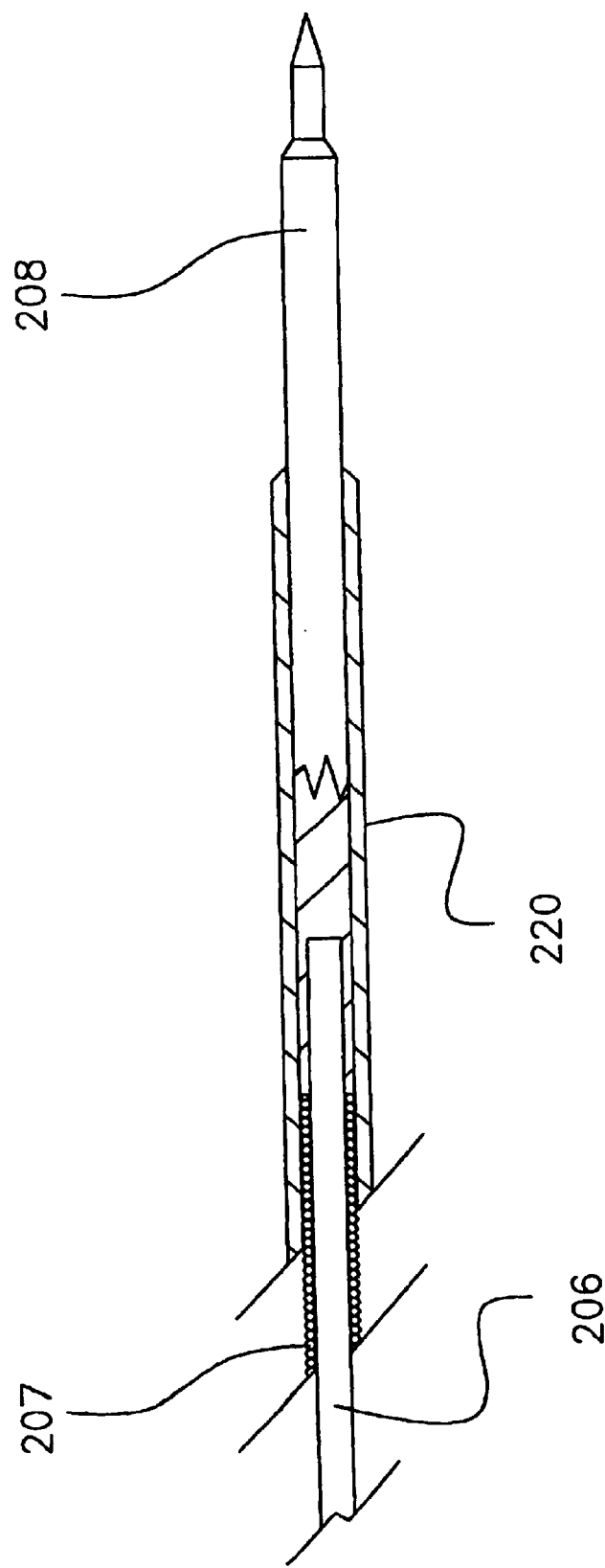
FIG. 35 is a schematic diagram of the needle assembly of FIG. 31 extending through one end of a needle carrying tube of FIG. 33.

Alternatively in this embodiment, the multi-lumen tube 210 may be replaced by needle carrying tubes 220 and suture supply tube 222. The needle assembly 203 for each of needles 34 and 35 extends through tubes 220, respectively, as shown in FIGS. 33 and 34, while the suture supply tube 222 provides a path for suture to sew tip 98, and also can provide negative (or positive) air pressure, as described earlier via vacuum connection assembly 64. Supply tube 222 extends from chamber 66b of vacuum connection assembly 64 through hole 53c of guide member 53, through suture track 56b of coupler member 56, and then along flexible shaft section 35 to sew tip 98. Tubes 220 and 222 may be made of flexible stainless steel tubing or reinforced plastic, pebex, or polyurethane tubing, or nickel titanium tubing, such as nitnol. FIG. 35 shows needle assembly 203 at one end of tubing 220. In this embodiment, shrink wrap 62 (FIG. 10) covers multi-lumen tube 210, or tubes 220 and 222 if no multi-lumen tube is used, such as described earlier for guide member 58. Optionally, to enhance needle carrying tubes 220 flexibility, the tubes 220 may each represent a wound spring 234 with outer sheath 236, such heat shrink tubing, on the outside surface of the spring 234, as shown in FIGS. 35A and 35B. The interior diameter of the spring 234 is slightly greater than the outside diameter of needle assembly 203 extending there through. The outer sheath 236 is shrunk to the spring only at the ends 234a and 234b of the spring 234, such that elongation of spring 234 is restricted. The interior diameter of outer sheath 236 is larger than outside diameter of spring 234 to allow flexure of spring 234.

Figure 36:
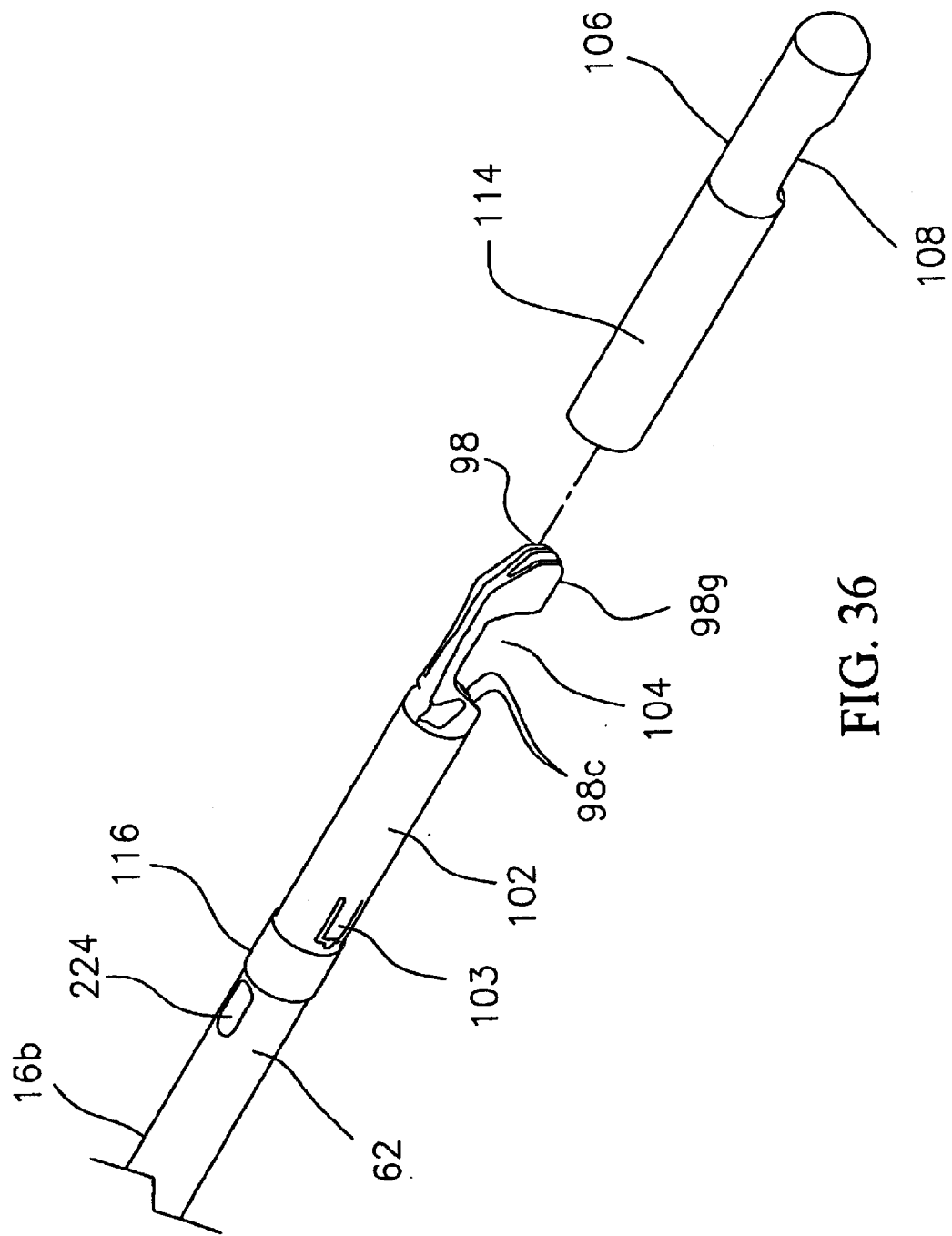
FIG. 36 is an exploded view of the tissue engaging end of a further embodiment of the suturing instrument of the system of FIG. 1 in which the vacuum connection assembly of the instrument is not required.
Figure 36A:
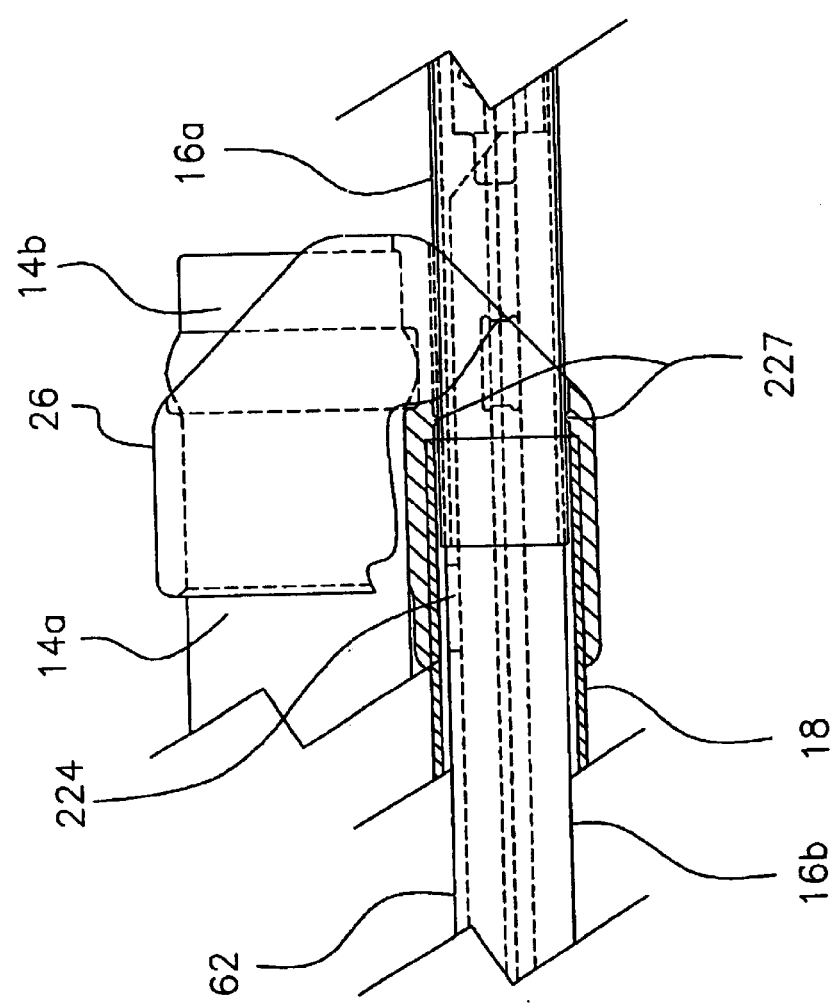
FIG. 36A is a side view of the tissue engaging end of the suturing instrument of FIG. 36 with the attachment tip partially broken away.

Referring to FIGS. 36 and 36A, a further embodiment of suturing instrument 16 is shown in which suction to the sew tip is provided without vacuum connection assembly 64. In this further embodiment, both the vacuum connection assembly 64 and opening 52c to rigid tube 52 is removed, and an opening 224 is provided through the shrink wrap 62 to suture track 58c of guide member 58. An additional ring seal 227 (FIG. 36A) is provided in the opening 26b extending through attachment tip 26. Ring seal 227 is composed of the same material as attachment tip 26, and represents a ring extending from the interior surface of the opening 26b having a diameter slightly smaller than the largest diameter of tissue engaging end 16a. The tissue engaging end 16a can pass through the seal 227, while ring seal 227 engages the outer diameter of the tissue engaging end. Suction may then be applied via cannula port 20e (FIG. 6) of the accessory tube 12 and communicated through opening 224 to the suture channel, i.e., suture track 58c and channel 98d to cavities 98f gap 104 of the sew tip 98, as described earlier, when instrument 16 is located through accessory tube 12. This suction may be provided from vacuum source 200 (FIG. 29B) through controller unit 202 and tubing 201 to port 20e, rather than to the vacuum connection assembly 64.

Figure 37:
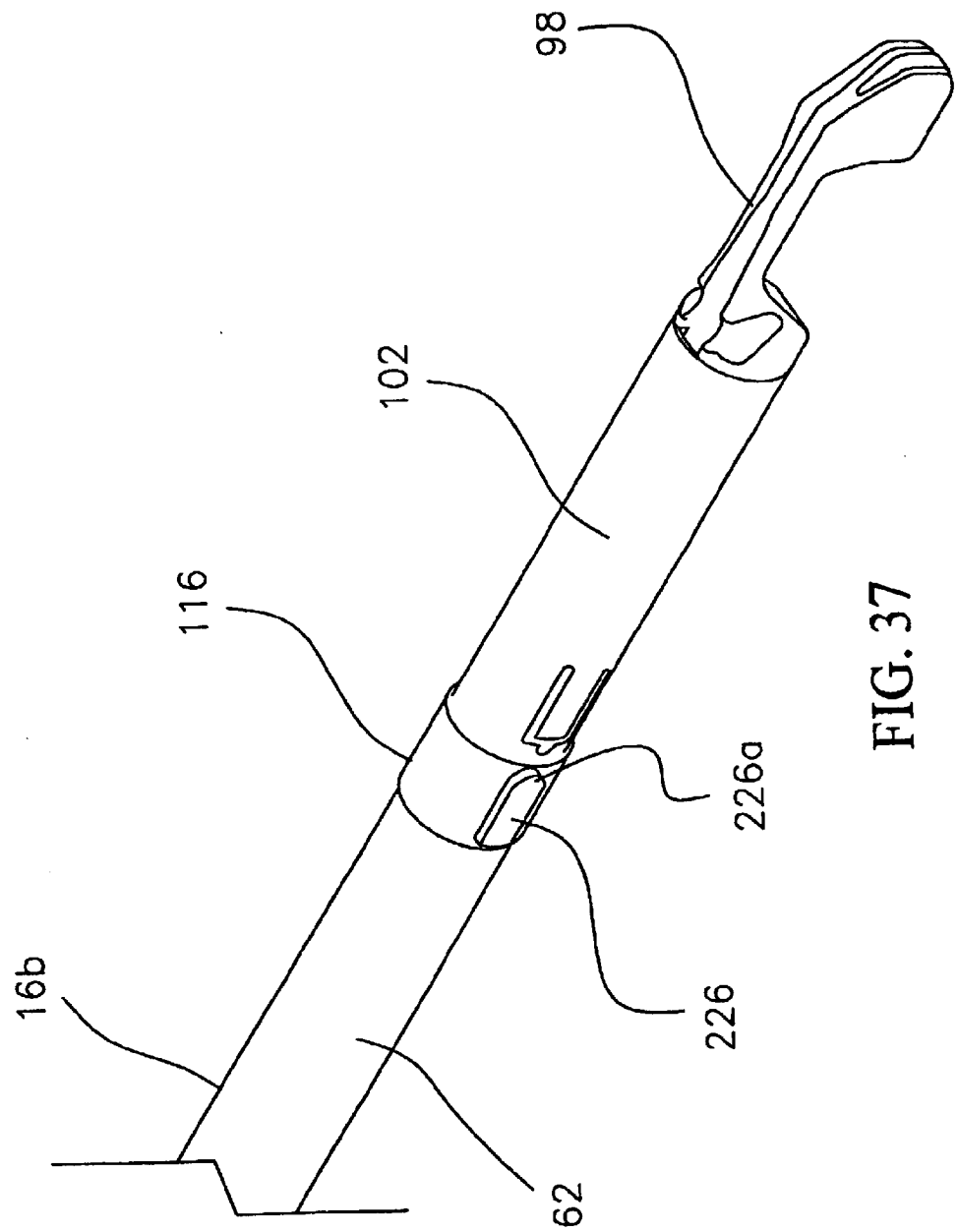
FIG. 37 is a perspective view of the tissue engaging end of the suturing instrument of the system of FIG. 1 without a sleeve to provide rotational locking of the tissue engaging end in the attachment tip of the accessory tube.
Figure 38:
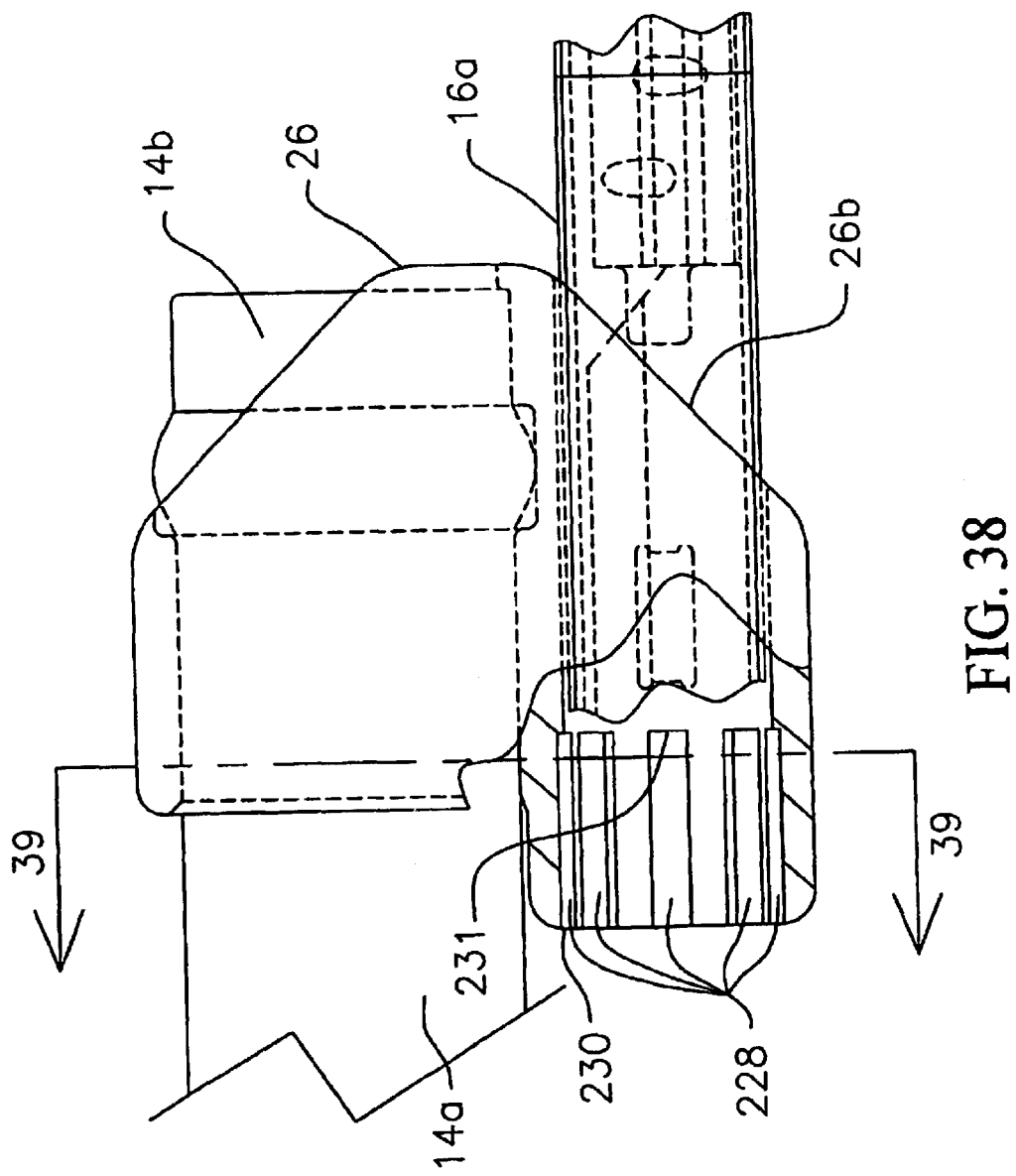
FIG. 38 is a side view of the attachment tip of the accessory tube to provide rotational locking with the tissue engaging end of the suturing instrument of FIG. 37, in which the interior of the attachment tip is partially broken away to show the slots into which the tissue engaging end can engage.
Figure 39:
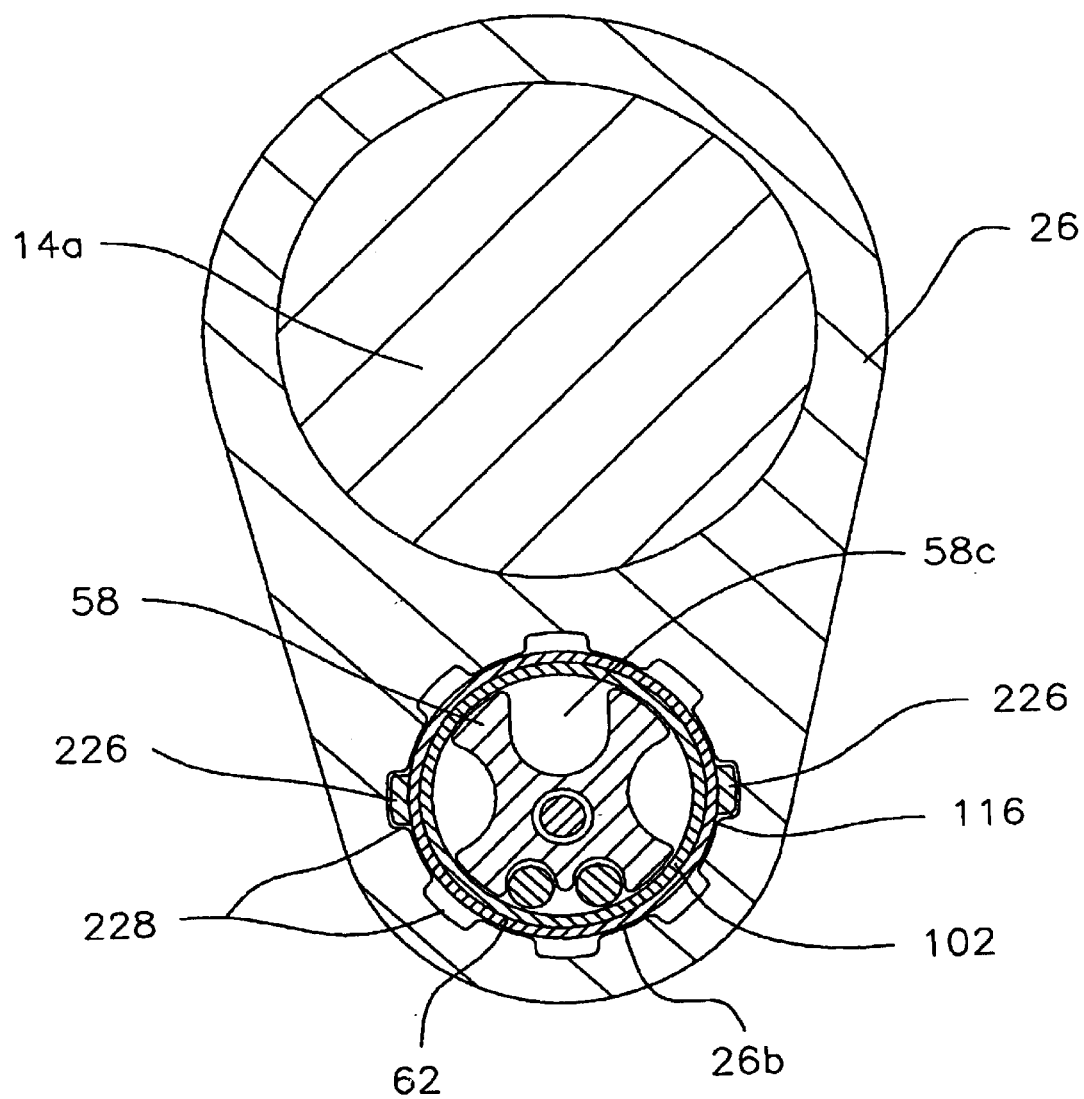
FIG. 39 is a cross-sectional view along lines 39—39 of FIG. 38.

Referring to FIGS. 37–39, system 10 may optionally have positional locking of tissue engaging end 16a to lock the rotational position and to limit forward longitudinal travel of the tissue engaging end 16a of the suturing instrument in attachment tip 26 of the accessory tube 12. Such locking is provided by adding one or more protrusion members 226 to ring 116 of tissue engaging end 16a. For example, ring 116 may have two protrusion members located 180° apart along the outer circumference of ring 116. These protrusion members 226 may be made of stainless steel or molded from plastic, and attached, such as adhesively bonded, or if medal by welding or brazing, to the outer surface of ring 116. Protrusion members 226 are shaped to be received by slots 228 in opening 26b extending through attachment tip 26. For example, eight slots 228 are provided at 30 degree increments about the interior surface of opening 26b, such that two protrusion members 226 may be received in one of four opposing (180° apart) pairs of slots 228. Lesser or greater numbers of slots may also be provided. Each slot 228 extends from end 230 of attachment tip 26 partially into opening 26b to provide a stop 231. The height of the protrusion member 226 from the outer surface of ring 116 is slightly less than the depth of the slots 228, and width of the protrusion members 226 is slightly less than the width of slots 228, such that protrusion members 226 can easily engage with an opposing pair of slots 228. Protrusion members 226 each have a forward round-shaped end 226a that facilitates the alignment of the protrusion members 226 in slots 228 to limit instrument 16 rotation and forward travel.

In operation, when the tissue engaging end 16a of the instrument 16 passes through accessory tube 12 and through the attachment tip 26, the distal end 14a of the gastroscope 14 can view the vacuum sleeve, and partially the sew tip therein, prior to engagement of protrusion members 226 in a pair of opposing slots 228. The operator then can precisely locate the position of gap 104 of the sew tip with respect to a tissue target area 121 (FIG. 22B), as described earlier. With the target area located and sew tip gap 104 aligned to face the target area, and substantially parallel thereto, the operator slightly rotates the instrument at housing 30, such by handle 30a, and pushes the instrument to locate and engage the protrusion member 226 of ring 116 of the tissue engaging end 16a in the closest pair of opposing slots 228 in opening 26b of the attachment tip 26 which corresponds to the desired aligned rotational position of the sew tip's gap 104 with respect to the tissue target area, until protrusion members' end 226a abut stop 231. Once the tissue engaging end 16a is so rotationally locked in position, the risk of rotational misalignment of the sew tip gap 104 when tissue is captured therein is reduced. To select another target area 126 (FIG. 22F), the operator rotationally unlocks tissue engaging end 16a by pulling the instrument handle 30 slightly back which disengages the protrusion members 226 from slots 228.

Figure 40:
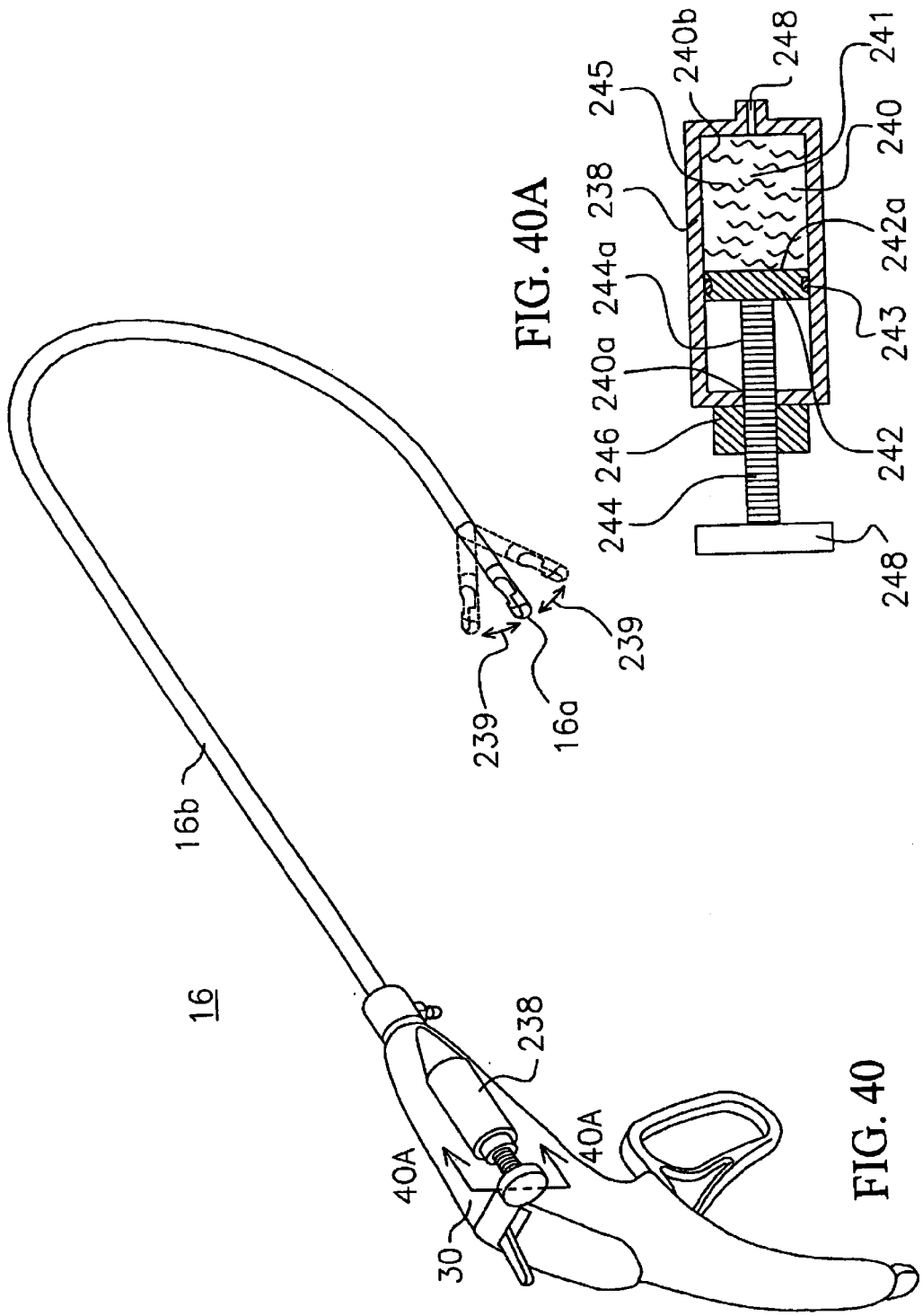
Figure 41:
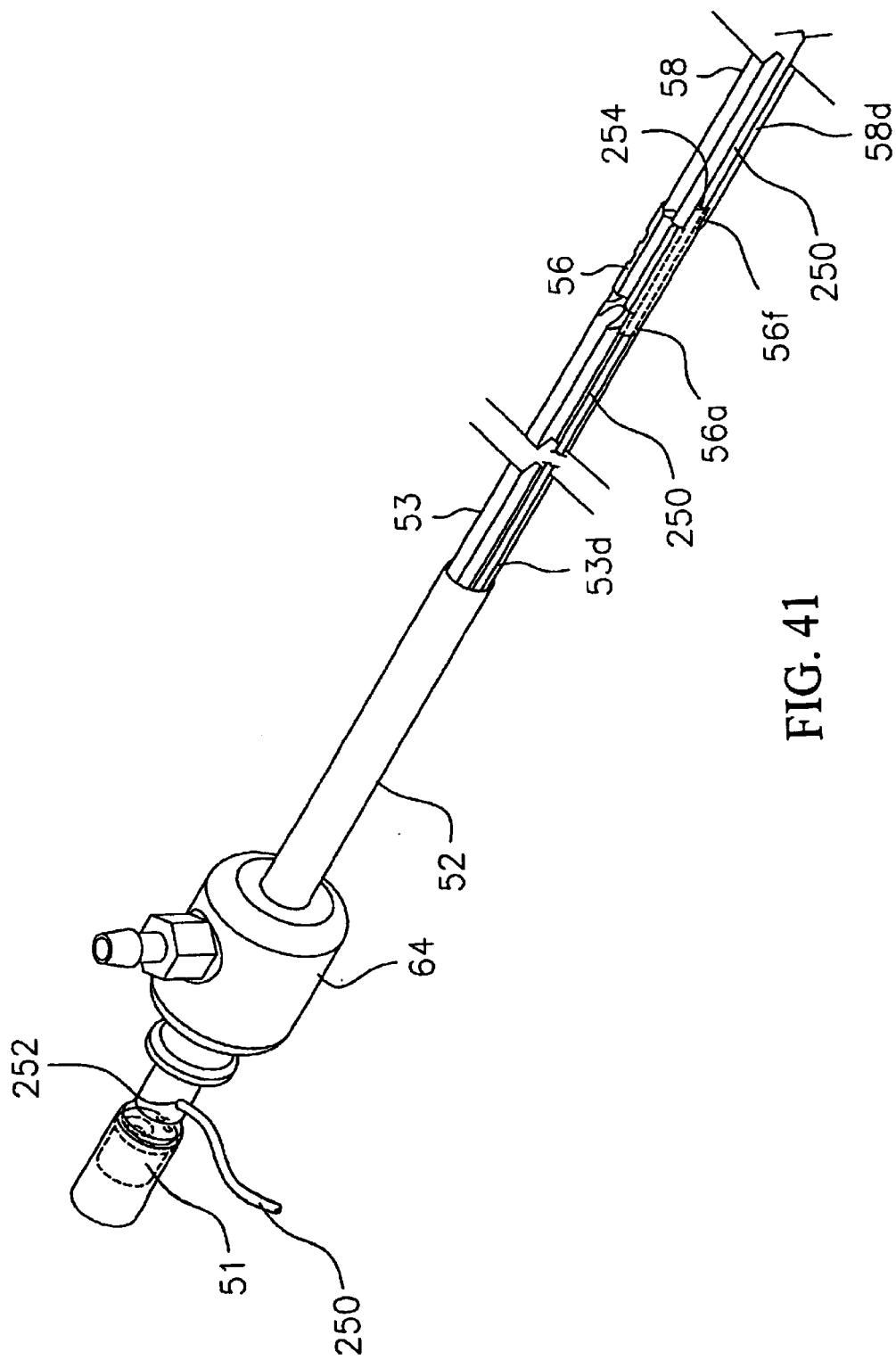
Figure 43A:
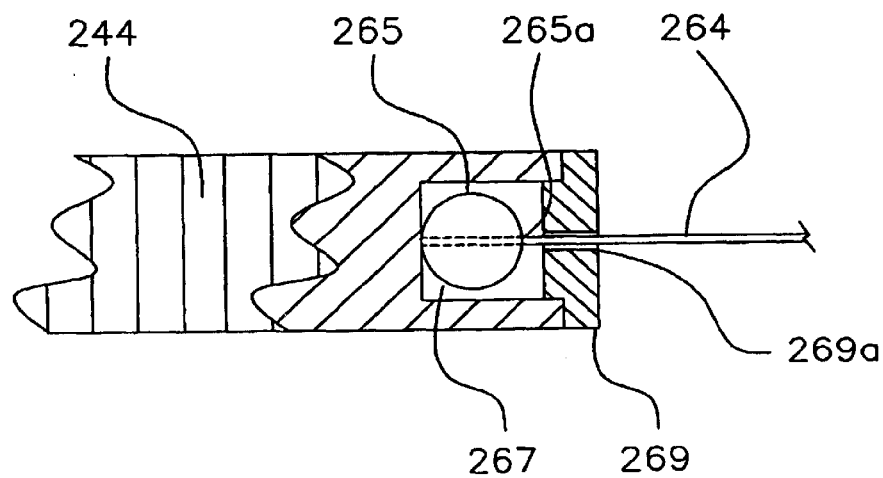
Figure 43:
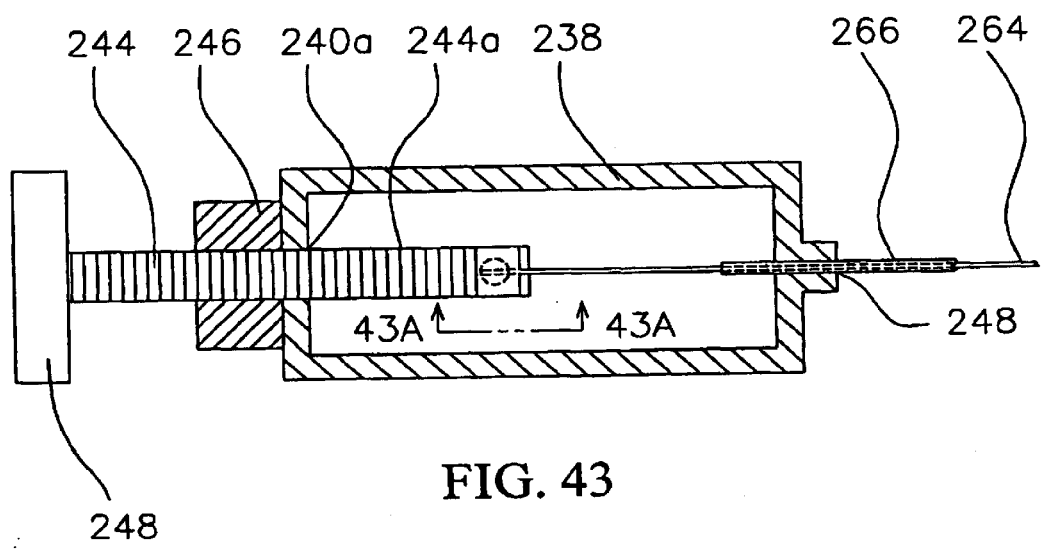

Referring to FIGS. 40, 40A, 41, 42, and 42A, optionally the suturing instrument 16 may have a steering mechanism for flexing needle engaging end 16a. This steering mechanism includes a control cylinder 238 having walls defining an interior chamber 240 having therein a plunger or piston 242 attached to the end of a threaded shaft 244a, which is held in the chamber 240 by a threaded nut 246 (FIG. 40A). The threaded nut 246 is attached to the chamber 240 by insert molding. A thumb wheel 248 attached to the turn screw 244 enabled the shaft 244a of the turn-screw to rotate along threaded nut 246 and control the position of the piston 242 in chamber 240. Piston 242 has a rubber ring seal 243 which engages the interior surface 240b of chamber 240. An opening or outlet 248 at one wall of chamber 240 provides a flow path for the volume 241 of liquid 245 contained in the chamber 240, where this volume 241 is defined by the surface 242a of the piston 242 facing opening 248 and the interior surface 240b of the chamber 240.

As shown in FIG. 40, at least one exterior surface of a wall of control cylinder 238 is molded into housing 30, or the control cylinder 238 is applied by adhesive to the outer surface of housing 30. Shaft 244a and nut 246 may be made of stainless steel, while walls of chamber 240, piston 242 and thumb wheel 248 may be made of plastic, such ABS. In housing 30, a flexible tube 250 is coupled at one end to outlet 248 and extends through an opening 252 located in the rigid tube 52 after gasket member 51 and before vacuum connection assembly 64, and then tune 250 follows a path along one of tracks 53d of guide member 53 in rigid tube 52, and through a hole 254 of coupler member 56 extending through its tab 56a and 56d (as shown in dashed lines in FIG. 41). From coupler member 56, the tube 250 extends along one of tracks 58d of guide member 58 to a cylinder 256 located in the track 58d before sew tip 98 (FIG. 42). For example, tube 250 may be made of flexible plastic material. As shown in FIG. 42A, cylinder 256 has walls defining a interior chamber 256a having an opening 256b in one wall to this chamber which the other end of tube 250 is connected, such as by adhesive bonding. A piston or plunger 256c in chamber 256a is coupled to a rod 258 extending through an opening 256d in a wall of the chamber. The surface 256e of piston 256c faces opening 256b and is positionable in chamber 256a to change the volume 257 of liquid 245 contained in the chamber, where volume 257 is defined by surface 256e of the piston 256c and the interior surface 256f of cylinder 256.

Rod 258 has at its end 258a a hole 258b into which a flexure member 260 is attached, such as by welding or crimping. Flexure member 260 extends into a hole in one end of tabs 100 of sew tip 98, and is attached thereto by welding or crimping. Flexure coupler 260 allows for possible misalignment between rod 258 and tab 100 of the sew tip 98. Cylinder 256 is fixed in place in one of tracks 58d, such as by frictionally engagement when shrink wrap tubing 62 is applied over guide member 58, or may be bonded by adhesive. For example, the components of cylinder 256 may be made of stainless steel, except piston 256c which may be made of rubber.

To steer the sew tip, an operator of the suturing instrument 16 turns the thumb wheel 248 changing the volume of fluid 245 in chamber 240, and moving the fluid into or out of outlet 248 and tube 250. In response, the volume of fluid 245 in chamber 256c of cylinder 256 changes, and piston 256c and rod 258 moves in cylinder 238 causing the rod to extend or retract to flex tissue engaging end 16a, via flexure coupler 260. For purposes of illustration, arrows 239 indicate flexure of the tissue engaging end 16a of instrument 16. Fluid 245 may be, for example, water. This provide for a hydraulic steering mechanic which an operator of the instrument 16 can use to provide additional control in positioning the tissue engaging end during suturing, such positioning being independent of other steerability of the tissue engaging as may be provided by flexure of gastroscope's shaft 14b.

Alternatively, cylinder 256 may be replaced by a folding piston 262, as shown in FIG. 42B and in more detail in FIG. 42C. Folding piston 262 has walls defining a cavity 262a which can longitudinally expand or contract due to changes in volume 263 of liquid 245 contained in the cavity from movement of the fluid through an opening 262b in one of the walls to which tube 250 is connected, such as by adhesive bonding. Rod 258 is attached to end 262d of folding piston 262, by adhesive bonding or is molded to end 262d. Folding piston 262 may be made of plastic, stainless steel, or of heat shrink tubing.

Figure 45A:
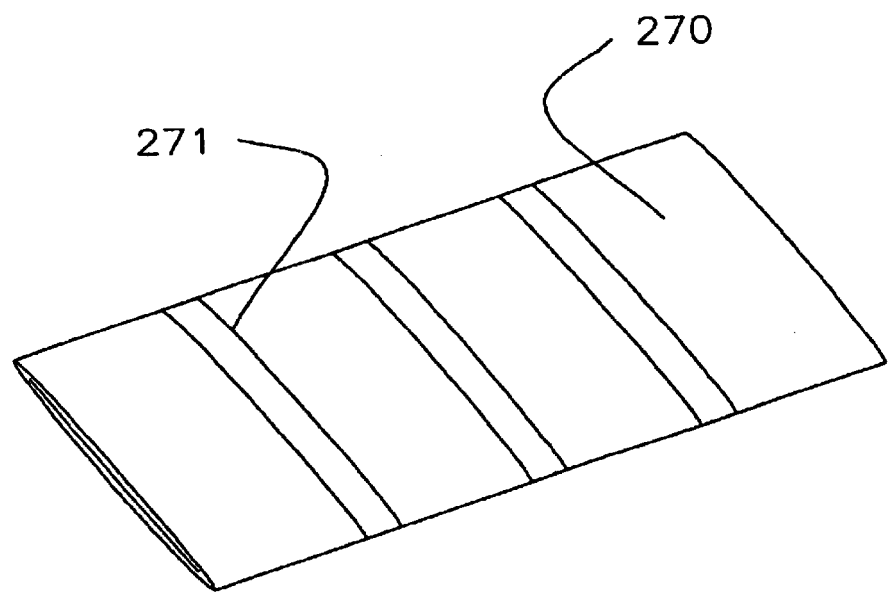
Figure 45B:
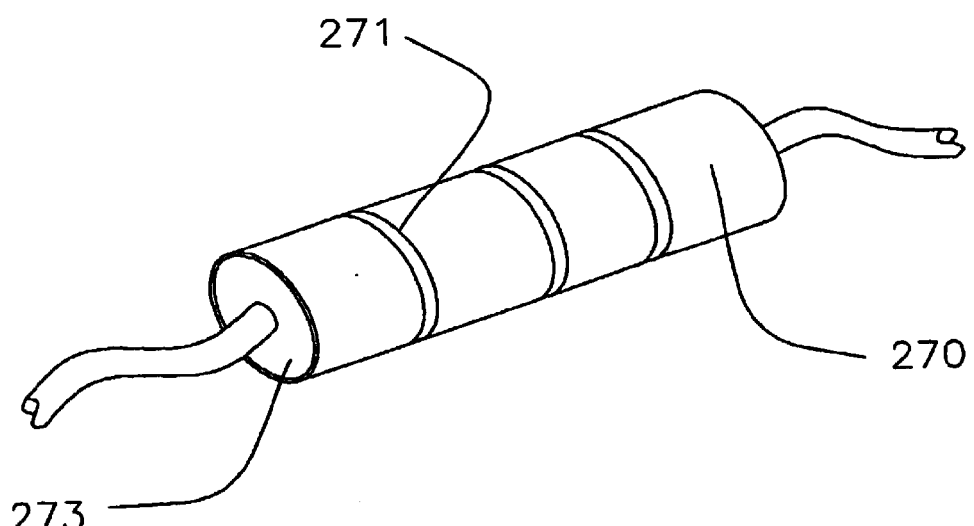
Figure 45C:
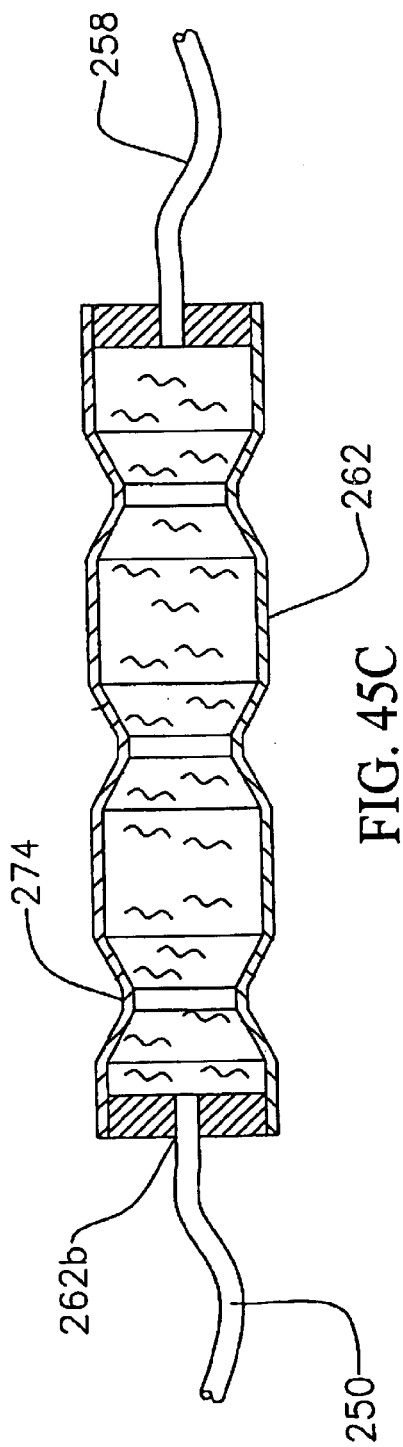
Figure 45D:
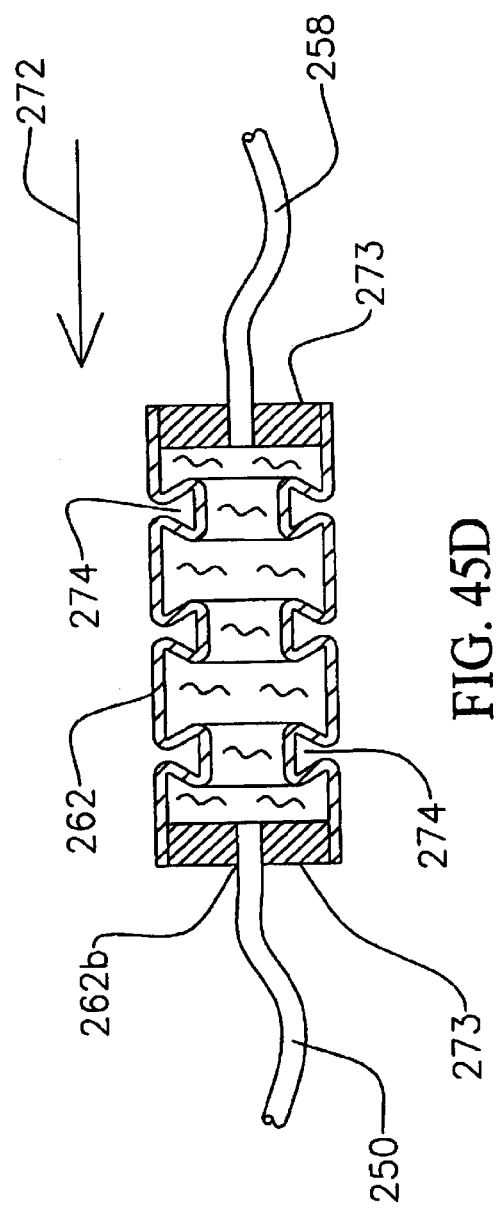

Folding piston 262 can be manufactured with a process using thin walled transparent or white heat shrink plastic tube 270 made from a non-elastic plastic, like polyester. FIG. 45A shows dark, light absorbing, lines 271 printed directly onto the tube 270 when it is collapsed flat. FIG. 45B shows the same tube 270 having plugs 273 with openings 262b into the tube, and pressurized with a medium (not shown), such as water or air, through conduits to one or both openings 262b. Water is a preferred pressurized medium, because it also acts as heat sink to ensure localized heating of the tube only at the desired, printed sites. An appropriate fluence of light, such as produced by a laser, for a specific duration to generate heat along such dark lines of the tube 270 provides controlled radial and axial shrinkage of the tube (FIG. 45C). Such changes to the tube shape permits longitudinal folding of tube 270, as indicated by arrow 272 (FIG. 45D). When the intraluminal pressure and volume are decreased and direct outside pressure is applied to either or both ends of the tube 270, such as via opening 262b, the tube can collapse in length by folding in near the heat shrank zones 274, and thus provide folding piston 262. By increasing pressure and volume within folding piston 262, the folded zones 274 will reexpand longitudinally to re-establish the length of the folding piston 262. By controlling volume and pressure within the folding piston 262, piston length is readily altered. Alternatively, light activated thermal modification of heat shrink tubing can be achieved by using a well controlled circumferential application of focused light, such as laser light, or by careful masking of the heat shrink tubing, or by placing a compliant marked mandrel or tube within a clear heat shrink tube and exposing to appropriate lighting conditions.

In a further alternative, a wire 263 may replace tube 250, such that a mechanical steering mechanism is provided. As shown in FIG. 44, wire 263 follows the same path as tube 250, except that a piston in no longer required in cylinder 238. Instead, the wire 263 is coupled in cylinder 238 to shaft 244a to a ball 265, which is retained in a socket 267 formed at the end of the shaft 244a. A cap 269 has a hole for wire 263 and is received and attached to the socket, such as by welding or brazing, to retain the ball onto the socket, but enable rotation of the ball so that the rotation of the shaft 244a is not transferred to the wire 264. The wire passes through a tube 266, such as made of stainless steel extending between outlet 248 and opening 252 of the rigid tube 52

(FIG. 44). Tube 266 is attached to opening 252, such as by welding or brazing. The wire passes along one of tracks 53d of guide member 53 extending with the guide member through rigid tube 52, and then through hole 254 of coupler member 56 through its tab 56a and 56d, along one of tracks 58d of guide member 58 to the sew tip 98 (FIG. 44A). Wire 262 is attached to a hole 268 extending into tab 100 of the sew tip 98, such as by welding or brazing.

From the foregoing description, it will be apparent that there has been provided an improved system and method for endoscopic suturing. Variations and modifications in the herein described system and method in accordance with the invention will undoubtedly suggest themselves to those skilled in the art. For example, the entire shaft 16b or 134 of instruments 16 or 130, respectively, may be flexible along their length. Accordingly, the foregoing description should be taken as illustrative and not in a limiting sense.

What is claimed is:

1. A system for endoscopic suturing using an endoscope having a flexible shaft with a distal end comprising:
    a flexible tube having first and second ends, said flexible tube being attachable at one or more locations along the outside of said shaft of said endoscope to enable said tube to flex with flexing of said shaft of said endoscope; and
    a tip attachable to said distal end of said shaft of said endoscope having an opening through which said second end of said flexible tube is received, wherein said flexible tube operates as a conduit for passage of one or more instruments, wherein at least two of said instruments renresents a suturing instrument and a suture securing instrument which are separately insertable through said flexible tube.

2. A system for endoscopy using an endoscope having a flexible shaft with a distal end comprising:
    a flexible tube having first and second ends, said flexible tube being attachable at one or more locations along the outside of said shaft of said endoscone to enable said tube to flex with flexing of said shall of said endoscope;
    a tip attachable to said distal end of said shaft of said endoscope having an opening through which said second end of said flexible tube is received, wherein said flexible tube operates as a conduit for passage of one or more instruments; and
    a plurality of tube guides, each of said plurality of tube guides being attachable at a different one of said locations along the outside of said shaft of said endoscope and has an opening through which said flexible tube extends, and said flexible tube is slidable through said opening of the tube guide in response to flexing of said shaft of said endoscope.

3. The system according to claim 1 further comprising:
    a cannula attached to said first end of said flexible tube in which each of said instruments passes through said cannula into said flexible tube.

4. The system according to claim 1 wherein said suturing instrument has a shaft sufficiently flexible to enable passage through said tube.

5. The system according to claim 1 wherein said tissue suturing instrument further comprises means for engaging tissue having a sew tip with a gap, said sew tip being coupled to said shaft of said tissue suturing instrument, and a sleeve over said sew tip having one end capped and an opening to at least said gap, and said system further comprising means for providing suction is a channel along said shaft to said gap of said sew tip to enable tissue to be pulled into said gap.

6. The system according to claim 5 wherein said tissue suturing instrument has at least one needle in said sew tip, and means for driving said needle forward through said suctioned tissue into a ferrule having one end of suture, and retracting said needle through said suction tissue with said ferrule.

7. The system according to claim 1 wherein said suturing instrument further comprises a tissue engaging end coupled to said shaft of said suturing instrument, and said shaft of said suturing instrument has a channel for applying suction to said tissue engaging end of said tissue suturing instrument, and means for connecting to said channel through said shaft of said suturing instrument for applying vacuum establishing said suction.

8. A system for endoscopic suturing using an endoscope having a flexible shaft with a distal end comprising:
    a flexible tube having first and second ends, said flexible tube being attachable at one or more locations along the outside of said shaft of said endoscope to enable said tube to flex with flexing of said shaft of said endoscope; and
    a tip attachable to said distal end of said shaft of said endoscope having an opening through which said second end of said flexible tube is received, wherein said flexible tube operates as a conduit for passage of one or more instruments, wherein at least one of said instruments represents a suturing instrument having a shaft sufficiently flexible to enable passage through said tube, and said suturing instrument further comprises a tissue engaging end coupled to said shaft of said suturing instrument and a housing coupled to said shaft of said instrument, in which said shaft of said suturing instrument has a first section and a second section, and said first section is rigid and extends from said housing, and said second section is flexible and extends from the first section to the tissue engaging end of said suturing instrument.

9. The system according to claim 8 wherein said first section of said shaft of said suturing instrument has a rigid tube and a first guide member in said tube having a plurality of tracks for at least one needle and suture, and said second section of said shaft has a second guide member having a plurality of tracks for at least one needle and suture, and said shall has a coupler member for coupling said first and second guide members to each other.

10. The system according to claim 9 wherein a wire is attached to said coupler member through said second guide member and attached into said tissue engaging end.

11. The system according to claim 8 wherein said suturing instrument further comprises means for translating rotation of one of said housing and said first section to said second section of said shaft and said tissue engaging end of said suturing instrument.

12. The system according to claim 8 wherein said suturing instrument further comprises at least one needle which extends through said shaft of the suturing instrument to said tissue engaging end.

13. The system according to claim 8 wherein said suturing instrument further comprises one or more needles which extends through said shaft of the suturing instrument to said tissue engaging end, in which each of said needles comprises first and second members and a spring which couples said first and second members, and said second member has a tip positionable in said tissue engaging end.

14. The system according to claim 13 wherein said second section of said shaft of said suturing instrument has a tube having holes extending through said tube of said second section for at least said needles.

15. The system according to claim 13 wherein said second section of said shaft of said suturing instrument has a flexible tube for each of said needles, and each of said needles passes through said flexible tube of said second section to said tissue engaging end.

16. The system according to claim 15 wherein said flexible tube of said second section of said shaft of said suturing instrument comprises a spring having two ends and having an outer sheath attached to said two ends to restrict elongation of the spring while enabling flexure of the flexible tube of said second section.

17. The system according to claim 13 wherein said needles extend through said shaft of the suturing instrument and said spring of each of said needles is located in said second section to assist in flexibility of said needles.

18. The system according to claim 13 wherein each of said needles further comprises a cable or wire which couples said spring between said first and second members.

19. The system according to claim 1 wherein said system further comprises an endoscope representing a gastroscope.

20. The system according to claim 1 wherein said instruments are capable of operating independently of said endoscope.

21. The system according to claim 1 wherein said suture securing instrument comprises a shaft which is at least partially flexible to enable passage through said tube.

22. The system according to claim 1 wherein said suture securing instrument further comprises means for retaining in a sleeve member the two free ends of a loop of suture extending through tissue, and means for cutting the two free ends of the loop of suture near said sleeve member.

23. The system according to claim 1 wherein said suture securing instrument is not part of an endoscope.

24. The system according to claim 1 wherein said shaft at least one of said instruments has a shaft having a distal end, and said system further comprises an endoscope having means for viewing the distal end of said one of said instruments when said distal tissue engaging end is located through said first and second ends of said tube.

25. The system according to claim 4 wherein said shaft of said suturing instrument has a distal tissue engaging end, and a channel for applying positive or negative air pressure to said end of said tissue suturing instrument, and means for connecting to said channel through said shaft for applying said positive or negative air pressure.

26. A system for endoscopic suturing using an endoscope having a flexible shaft with a distal end comprising:
a flexible tube having first and second ends, said flexible tube being attachable at one or more locations along the outside of said shaft of said endoscope to enable said tube to flex with flexing of said shaft of said endoscope; and
a tip attachable to said distal end of said shaft of said endoscope having an opening through which said second end of said flexible tube is received, wherein said flexible tube operates as a conduit for passage of one or more instruments, wherein said suturing instrument further comprises a distal tissue engaging end coupled to said shaft of said suturing instrument, in which said shaft of said suturing instrument has a channel to said tissue engaging end and an opening to said channel, and said flexible tube has a port capable of enabling suction to be provided to said tissue engaging end through said opening and channel of said shaft, in which said opening of said tip has a seal for engaging with said tissue engaging end of said suturing instrument to enable said suction to be provided through said opening of said shaft.

27. The system according to claim 1 further comprising an endoscope having a shaft attached to said flexible tube and said tip.

28. The system according to claim 1 further comprising means for locking the position of at least one of said instruments with respect to said flexible tube at the tip of said flexible tube.

29. The system according to claim 1 wherein at least one of said instruments represents has a shaft sufficiently flexible to enable passage through said tube, and said shaft of said one of said instruments has a distal end having a substantially cylindrical outer surface with one or more protrusion members along said outer surface of said distal end, and said opening of said tip having one or more slots into which said protrusion members are receivable to lock the position of said one of said instruments with respect to said flexible tube at said tip.

30. The system according to claim 4 wherein said suturing instrument further comprises a tissue engaging end coupled to the shaft of said suturing instrument, and means for steering said tissue engaging end.

31. The system according to claim 30 wherein said steering means is one of hydraulically and mechanically actuated.

32. A system for endoscopic suturing in the body of a patient comprising:
an endoscope having a shaft and an internal channel along said shaft locatable in the body of a patient;
a suturing instrument having at least a partially flexible shaft which is locatable through said internal channel of said endoscope to locate at least one loop of suture in the body of a patient; and
a suture securing instrument having at least a partially flexible shaft which is locatable through said internal channel of said endoscope to retain in a sleeve member the loop of suture and then cut the suture extending from said sleeve member to secure said suture in the body of the patient.

33. The system according to claim 1 wherein said flexible tube is attachable to and detachable from different types of endoscopes.

34. The system according to claim 1 wherein said system further comprises an endoscope having a shaft with a channel for passage of tools and said flexible tube is of a diameter larger than said channel.

35. The system according to claim 1 wherein each of said instruments is sufficiently flexible to be locatable through said first and second ends of said tube when having one or more flexures in accordance with flexing of said shaft of said endoscope.

36. The system according to claim 1 wherein said an endoscope has an internal channel along said shaft, and at least one of said suturing instrument and said suture securing instrument is locatable through said internal channel of said endoscope.

37. A system of endoscopic suturing comprising:
means for attaching an external tube along a flexible shaft of an endoscope to flex with flexing of said shaft;
a suturing instrument locatable through said external tube attached to said endoscope to locate at least one loop of suture through tissue in a body of a patient; and
a suture securing instrument having at least a partially flexible shaft which is locatable through said external tube attached to said endoscope to retain in a sleeve member the loop of suture and then cut the suture extending from said sleeve member to secure said suture in the tissue.

38. A system of endoscopic suturing comprising:
an endoscope locatable in the body of a patient having a flexible shaft with a steerable distal end;
a flexible guide tube having first and second ends locatable outside said shaft, and have the first end attached to the distal end of said shaft to be steered with steering of said distal end of said endoscope; and
at least one tissue suturing instrument and one suture securing instrument, each having a shaft which is sufficiently flexible to be insertable through the flexible guide tube when the flexible guide tube is located in a body of a patient.

39. The system according to claim 38 further comprising a plurality of tube guides attached at a different locations along said shaft of said endoscope, each of said tube guides having an opening through which said flexible tube extends, and said flexible tube is slidable through said opening of the tube guide in response to flexing of said shaft of said endoscope to maintain said guide tube substantially coaxial with said shaft of said endoscope.

40. The system according to claim 2 wherein said tube guides are attachable to the shaft of said endoscope at the same circumferential position along the outside of the shaft of said endoscope.

41. The system according to claim 2 wherein at least one of said instruments represents a suturing instrument or a suture securing instrument insertable through said flexible tube.

42. The system according to claim 2 wherein at least one of said instruments represents has a shaft sufficiently flexible to enable passage through said tube, and said shaft of said one of said instruments has a distal end having a substantially cylindrical outer surface with one or more protrusion members along said outer surface of said distal end, and said opening of said tip having one or more slots into which said protrusion members are receivable to lock the position of said one of said instruments with respect to said flexible tube at said tip.

43. The system according to claim 42 wherein said shaft of said suturing instrument has a distal tissue engaging end, and a channel for applying positive or negative air pressure to said end of said tissue suturing instrument, and means for connecting to said channel through said shaft for applying said positive or negative air pressure.

44. The system according to claim 42 wherein said suturing instrument further comprises a distal tissue engaging end coupled to said shaft of said suturing instrument, in which said shaft of said suturing instrument has a channel to said tissue engaging end and an opening to said channel, and said flexible tube has a port capable of enabling suction to be provided to said tissue engaging end through said opening and channel of said shaft, in which said opening of said tip has a seal for engaging with said tissue engaging end of said suturing instrument to enable said suction to be provided through said opening of said shaft.

45. The system according to claim 42 wherein said suturing instrument further comprises a tissue engaging end coupled to the shaft of said suturing instrument, and means for steering said tissue engaging end.

46. A system for endoscopic suturing using an endoscope having a flexible shaft with a distal end comprising:
a flexible tube having first and second ends, said flexible tube being attachable at one or more locations along the outside of said shaft of said endoscope to enable said tube to flex with flexing of said shall of said endoscope; and
a tip attachable to said distal end of said shaft of said endoscope having an opening through which said second end of said flexible tube is received, wherein said flexible tube operates as a conduit for passage of one or more instruments, wherein at least one of said instruments represents a suturing instrument having a shall sufficiently flexible to enable passage through said tube, and said suturing instrument further comprises a tissue engaging end coupled to said shaft of said suturing instrument and a housing coupled to said shall of said instrument, in which said shaft of said suturing instrument has a first section and a second section, and said first section is rigid, and said second section is flexible and extends from the first section to the tissue engaging end of said suturing instrument.

47. A system for endoscopy using an endoscope having a flexible shaft with a distal end comprising:
a flexible tube;
a member for distally attaching the shaft of said endoscope and said flexible tube in which said flexible tube provides a conduit for passage of one or more instruments along side said shaft of said endoscope; and
one or more tube guides attachable along substantial length of said shall of said endoscope, each of said tube guides having an opening through which said flexible tube extends, and said flexible tube slides through said openings of said tube guides when said shaft of said endoscope is flexed in multiple dimensions to maintain said flexible tube in a substantially coaxial orientation with the shaft of said endoscope.

48. The system according to claim 47 wherein said tube guides are attached at the same circumferential location along said shaft of said endoscope.

49. The system according to claim 47 wherein at least one of said instruments represents has a shaft sufficiently flexible to enable passage through said tube, and said shaft of said one of said instruments has a distal end having a substantially cylindrical outer surface with one or more protrusion members along said outer surface of said distal end, and said opening of said tip having one or more slots into which said protrusion members are receivable to lock the position of said one of said instruments with respect to said flexible tube at said tip.

50. The system according to claim 47 wherein at least one of said instruments represents a suturing instrument or a suture securing instrument insertable through said flexible tube.

51. The system according to claim 50 wherein said shaft of said suturing instrument has a distal tissue engaging end, and a channel for applying positive or negative air pressure to said end of said tissue suturing instrument, and means for connecting to said channel through said shaft for applying said positive or negative air pressure.

52. The system according to claim 50 wherein said suturing instrument further comprises a distal tissue engaging end coupled to said shaft of said suturing instrument, in which said shaft of said suturing instrument has a channel to said tissue engaging end and an opening to said channel, and said flexible tube has a port capable of enabling suction to be provided to said tissue engaging end through said opening and channel of said shaft, in which said opening of said tip has a seal for engaging with said tissue engaging end of said suturing instrument to enable said suction to be provided through said opening of said shaft.

53. The system according to claim 50 wherein said suturing instrument further comprises a tissue engaging end coupled to the shaft of said suturing instrument, and means for steering said tissue engaging end.

* * * * *